US011834479B2

(12) United States Patent
Romesberg et al.

(10) Patent No.: US 11,834,479 B2
(45) **Date of Patent: *Dec. 5, 2023**

(54) NUCLEOSIDE TRIPHOSPHATE TRANSPORTER AND USES THEREOF

(71) Applicant: THE SCRIPPS RESEARCH INSTITUTE, La Jolla, CA (US)

(72) Inventors: Floyd E. Romesberg, La Jolla, CA (US); Yorke Zhang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,741

(22) Filed: Apr. 3, 2020

(65) Prior Publication Data

US 2020/0277342 A1 Sep. 3, 2020

Related U.S. Application Data

(63) Continuation of application No. 16/546,100, filed on Aug. 20, 2019, now Pat. No. 10,696,720, which is a continuation of application No. 16/312,901, filed as application No. PCT/US2017/039133 on Jun. 23, 2017, now abandoned.

(60) Provisional application No. 62/354,650, filed on Jun. 24, 2016.

(51) Int. Cl.
*C12N 15/10* (2006.01)
*C12N 15/11* (2006.01)
*C12N 15/90* (2006.01)
*C12N 9/22* (2006.01)
*C07K 14/405* (2006.01)

(52) U.S. Cl.
CPC .............. *C07K 14/405* (2013.01); *C12N 9/22* (2013.01); *C12N 15/10* (2013.01); *C12N 15/11* (2013.01); *C12N 15/90* (2013.01); *C12N 2310/20* (2017.05); *C12N 2800/80* (2013.01)

(58) Field of Classification Search
None
See application file for complete search history.

(56) References Cited

U.S. PATENT DOCUMENTS 3,687,808 A 8/1972 Merigan, Jr. et al.
4,469,863 A 9/1984 Ts et al.
4,476,301 A 10/1984 Imbach et al.
4,587,044 A 5/1986 Miller et al.
4,605,735 A 8/1986 Miyoshi et al.
4,667,025 A 5/1987 Miyoshi et al.
4,683,195 A 7/1987 Mullis et al.
4,683,202 A 7/1987 Mullis
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,845,205 A 7/1989 Huynh et al.
4,849,513 A 7/1989 Smith et al.
4,876,335 A 10/1989 Yamane et al.
4,904,582 A 2/1990 Tullis
4,910,300 A 3/1990 Urdea et al.
4,948,882 A 8/1990 Ruth
4,958,013 A 9/1990 Letsinger
4,965,188 A 10/1990 Mullis et al.
4,981,957 A 1/1991 Lebleu et al.
5,015,733 A 5/1991 Smith et al.
5,023,243 A 6/1991 Tullis
5,034,506 A 7/1991 Summerton et al.
5,082,830 A 1/1992 Brakel et al.
5,093,232 A 3/1992 Urdea et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spielvogel et al.
5,134,066 A 7/1992 Rogers et al.
5,138,045 A 8/1992 Cook et al.
5,166,315 A 11/1992 Summerton et al.
5,175,273 A 12/1992 Bischofberger et al.
5,177,196 A 1/1993 Meyer, Jr. et al.
5,185,444 A 2/1993 Summerton et al.
5,188,897 A 2/1993 Suhadolnik et al.
5,214,134 A 5/1993 Weis et al.
5,214,136 A 5/1993 Lin et al.
(Continued)

FOREIGN PATENT DOCUMENTS

EP 0614907 A1 9/1994
EP 0629633 A2 12/1994
(Continued)

OTHER PUBLICATIONS

Arenas-Ramirez et al. Improved cancer immunotherapy by a CD25-mimobody conferring selectivity to human interleukin-2. Sci Transl Med 8:367ra166 (Nov. 30, 2016). 13 pages.
(Continued)

*Primary Examiner* — Marsha Tsay
(74) *Attorney, Agent, or Firm* — Thomas Fitting

(57) ABSTRACT

Disclosed herein are proteins, methods, cells, engineered microorganisms, and kits for generating a modified nucleoside triphosphate transporter from *Phaeodactylum tricornutum*. Also disclosed herein proteins, methods, cells, engineered microorganisms, and kits for production of a nucleic acid molecule that comprises an unnatural nucleotide utilizing a modified nucleoside triphosphate transporter from *Phaeodactylum tricornutum*.

25 Claims, 24 Drawing Sheets

Specification includes a Sequence Listing.

(56) References Cited

U.S. PATENT DOCUMENTS 5,216,141 A 6/1993 Benner
5,218,105 A 6/1993 Cook et al.
5,235,033 A 8/1993 Summerton et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,319,080 A 6/1994 Leumann
5,321,131 A 6/1994 Agrawal et al.
5,359,044 A 10/1994 Cook et al.
5,367,066 A 11/1994 Urdea et al.
5,371,241 A 12/1994 Brush
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,306 A 7/1996 Agrawal et al.
5,541,307 A 7/1996 Cook et al.
5,541,313 A 7/1996 Ruth
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,595,899 A 1/1997 Sato et al.
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,645,985 A 7/1997 Froehler et al.
5,646,265 A 7/1997 McGee
5,656,493 A 8/1997 Mullis et al.
5,658,873 A 8/1997 Bertsch-Frank et al.
5,663,312 A 9/1997 Chaturvedula
5,670,633 A 9/1997 Cook et al.
5,677,437 A 10/1997 Teng et al.
5,677,439 A 10/1997 Weis et al.
5,681,941 A 10/1997 Cook et al.
5,688,941 A 11/1997 Cook et al.
5,700,920 A 12/1997 Altmann et al.
5,714,331 A 2/1998 Buchardt et al.
5,719,262 A 2/1998 Buchardt et al.
5,750,692 A 5/1998 Cook et al.
5,763,588 A 6/1998 Matteucci et al.
5,830,653 A 11/1998 Froehler et al.
5,888,732 A 3/1999 Hartley et al.
6,005,096 A 12/1999 Matteucci et al.
6,143,557 A 11/2000 Hartley et al.
6,171,861 B1 1/2001 Hartley et al.
6,268,490 B1 7/2001 Imanishi et al.
6,270,969 B1 8/2001 Hartley et al.
6,277,608 B1 8/2001 Hartley et al.
6,525,191 B1 2/2003 Ramasamy
6,670,461 B1 12/2003 Wengel et al.
6,720,140 B1 4/2004 Hartley et al.
6,770,748 B2 8/2004 Imanishi et al.
6,794,499 B2 9/2004 Wengel et al.
6,955,807 B1 10/2005 Shanafelt et al.
7,034,133 B2 4/2006 Wengel et al.
7,053,207 B2 5/2006 Wengel
7,399,845 B2 7/2008 Seth et al.
7,427,672 B2 9/2008 Imanishi et al.
10,513,706 B2 12/2019 Romesberg et al.
10,626,138 B2 4/2020 Romesberg et al.
2002/0007051 A1 1/2002 Cheo et al.
2004/0171570 A1 9/2004 Allerson et al.
2005/0130923 A1 6/2005 Bhat et al.
2006/0074035 A1 4/2006 Hong et al.
2007/0287831 A1 12/2007 Seth et al.
2008/0039618 A1 2/2008 Allerson et al.
2008/0300163 A1 12/2008 Cho et al.
2012/0244112 A1 9/2012 Ast et al.
2014/0328791 A1 11/2014 Bossard et al.
2017/0369871 A1 12/2017 Ptacin et al.
2019/0218257 A1 7/2019 Romesberg et al.
2019/0375802 A1 12/2019 Romesberg et al.
2019/0375803 A1 12/2019 Romesberg et al.
2019/0376054 A1 12/2019 Ptacin et al.
2020/0017540 A1 1/2020 Romesberg et al.
2020/0024597 A1 1/2020 Ptacin et al.
2020/0040027 A1 2/2020 Romesberg et al.
2020/0095591 A1 3/2020 Romesberg et al.
2020/0131555 A1 4/2020 Ptacin et al.
2020/0224234 A1 7/2020 Romesberg et al.
2020/0318122 A1 10/2020 Romesberg et al.

(56) References Cited

U.S. PATENT DOCUMENTS

2020/0377877 A1 12/2020 Romesberg et al.
2020/0392550 A1 12/2020 Romesberg et al.
2021/0222147 A1 7/2021 Ptacin et al.

FOREIGN PATENT DOCUMENTS

WO WO-9213869 A1 8/1992
WO WO-9414226 A1 6/1994
WO WO-9735869 A1 10/1997
WO WO-9914226 A2 3/1999
WO WO-9962923 A2 12/1999
WO WO-0105801 A1 1/2001
WO WO-0132887 A1 5/2001
WO WO-02070533 A2 9/2002
WO WO-2004007713 A1 1/2004
WO WO-2004106356 A1 12/2004
WO WO-2005021570 A1 3/2005
WO WO-2005026187 A1 3/2005
WO WO-2005045015 A2 5/2005
WO WO-2006049297 A1 5/2006
WO WO-2007015557 A1 2/2007
WO WO-2007066737 A1 6/2007
WO WO-2007090071 A2 8/2007
WO WO-2007134181 A2 11/2007
WO WO-2008101157 A1 8/2008
WO WO-2008150729 A2 12/2008
WO WO-2008154401 A2 12/2008
WO WO-2009006478 A2 1/2009
WO WO-2009123216 A1 10/2009
WO WO-2011043385 A1 4/2011
WO WO-2011139699 A2 11/2011
WO WO-2014160025 A2 10/2014
WO WO-2015021432 A1 2/2015
WO WO-2015086795 A1 6/2015
WO WO-2015157555 A2 10/2015
WO WO-2016073433 A1 5/2016
WO WO-2016094867 A1 6/2016
WO WO-2016115168 A1 7/2016
WO WO-2017106767 A1 6/2017
WO WO-2017223528 A1 12/2017
WO WO-2019014262 A1 1/2019
WO WO-2019014267 A1 1/2019
WO WO-2019133883 A1 7/2019
WO WO-2021067313 A1 4/2021
WO WO-2022087475 A1 4/2022

OTHER PUBLICATIONS

Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Boyman et al. Selective Stimulation of T Cell subsets with Antibody-Cytokine Immune Complexes. Science 311:1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Branca. Rekindling cancer vaccines. Nat Biotechnol 34(10):1019-1025 (2016).
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).
Chastgner et al. Lack of intermediate-affinity interleukin-2 receptor in mice leads to dependence on interkeukin-2 receptor α,β and γ chain expression for T cell growth. Eur J Immunol 26:201-206 (1996).
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Dranoff. Cytokines in cancer pathogenesis and cancer therapy. Nature Reviews Cancer 4:11-22 (2004).
Floros et al. Anticancer Cytokines: Biology and Clinical Effects of Interferon-α2, Interleukin (IL)-2, IL-15, IL-21, and IL-12. Semin Oncol 42(4):539-548 (2015).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Insight-Esprit Study Group et al. Interleukin-2 Therapy in Patients with HIV Infection. N Engl J Med. 361(16):1548-59 (2009).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination can-

(56) References Cited

OTHER PUBLICATIONS cer immunotherapy: Overcoming limitations of aldesleukin and conventional IL-2-based immunocytokines. Oncoimmunology 6(3):e1277306 (2017).
Krieg et al. Improved IL-2 immunotherapy by selective stimulation of IL-2 receptors on lymphocytes and endothelial cells. PNAS USA 107(26):11906-11911 (Jun. 29, 2010).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lazear et al. Targeting of IL-2 to cytotoxic lymphocytes as an improved method of cytokine-driven immunotherapy. Oncoimmunology 6(2):e1265721 (2017).
Letourneau et al. IL-2/anti-IL-2 antibody complexes show strong biological activity by avoiding interaction with IL-2 receptor alpha subunit CD25. PNAS USA 107:2171-2176 (2010).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nicolini et al. The FAP-IL2v Immunocytokine is a Versatile Combination Partner for Cancer Immunotherapy. Poster (SITC 2018).
Parisi et al. Enhanced expansion and tumor targeting of adoptively transferred T cells with NKTR-214. Poster Abstract #3566. (AACR Apr. 17, 2018).
Pfannenstiel et al. A Novel, Individualized Xenograft Model of Cancer Immunotherapy and Tumor Growth Inhibition by ALKS 4230. Poster #P351 (SITC 2017).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Roessler et al. Cooperative interactions between the interleukin 2 receptor α and β chains later the interleukin 2-binding affinity of the receptor subunits. PNAS USA 91:3344-3347 (1994).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sharma et al. NKTR-214 enhances anti-tumor T cell immune responses induced by checkpoint blockade or vaccination. Poster (SITC 2017).
Siegel et al. Interleukin-2 Toxicity. J Clin Oncol 9(4):694-704 (1991).
Sim et al. IL2 Variant Circumvents ICOS+ Regulatory T-cell Expansion and Promotes NK Cell Activation. Cancer Immunol Res. 4(11):983-995 (Nov. 2016).
Sivakumar et al. Comparison of Vascular Leak Syndrome in Mice treated with IL21 or IL2. Comparative Medicine 63(1):13-21 (2013).
Spangler et al. Antibodies to Interleukin-2 Elicit Selective T Cell Subset Potentiation through Distinct Conformational Mechanism. Immunity 42:815-825 (2015).
Stauber et al. Crystal Structure of the IL-2 signaling complex: Paradigm for a heterotrimeric cytokine receptor. PNAS 103(8):2788-2793 (2006).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,100, filed Aug. 20, 2019.
U.S. Appl. No. 16/577,347, filed Sep. 9, 2020.
U.S. Appl. No. 16/591,422, filed Oct. 2, 2019.

(56) References Cited

OTHER PUBLICATIONS

U.S. Appl. No. 16/900,154, filed Jun. 12, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vazquez-Lombardi et al. Potent antitumour activity of the interleukin-2-Fc fusion proteins requires Fc-mediated depletion of regulatory T-cells. Nat Comm 8:15373 (2017).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, β, and γc Receptors. Science 310:1159-63 (2005).
Webster et al. In vivo expansion of T reg cells with IL-2-mAb complexes: induction of resistance to EAE and long-term acceptance of islet allografts without immunosuppression. J Med Chem 206(4):751-760 (2009).
Yamaguchi et al. Role of IL-5 in IL-2-induced eosinophilia. In vivo and in vitro expression of IL-5 mRNA by IL-2. J Immunol 145:873-877 (1990).
Zalevsky. Jefferies 2016 Global Healthcare Conference. PowerPoint presentation (Nov. 16, 2016).
Adhikary et al. Adaptive Mutations Alter Antibody Structure and Dynamics During Affinity Maturation. Biochemistry 54(11):2085-93 (2015).
Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).
Ambrogelly et al. Pyrrolysine is not hardwired for cotranslational insertion at UAG condons. PNAS 104(9):3141-3146 (2007).
Amiri et al. Deep origin of plastid/parasite ATP/ADP translocases. J. Mol. Evol. 56:137-150 (2003).
Ast et al. Diatom plastids depend on nucleotide import from the cytosol. PNAS USA 106:3621-3626 (2009).
Beigelman et al. Synthesis of 5'-C-Methyl-D-allo- & L-Talo-ribonucleoside 3' -O- Phosphoramidites & Their Incorporation into Hammerhead Ribozymes. Nucleosides and Nucleotides 14(3-5):901-905 (1995).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28(15):2911-2914 (2000).
Betz et al. KlenTaq polymerase replicates unnatural base pairs by inducing a Watson-Crick geometry. Nat Chem Biol 8:612-614 (2012).
Betz et al. Structural insights into DNA replication without hydrogen bonds. J Am Chem Soc 135:18637-18643 (2013).
Bohringer et al. Synthesis of 5'-deoxy-5'-methylphosphonate linked thymidine oligonucleotides. Tet Lett 34:2723-2726 (1993).
Bordo et al. Suggestions for "safe" residue substitutions in site-directed mutagenesis. J Mol Biol 217:721-729 (1991).
Braasch et al. Locked nucleic acid (LNA): fine-tuning the recognition of DNA and RNA. Chem Bio 8:1-7 (2001).
Cameron et al. Tunable protein degradation in bacteria. Nature Biotechnology 32:1276-1281 (2014).
Cann et al. A heterodimeric DNA polymerase: Evidence that members of Euryarchaeota possess a distinct DNA polymerase. PNAS USA 95:14250 (1998).
Cantrell. Vectors for the expression of recombinant proteins in *E. coli*. Methods Mol Biol. 235:257-75 (2003).
Cariello et al. Fidelity of Thermococcus litoralis DNA polymerase (VentTM) in PCR determined by denaturing gradient gel electrophoresis Nucl Acid Res 19:4193-4198 (1991).
Chatterjee et al. A Versatile Platform for Single- and Multiple-Unnatural Amino Acid Mutagenesis in *Escherichia coli*. Biochemistry 52(10):1828-1837 (2013).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Chien et al. Deoxyribonucleic acid polymerase from the extreme thermophile Thermus aquaticus. J Bacteriol 127:1550-1557 (1976).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
Database UniParc [Online] May 31, 2010 (May 31, 2010), Database accession No. UPI0001D42ADE (2 pgs).
Datsenko et al. One-step inactivation of chromosomal genes in *Escherichia coli* K-12 using PCR products. PNAS USA 97(12):6640-6645 (2000).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Deuschle et al. Promoters of *Escherichia coli*: a hierarchy of in vivo strength indicates alternate structures. EMBO J 5:2987-2994 (1986).
Dhami et al. Systematic exploration of a class of hydrophobic unnatural base pairs yields multiple new candidates for the expansion of the genetic alphabet. Nucleic Acids Res 42:10235-10244 (2014).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Doudna et al. Genome editing. The new frontier of genome engineering with CRISPR-Cas9. Science 346:1258096 (2014).
Dupradeau et al. Differential solvation and tautomer stability of a model base pair within the minor and major grooves of DNA. J Am Chem Soc 127(44):15612-7 (2005).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).

(56) References Cited

OTHER PUBLICATIONS

Engler et al. A one pot, one step, precision cloning method with high throughput capability. PLOS One 3:e3647 (2008).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Fluman et al. mRNA-programmed translation pauses in the targeting of *E. coli* membrane proteins. eLife 2014; 3:e03440.
Fu et al. Improving CRISPR-Cas nuclease specificity using truncated guide RNAs. Nat Biotechnol 32:279-284 (2014).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gibson, et al. Enzymatic assembly of DNA molecules up to several hundred kilobases. Nat Methods. May 2009;6(5):343-5.
Gietz et al. Improved method for high efficiency transformation of intact yeast cells. Nucleic Acids Res 20:1425 (1992).
Goodman et al. Causes and effects of N-terminal codon bias in bacterial genes. Science 342:475-479 (2013).
Guo et al. Directed evolution of an enhanced and highly efficient FokI cleavage domain for zinc finger nucleases. J Mot Biol 400:96-107 (2010).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Horvath et al. CRISPR/Cas, the Immune System of Bacteria and Archaea. Science 327:167-170 (2010).
Hsu et al. Development and applications of CRISPR-Cas9 for genome engineering. Cell 157(6):1262-78 (2014).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Johansson et al. The solution structures of mutant calbindin D9k's, as determined by NMR, show that the calcium-binding site can adopt different folds. Biochemistry 35(25):8429-8438 (1996).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).

(56) References Cited

OTHER PUBLICATIONS

Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Khlebnikov et al. Effect of lacY expression on homogeneity of induction from the P(tac) and P(trc) promoters by natural and synthetic inducers. Biotechnol Prog 18:672-674 (2002).
Kim et al. Stability and polymerase recognition of pyridine nucleobase analogues: role of minor-groove H-bond acceptors. Angew Chem Int Ed Engl 45(46):7809-12 (2006).
Kimoto et al. Chemical Biology of Nucleic Acids: Fundamentals and Clinical Applications (eds A. Volker Erdmann, T. Wojciech Markiewicz, & Jan Barciszewski) pp. 131-148 (Springer Berlin Heidelberg, 2014).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kuhlman et al. Site-specific chromosomal integration of large synthetic constructs. Nucleic Acids Res 38:e92 (2010).
Kumar et al. The First Analogues of LNA (Locked Nucleic Acids): Phosphorothioate LNA and 2'-Thio-LNA. Bioorg Med Chem Lett 8:2219-2222 (1998).
Landy. Mechanistic and structural complexity in the site-specific recombination pathways of Int and FLP. Curr Opin Genet Dev. 3(5):699-707 (1993).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lecomte et al. Selective Inactivation of the 3' to 5' exonuclease activity of *Escherichia coli* DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Marraffini et al. CRISPR interference: RNA-directed adaptive immunity in bacteria and archaea. Nat Rev Genet. 11(3):181-90 (2010).
Marshall et al., A link between integral membrane protein expression and simulated integration efficiency. Cell Reports 16(8): 2169-2177 (2016).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc.122:10714-10715 (2000).
Micklefield. Backbone Modification of Nucleic Acids: Synthesis, Structure and Therapeutic Applications. Current Medicinal Chemistry 8:1157-1179 (2001).

(56) References Cited

OTHER PUBLICATIONS

Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mutalik, et al., Precise and reliable gene expression via standard transcription and translation initiation elements. Nature Methods 10:354-360 (2013).
Myers et al. Reverse transcription and DNA amplification by a Thermus thermophilus DNA polymerase. Biochemistry 30:7661-7666 (1991).
Nawrot et al. A novel class of DNA analogs bearing 5'-C-phosphonothymidine units: synthesis and physicochemical and biochemical properties. Oligonucleotides16(1):68-82 (2006).
Nelson et al. N3'→ P5' Oligodeoxyribonucleotide Phosphoramidates: A New Method of Synthesis Based on a Phosphoramidite Amine-Exchange Reaction. J Org Chem 62:7278-7287 (1997).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2017/039133 International Preliminary Report on Patentability dated Jan. 3, 2019.
PCT/US2017/039133 International Search Report and Written Opinion dated Sep. 20, 2017.
PCT/US2018/041503 International Search Report and Written Opinion dated Nov. 7, 2018.
PCT/US2018/045257 International Search Report and Written Opinion dated Nov. 21, 2018.
Peyrottes et al. Oligodeoxynucleoside phosphoramidates (P-NH2): synthesis and thermal stability of duplexes with DNA and RNA targets. Nucleic Acids Res 24:1841-1848 (1996).
Quan et al. Circular polymerase extension cloning for high-throughput cloning of complex and combinatorial DNA libraries. Nat Protoc 6(2):242-251 (2011).
Rath et al. The CRISPR-Cas immune system: biology, mechanisms and applications. Biochimie 117:119-128 (2015).
Romesberg et al. Development of a universal nucleobase and modified nucleobases for expanding the genetic code. Curr Prot Nucleic Acid Chem Chapter 1:Unit 1.5 (2002).
Sabri et al. Knock-in/Knock-out (KIKO) vectors for rapid integration of large DNA sequences, including whole metabolic pathways, onto the *Escherichia coli* chromosome at well-characterised loci. Microb Cell Fact 12:60 (2013).
Saha et al. 5'-Methyl-DNA-A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schlegel et al. De-convoluting the genetic adaptations of *E. coli* C41(DE3) in real time reveals how alleviating protein production stress improves yields. Cell Rep 10:1758-1766 (2015).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Schneider et al. NIH Image to ImageJ: 25 years of image analysis. Nat Methods 9:671-675 (2012).
Schultz et al. Oligo-2'-fluoro-2'-deoxynucleotide N3'→P5' phosphoramidates: synthesis and properties. Nucleic Acids Res 24:2966-2973 (1996).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Shaloiko et al. Effective non-viral leader for cap-independent translation in a eukaryotic cell-free system. Biotechnology and Bioengineering 88(6):730-739 (2004).
Shea et al. Synthesis, hybridization properties and antiviral activity of lipid-oligodeoxynucleotide conjugates. Nucl. Acids Res 18:3777-3783 (1990).
Sikorski et al. A system of shuttle vectors and yeast host strains designed for efficient manipulation of DNA in *Saccharomyces cerevisiae*. Genetics 122:19-27 (1989).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Southern et al. Transformation of mammalian cells to antibiotic resistance with a bacterial gene under control of the SV40 early region promoter. J Mol Appl Genet 1:327-341 (1982).
Srivastava et al. Five- and six-membered conformationally locked 2',4'-carbocyclic ribo-thymidines: synthesis, structure, and biochemical studies. J Am Chem Soc 129(26):8362-8379 (2007).
Stenesh et al. DNA polymerase from mesophilic and thermophilic bacteria. III. Lack of fidelity in the replication of synthetic

(56) References Cited

OTHER PUBLICATIONS polydeoxyribonucleotides by DNA polymerase from Bacillus licheniformis and Bacillus stearothermophilus. Biochim Biophys Acta 475:32-41 (1977).
Sugden et al. A vector that replicates as a plasmid and can be efficiently selected in B-lymphoblasts transformed by Epstein-Barr virus. Mol. Cell. Biol. 5:410-413 (1985).
Svinarchuk et al. Inhibition of HIV proliferation in MT-4 cells by antisense oligonucleotide conjugated to lipophilic groups. Biochimie 75:49-54 (1993).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Takeshita et al. High-copy-number and low-copy-number plasmid vectors for lacZ alpha-complementation and chloramphenicol- or kanamycin-resistance selection. Gene 61, 63-74 (1987).
The Concise Encyclopedia of Polymer Science and Engineering, Kroschwitz, J.I., Ed., John Wiley & Sons pp. 858-859 (1990).
Tuerk. Systematic evolution of ligands by exponential enrichment: RNA ligands to bacteriophage T4 DNA polymerase. Science 249:505-510 (1990).
U.S. Appl. No. 16/312,901 Office Action dated May 1, 2020 .
U.S. Appl. No. 16/546,097 Office Action dated Feb. 7, 2020.
U.S. Appl. No. 16/546,097 Office Action dated Nov. 21, 2019.
U.S. Appl. No. 16/546,100 Office Action dated Feb. 7, 2020.
U.S. Appl. No. 16/546,100 Office Action dated Nov. 27, 2019.
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Verma. Retroviral vectors for gene transfer. In: Microbiology (Leive L et al., eds., Ann. Soc. Microbiol) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wandry et al. Probing unnatural amino acid integration into enhanced green fluorescent protein by genetic code expansion with a high-throughput screening platform. J Biol Eng. 10:11 (2016).
Wang et al. An engineered rare codon device for optimization of metabolic pathways. Scientific Reports 6:20608 (2016).
Wang et al. Biophysical and biochemical properties of oligodeoxy-nucleotides containing 4'-C- and 5'-C-substituted thymidines. Bioorg Med Chem Lett 9:885-890 (1999).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yu et al. Polymerase recognition of unnatural base pairs. Angew Chem Int Ed Engl 41(20):3841-4 (2002).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Evolution of functional six-nucleotide DNA. J Am Chem Soc 137:6734-6737 (2015).
Zhang et al. Semisynthetic Organisms with Expanded Genetic Codes. Biochemistry 57:2177-2178 (20180.
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).

(-) Cas9
(+) Cas9
UBP Retention (%)
0
20
40
60
80
100
120
GXG 6(T)
GXA 8(T)
GXC 6(T)
GXT 3(G)
AXG 15(T)
AXA 7(T)
AXC 3(T)
AXT 7(A)
CXG 2(G)
CXA 2(A)
CXC 6(T)
CXT 15(A)
TXG 6(T)
TXA 6(A)
TXC 8(G)
TXT 7(T)

Fig. 8B

| pUCX2 UBP Context | UBP retentions (%) | | | | | |
|---|---|---|---|---|---|---|
| | Liquid growth only | Colonies (solid & liquid growth) | | | | |
| | | 1 | 2 | 3 | 4 | 5 |
| GXA | 91 | 35 | 33 | 31 | 29 | 1 |
| GXC | 84 | 89 | 81 | 94 | 82 | 1 |
| GXT | 83 | 88 | 97 | 1 | 50 | 97 |
| AXG | 67 | 6 | 1 | 17 | 8 | |
| AXA | 91 | 47 | 47 | 26 | 57 | 43 |
| AXC | 83 | 0 | 92 | 92 | | |
| AXT | 91 | 80 | 70 | 71 | 94 | 1 |
| TXA | 80 | 1 | 0 | 1 | 1 | 22 |
| TXT | 82 | 62 | 74 | 85 | 87 | 82 |

Fig. 9B

| $N_3$ \ $N_1$ | dC | dT | dA | dG | dTPT3 | dNaM |
|---|---|---|---|---|---|---|
| G | 20 ± 7% (100%) | 1 ± 1% (5%) | 1 ± 1% (5%) | 5 ± 4% (25%) | 3 ± 3% (15%) | 1 ± 1% (5%) |
| A | 11 ± 2% (22%) | 51 ± 6% (100%) | 38 ± 9% (75%) | 11 ± 2% (22%) | 21 ± 3% (41%) | 51 ± 6% (100%) |
| U | 8 ± 2% (50%) | 1 ± 1% (6%) | 16 ± 3% (100%) | 16 ± 4% (100%) | 3 ± 1% (8%) | 8 ± 5% (50%) |
| C | 3 ± 4% (6%) | 31 ± 7% (65%) | 25 ± 8% (52%) | 19 ± 7% (40% | 15 ± 5% (31%) | 48 ± 23% (100%) |

DNA target: CTGGTCCTACCCGTGGT$N_1$GGTCC
sgRNA template: GACCAGGATGGGCACCA$N_3$CC

| Guide RNA | Sequence |
|---|---|
| hEGFP | GACCAGGAUGGGCACCACCC |
| TK1-A | GUUGUGUGGAAAUGUGAG |
| TK1-A/Δ | 1) GUUGUGUGGAAAUGUGAG<br>2) UGUUGUGUGGAAUGUGAG |

DNA Target: GUATGTTGTGTGGAAXTGTGAG

Fig. 11

| pAIO UBP Context | Sequence | Guides (N/Δ) | UBP retentions (%) in YZ3 (-Cas9) | | | | | | | | UBP retentions (%) in YZ4 (+Cas9) | | | | | | |
|---|---|---|---|---|---|---|---|---|---|---|---|---|---|---|---|---|---|
| | | | Colonies | | | | | | | | [IPTG] | Colonies | | | | | |
| | | | 1 | 2 | 3 | 4 | 5 | 6 | 7 | 8 | μM | 1 | 2 | 3 | 4 | 5 | 6 |
| GXG | TCACACAATGTA**GXG**ATCACGG | T/Δ | 59 | 23 | 40 | 57 | | | | | 50 | 103 | 103 | 103 | | | |
| GXA | ACCAGGATGG**GXA**CCACCCCGG | T/Δ | 36 | 90 | 90 | 83 | | | | | 10 | 94 | 102 | 103 | 95 | 88 | 98 |
| GXC | TCACACAATGTA**GXC**ATCACGG | T/Δ | 98 | 97 | 102 | 88 | 65 | 96 | 92 | | 10 | 95 | 97 | 106 | | | |
| GXT | ACCAGGATGGGCACC**AYC**CCGG | G/Δ | 111 | 97 | 115 | 113 | | | | | 25 | 115 | 113 | 114 | | | |
| AXG | ACC**AXG**ATGGGCACCACCCCGG | T/Δ | 3 | 13 | 13 | | | | | | 50 | 107 | 106 | 105 | 109 | 105 | |
| AXA | TCACACAATGT**AXA**GATCACGG | T/Δ | 96 | 91 | 91 | | | | | | 50 | 104 | 103 | 101 | 98 | 76 | |
| AXC | ACCAGGATGGGCACC**AXC**CCGG | T/Δ | 43 | 49 | 72 | 70 | | | | | 0 | 95 | 96 | 96 | | | |
| AXT | TGTTGTGTGGA**AYT**GTGAGCGG | A/Δ | 92 | 92 | 89 | 93 | 85 | 84 | 100 | | 50 | 103 | 103 | 105 | 105 | 102 | 99 |
| CXG | TTGTCACTACTCTGAC**CYG**CGG | G/Δ | 2 | 2 | 6 | 13 | 7 | 14 | 4 | 12 | 50 | 6 | 16 | 23 | 1 | | |
| CXA | TTGTCACTACTCTGAC**CXA**GGG | A/Δ | 1 | 5 | 10 | 0 | 9 | 11 | | | 50 | 8 | 3 | 16 | 10 | 7 | |
| CXC | TCACACAATGTA**CXC**ATCACGG | T/Δ | 16 | 21 | 12 | | | | | | 50 | 66 | 95 | 77 | | | |
| CXT | ACC**AYG**ATGGGCACCACCCCGG | A/Δ | 84 | 73 | 72 | 69 | | | | | 50 | 106 | 112 | 88 | | | |
| TXG | TCACACAATGTA**TXG**ATCACGG | T/Δ | 13 | 20 | 12 | 17 | | | | | 50 | 117 | 86 | 114 | | | |
| TXA | TCACACAATGTA**TYA**ATCACGG | A/Δ | 54 | 79 | 78 | | | | | | 50 | 101 | 104 | 97 | | | |
| TXC | ACCAGGATGG**GYA**CCACCCCGG | G/Δ | 43 | 36 | 68 | | | | | | 10 | 101 | 104 | 100 | | | |
| TXT | ATTCACAATAC**TXT**CTTTAAGG | T/Δ | 104 | 111 | 103 | 96 | | | | | 0 | 115 | 114 | 109 | | | |

Fig. 12

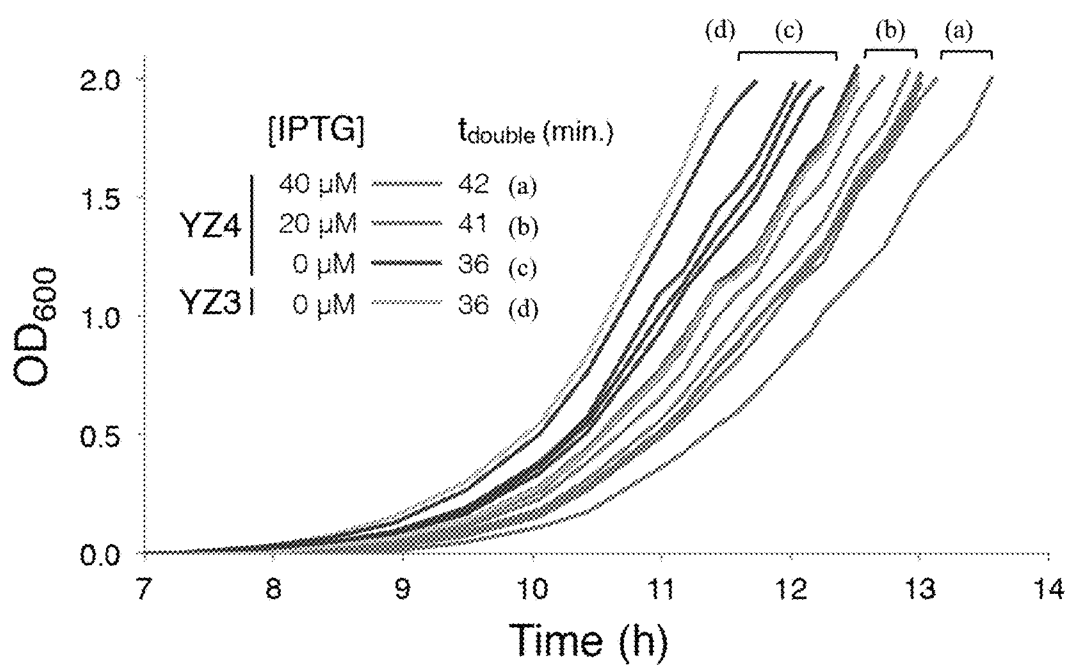

NUCLEOSIDE TRIPHOSPHATE TRANSPORTER AND USES THEREOF

CROSS-REFERENCE

This application is a continuation of U.S. application Ser. No. 16/546,100 filed Aug. 20, 2019, which is a continuation of U.S. application Ser. No. 16/312,901 filed Dec. 21, 2018, which is a National Stage Entry of PCT/US2017/039133 filed Jun. 23, 2017, which claims the benefit of U.S. Provisional Application No. 62/354,650 filed Jun. 24, 2016. Each of the aforementioned applications are incorporated by reference herein in their entireties, and each is hereby expressly made a part of this specification.

STATEMENT OF GOVERNMENT LICENSE RIGHTS

This invention was made with government support under grant number GM060005 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 31, 2020, is named "46085707303 SL.txt" and is 101,256 bytes in size.

BACKGROUND OF THE DISCLOSURE

Oligonucleotides and their applications have revolutionized biotechnology. However, the oligonucleotides including both DNA and RNA each includes only the four natural nucleotides of adenosine (A), guanosine (G), cytosine (C), thymine (T) for DNA, and the four natural nucleotides of adenosine (A), guanosine (G), cytosine (C), and uridine (U) for RNA, and which significantly restricts the potential functions and applications of the oligonucleotides.

The ability to sequence-specifically synthesize/amplify oligonucleotides (DNA or RNA) with polymerases, for example by PCR or isothermal amplification systems (e.g., transcription with T7 RNA polymerase), has revolutionized biotechnology. In addition to all of the potential applications in nanotechnology, this has enabled a diverse range of new technologies such as the in vitro evolution via SELEX (Systematic Evolution of Ligands by Exponential Enrichment) of RNA and DNA aptamers and enzymes. See, for example, Oliphant A R, Brandl C J & Struhl K (1989), Defining the sequence specificity of DNA-binding proteins by selecting binding sites from random-sequence oligonucleotides: analysis of yeast GCN4 proteins, *Mol. Cell Biol.,* 9:2944-2949; Tuerk C & Gold L (1990), Systematic evolution of ligands by exponential enrichment: RNA ligands to bacteriophage T4 DNA polymerase, *Science,* 249:505-510; Ellington A D & Szostak J W (1990), In vitro selection of RNA molecules that bind specific ligands, *Nature,* 346:818-822.

In some aspects, these applications are restricted by the limited chemical/physical diversity present in the natural genetic alphabet (the four natural nucleotides A, C, G, and T in DNA, and the four natural nucleotides A, C, G, and U in RNA).

SUMMARY OF THE DISCLOSURE

Disclosed herein, in certain embodiments, is an isolated and modified nucleoside triphosphate transporter from *Phaeodactylum tricornutum* (PtNTT2) comprising a deletion, wherein the isolated and modified nucleoside triphosphate transporter is obtained from an engineered cell. In some embodiments, the deletion is a terminal deletion or an internal deletion. In some embodiments, the deletion is a terminal deletion. In some embodiments, the deletion is an internal deletion. In some embodiments, the terminal deletion is a N-terminal deletion, a C-terminal deletion, or a deletion of both termini. In some embodiments, the terminal deletion is a N-terminal deletion. In some embodiments, the deletion comprises about 5, 10, 15, 20, 22, 25, 30, 40, 44, 50, 60, 66, 70, or more amino acid residues. In some embodiments, the isolated and modified nucleoside triphosphate transporter comprises a deletion of about 5, 10, 15, 20, 22, 25, 30, 40, 44, 50, 60, 66, 70, or more amino acid residues at the N-terminus. In some embodiments, the isolated and modified nucleoside triphosphate transporter comprises a deletion of about 66 amino acid residues at the N-terminus. In some embodiments, the isolated and modified nucleoside triphosphate transporter comprises at least 80%, 85%, 90%, 95%, 96%, 97%, 98%, or 99% sequence identity sequence identity to SEQ ID NO: 4. In some embodiments, the isolated and modified nucleoside triphosphate transporter comprises 100% sequence identity to SEQ ID NO: 4. In some embodiments, the isolated and modified nucleoside triphosphate transporter comprises at least 80%, 85%, 90%, 95%, 96%, 97%, 98%, or 99% sequence identity to SEQ ID NO: 6. In some embodiments, the isolated and modified nucleoside triphosphate transporter comprises 100% sequence identity to SEQ ID NO: 6. In some embodiments, the isolated and modified nucleoside triphosphate transporter comprises at least 80%, 85%, 90%, 95%, 96%, 97%, 98%, or 99% sequence identity to SEQ ID NO: 8. In some embodiments, the isolated and modified nucleoside triphosphate transporter comprises 100% sequence identity to SEQ ID NO: 8. In some embodiments, the engineered cell comprises a prokaryotic cell. In some embodiments, the engineered cell is *E. coli.*

Disclosed herein, in certain embodiments, is a nucleic acid molecule encoding an isolated and modified nucleoside triphosphate transporter described above.

Disclosed herein, in certain embodiments, is use of a modified nucleoside triphosphate transporter described above for the incorporation of an unnatural triphosphate during the synthesis of a nucleic acid molecule.

Disclosed herein, in certain embodiments, is an engineered cell comprising a first nucleic acid molecule encoding a modified nucleoside triphosphate transporter from *Phaeodactylum tricornutum* (PtNTT2). In some embodiments, the nucleic acid of the modified nucleoside triphosphate transporter is incorporated in the genomic sequence of the engineered cell. In some embodiments, the engineered cell comprises a plasmid comprising the modified nucleoside triphosphate transporter. In some embodiments, the modified nucleoside triphosphate transporter is a codon optimized nucleoside triphosphate transporter from *Phaeodactylum tricornutum*. In some embodiments, the modified nucleoside triphosphate transporter comprises a deletion. In some embodiments, the deletion is a terminal deletion or an internal deletion. In some embodiments, the deletion is a N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the isolated and modified nucleoside triphosphate transporter comprises at least 80%, 85%, 90%, 95%, 96%, 97%, 98%, or 99% sequence identity sequence identity to SEQ ID NO: 4. In some embodiments, the isolated and modified nucleoside triphosphate transporter comprises 100% sequence identity to SEQ ID NO: 4. In some embodiments, the isolated and modified nucleoside triphosphate transporter comprises at least 80%, 85%, 90%, 95%, 96%, 97%, 98%, or 99% sequence identity to SEQ ID NO: 6. In some embodiments, the isolated and modified nucleoside triphosphate transporter comprises 100% sequence identity to SEQ ID NO: 6. In some embodiments, the isolated and modified nucleoside triphosphate transporter comprises at least 80%, 85%, 90%, 95%, 96%, 97%, 98%, or 99% sequence identity to SEQ ID NO: 8. In some embodiments, the isolated and modified nucleoside triphosphate transporter comprises 100% sequence identity to SEQ ID NO: 8. In some embodiments, the modified nucleoside triphosphate transporter is under the control of a promoter selected from an *E. coli* promoter or a phage promoter. In some embodiments, the promoter is selected from $P_{bla}$, $P_{lac}$, $P_{lacUV5}$, $P_{H207}$, $P_{\lambda}$, $P_{tac}$, or $P_{N25}$. In some embodiments, the modified nucleoside triphosphate transporter is under the control of promoter $P_{lacUV5}$. In some embodiments, the modified nucleoside triphosphate transporter is under the control of a promoter from a lac operon. In some embodiments, the modified nucleoside triphosphate transporter is encoded within a pSC plasmid. In some embodiments, the modified nucleoside triphosphate transporter decreases doubling time of the engineered cell. In some embodiments, the modified nucleoside triphosphate transporter enables unnatural base pair retention of about 50%, 60%, 70%, 80%, 90%, 95%, 99% or more. In some embodiments, the engineered cell further comprises a second nucleic acid molecule encoding a Cas9 polypeptide or variants thereof, a third nucleic acid molecule encoding a single guide RNA (sgRNA) comprising a crRNA-tracrRNA scaffold; and a fourth nucleic acid molecule comprising an unnatural nucleotide. In some embodiments, the second nucleic acid molecule, the third nucleic acid molecule, and the fourth nucleic acid molecule are encoded in one or more plasmids. In some embodiments, the sgRNA encoded by the third nucleic acid molecule comprises a target motif that recognizes a modification at the unnatural nucleotide position within the fourth nucleic acid molecule. In some embodiments, the modification at the unnatural nucleotide position within the third nucleic acid molecule generates a modified third nucleic acid molecule. In some embodiments, the modification is a substitution. In some embodiments, the modification is a deletion. In some embodiments, the modification is an insertion. In some embodiments, the sgRNA encoded by the third nucleic acid molecule further comprises a protospacer adjacent motif (PAM) recognition element. In some embodiments, the PAM element is adjacent to the 3' terminus of the target motif. In some embodiments, the combination of Cas9 polypeptide or variants thereof and sgRNA modulates replication of the modified fourth nucleic acid molecule. In some embodiments, the combination of Cas9 polypeptide or variants thereof, sgRNA and the modified nucleoside triphosphate transporter modulates replication of the modified fourth nucleic acid molecule. In some embodiments, the combination of Cas9 polypeptide or variants thereof, sgRNA and the modified nucleoside triphosphate transporter decreases the replication rate of the modified fourth nucleic acid molecule by about 80%, 85%, 95%, 99%, or higher. In some embodiments, the production of the fourth nucleic acid molecule in the engineered cell increases by about 50%, 60%, 70%, 80%, 90%, 95%, 96%, 97%, 98%, 99%, or higher. In some embodiments, the Cas9 polypeptide or variants thereof generate a double-stranded break. In some embodiments, the Cas9 polypeptide is a wild-type Cas9. In some embodiments, the unnatural nucleotide comprises an unnatural base selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyl adenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, 0-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), 5-fluorouracil, 5-bromouracil, 5-chlorouracil, 5-iodouracil, hypoxanthine, xanthine, 4-acetyl cytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the unnatural base is selected from the group consisting of

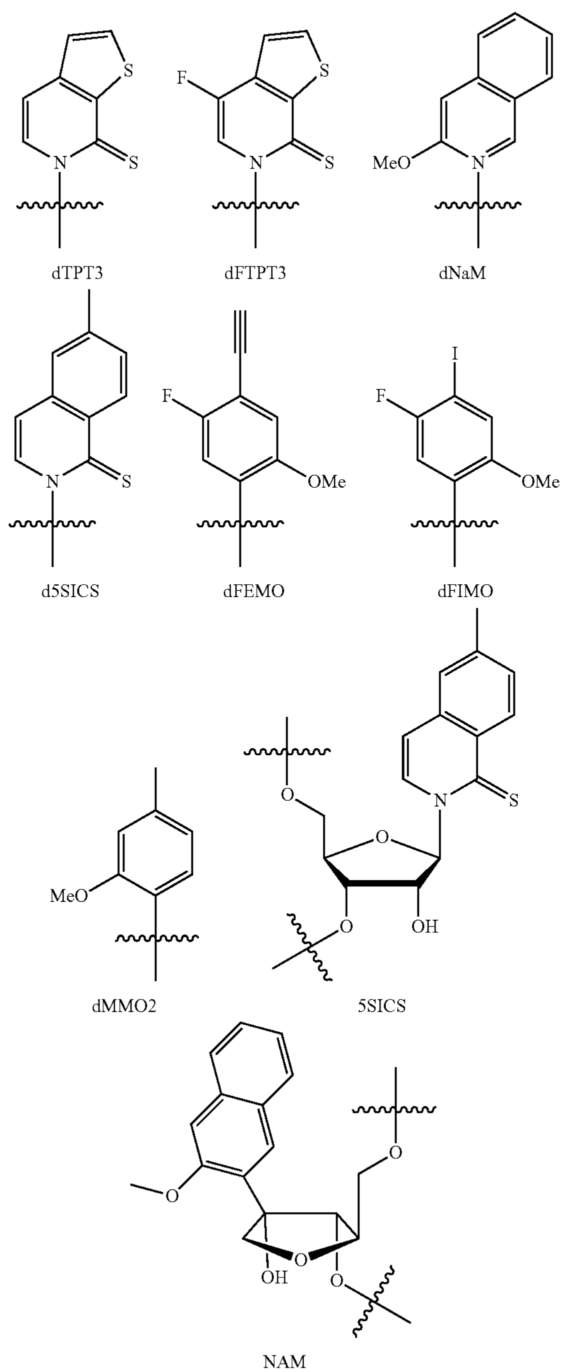

In some embodiments, the unnatural nucleotide further comprises an unnatural sugar moiety. In some embodiments, the unnatural sugar moiety is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'-$O(CH_2)_2O$ $CH_3$ wherein the alkyl, alkenyl and alkynyl may be substituted or unsubstituted $C_1$-$C_{10}$, alkyl, $C_2$-$C_{10}$alkenyl, $C_2$-$C_{10}$alkynyl, —$O[(CH_2)_nO]mCH_3$, —$O(CH_2)_nOCH_3$, —$O(CH_2)_nNH_2$, —$O(CH_2)_nCH_3$, —$O(CH_2)_n$—$ONH_2$, and —$O(CH_2)_nON[(CH_2)_n CH_3)]2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, the unnatural nucleotide further comprises an unnatural backbone. In some embodiments, the unnatural backbone is selected from the group consisting of a phosphorothioate, chiral phosphorothioate, phosphorodithioate, phosphotriester, aminoalkylphosphotriester, $C^1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates. In some embodiments, the sgRNA has less than about 20%, 15%, 10%, 5%, 3%, 1%, or less off-target binding rate. In some embodiments, the engineered cell further comprises an additional nucleic acid molecule that encodes an additional single guide RNA (sgRNA) comprising a crRNA-tracrRNA scaffold. In some embodiments, the engineered cell is a semi-synthetic organism.

Disclosed herein, in certain embodiments, is an in vivo method of increasing the production of a nucleic acid molecule containing an unnatural nucleotide comprising an engineered cell described above.

Disclosed herein, in certain embodiments, is a nucleic acid molecule containing an unnatural nucleotide produced by an engineered cell described above.

Disclosed herein, in certain embodiments, is an isolated and purified plasmid comprising a nucleic acid molecule encoding a modified nucleoside triphosphate transporter from *Phaeodactylum tricornutum* (PtNTT2); and a promoter region selected from a pSC plasmid or lacZYA locus. In some embodiments, the modified nucleoside triphosphate transporter is a codon optimized nucleoside triphosphate transporter from *Phaeodactylum tricornutum*. In some embodiments, the modified nucleoside triphosphate transporter comprises a deletion. In some embodiments, the deletion is a terminal deletion or an internal deletion. In some embodiments, the deletion is a N-terminal truncation, a C-terminal truncation, or a truncation of both termini. In some embodiments, the modified nucleoside triphosphate transporter comprises a deletion of about 5, 10, 15, 20, 22, 25, 30, 40, 44, 50, 60, 66, 70, or more amino acid residues. In some embodiments, the modified nucleoside triphosphate transporter comprises a deletion of about 5, 10, 15, 20, 22, 25, 30, 40, 44, 50, 60, 66, 70, or more amino acid residues at the N-terminus. In some embodiments, the modified nucleoside triphosphate transporter comprises a deletion of about 66 amino acid residues at the N-terminus. In some embodiments, the isolated and modified nucleoside triphosphate transporter comprises at least 80%, 85%, 90%, 95%, 96%, 97%, 98%, or 99% sequence identity sequence identity to SEQ ID NO: 4. In some embodiments, the isolated and modified nucleoside triphosphate transporter comprises 100% sequence identity to SEQ ID NO: 4. In some embodiments, the isolated and modified nucleoside triphosphate transporter comprises at least 80%, 85%, 90%, 95%, 96%, 97%, 98%, or 99% sequence identity to SEQ ID NO: 6. In some embodiments, the isolated and modified nucleoside triphosphate transporter comprises 100% sequence identity to SEQ ID NO: 6. In some embodiments, the isolated and modified nucleoside triphosphate transporter comprises at least 80%, 85%, 90%, 95%, 96%, 97%, 98%, or 99% sequence identity to SEQ ID NO: 8. In some embodiments, the isolated and modified nucleoside triphosphate transporter comprises 100% sequence identity to SEQ ID NO: 8. In some embodiments, the promoter region is selected from $P_{bla}$, $P_{lac}$, $P_{lacUV5}$, $P_{H207}$, $P_{\lambda}$, $P_{tac}$, or $P_{N25}$. In some embodiments, the promoter region is selected from $P_{lacI}$, $P_{bla}$, or $P_{lac}$. In some embodiments, the plasmid is a prokaryotic plasmid.

Disclosed herein, in certain embodiments, is an in vivo method of increasing the production of a nucleic acid molecule containing an unnatural nucleotide comprising incubating a cell with an isolated and purified plasmid described above.

Disclosed herein, in certain embodiments, is a kit comprising an isolated and modified nucleoside triphosphate transporter described above.

Disclosed herein, in certain embodiments, is a kit comprising an engineered cell described above.

Disclosed herein, in certain embodiments, is a kit comprising an isolated and purified plasmid described above.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows the chemical structure of the dNaM-d5SICS and dNaM-dTPT3 UBPs compared to the natural dC-dG base pair. FIG. 1B shows comparison of fitness and [α-$^{32}$P]-dATP uptake in DM1 and the various constructed strains: pCDF and inducible PtNTT2(1-575) (gray); pSC and constitutive PtNTT2(66-575) (blue); integrated and constitutive PtNTT2(66-575) (green). Open triangles denote corresponding control strains without PtNTT2. pCDF plasmids are in *E. coli* C41(DE3); pSC plasmids and integrants are in *E. coli* BL21(DE3). All PtNTT2 strains are non-codon optimized for plasmid-based expression and codon-optimized for chromosomal expression unless otherwise indicated. r.d.0=relative decay units. Error bars represent s.d. of the mean, n=3 cultures grown and assayed in parallel; the error bars on some data points are smaller than their marker.

FIG. 2A shows UBP retentions of plasmids pUCX1, pUCX2, and pBRX2 in strains DM1 and YZ3. Error bars represent s.d. of the mean, n=4 transformations for pUCX1 and pUCX2, n=3 for DM1 pBRX2 and n=5 for YZ3 pBRX2. FIG. 2B shows UBP retentions of pUCX2 variants, wherein the UBP is flanked by all possible combinations of natural nucleotides (NXN, where N=G, C, A, or T and X=NaM), in strain YZ3 grown in media supplemented with either dNaMTP and d5SICSTP (grey bars) or dNaMTP and dTPT3TP (black bars).

FIG. 3A illustrates the model for Cas9-mediated immunity to UBP loss. FIG. 3B shows UBP retentions of pUCX2 variants in strain YZ2 with a pCas9 plasmid that expresses a non-target sgRNA (gray) or an on-target sgRNA (black). Error bars represent s.d. of the mean, n=3 transformations for all sequences except on-target CXA and CXG, where n=5. FIG. 3C shows UBP retentions of pAIO plasmids in strain YZ3 (gray), which does not express Cas9, or in strain YZ4 (black) with expression of Cas9. In FIG. 3B and FIG. 3C, the nucleotides immediately flanking X=NaM are indicated, as is distance to the PAM. (N) denotes the nucleotide N in the sgRNA that targets a substitution mutation of the UBP; all pCas9 and pAIO plasmids also express an sgRNA targeting the deletion mutation. Error bars represent s.d. of the mean, n≥3 colonies; see FIG. 11 for exact values of n, sequences, and IPTG concentrations used to induced Cas9 in YZ4.

FIG. 5A and FIG. 5D show uptake of [α-$^{32}$P]-dATP. Error bars represent s.d. of the mean, n=3 cultures. r.d.u.=relative decay units, which corresponds to the total number of radioactive counts per minute normalized to the average $OD_{600}$ across the 1 h window of uptake, with the uptake of C41(DE3) pCDF-1b PtNTT2(1-575) (i.e. DM1) induced with 1000 μM IPTG set to 1. Deletion of the N-terminal signal sequences drastically reduces uptake activity in C41(DE3), but activity can be restored with higher levels of expression in BL21(DE3). FIG. 5B shows growth curves of C41(DE3) strains. Induction of PtNTT2(1-575) is toxic. FIG. 5C shows growth curves of BL21(DE3) strains. Induction of T7 RNAP in BL21(DE3) is toxic (see empty vector traces), which masks the effect of deleting the N-terminal signal sequences of PtNTT2 on cell growth. FIG. 5E shows growth curves of plasmid-based transporter strains. Strains are expressing non codon-optimized (co) PtNTT2(66-575) unless otherwise indicated. FIG. 5F shows growth curves of chromosomally-integrated transporter strains. Strains are expressing codon-optimized PtNTT2(66-575) unless otherwise indicated. Strain YZ4 also contains a chromosomally integrated Cas9 gene.

FIG. 7A shows biotin shift assay scheme and representative gels for FIG. 2*b*. Input plasmid refers to the ligation product used to transform the SSO. * denotes a band whose mobility does not change in the absence of streptavidin (data not shown) and does not appear in any samples from clonally-derived cultures (data not shown). The band likely corresponds to a fully natural plasmid derived from non-specific priming during the PCR used to generate the insert for ligation, and is present in very small quantities in the input plasmid, but is enriched for during replication in vivo by competition against challenging UBP sequences. Such bands are not included in the calculation of retention. FIG. 7B illustrates representative gels for FIG. 4. Each lane (excluding the oligonucleotide controls) corresponds to a pAIO2X plasmid sample isolated from a clonally-derived YZ4 culture, grown with the IPTG concentration indicated, after an estimated 108 cell doublings in liquid culture (point 7 in FIG. 4). Each plasmid sample is split and analyzed in parallel biotin shift reactions that assay the UBP content at the gfp and serT loci (red and blue primers, respectively). The 80 μM samples are not shown in the plot for FIG. 4.

FIG. 8A-FIG. 8B show additional characterization of UBP propagation. FIG. 8A shows growth curves for the experiments shown in FIG. 2*a*. YZ3 and DM1 (induced with 1 mM IPTG) were transformed with the indicated UBP-containing plasmids, or their corresponding fully natural controls, and grown in media containing dNaMTP and d5SICSTP. Each line represents one transformation and subsequent growth in liquid culture. The x-axis represents time spent in liquid culture, excluding the 1 h of recovery following electroporation (see Methods). Growth curves terminate at the $OD_{600}$ at which cells were collected for plasmid isolation and analysis of UBP retention. Staggering of the curves along the x-axis for replicates within a given strain and plasmid combination is likely due to minor variability in transformation frequencies between transformations (and thus differences in the number of cells inoculated into each culture), whereas differences in slope between curves indicate differences in fitness. Growth of YZ3 is comparable between all three UBP-containing plasmids (and between each UBP-containing plasmid with its respective natural control), whereas growth of DM1 is impaired by the UBP-containing plasmids, especially for pUCX1 and pUCX2. FIG. 8B shows retentions of gfp pUCX2 variants propagated in YZ3 by transformation, plating on solid media, isolation of single colonies, and subsequent inoculation and growth in liquid media, in comparison to retentions from plasmids propagated by transformation and growth of YZ3 in liquid media only. Cells were plated from the same transformations described in FIG. 2*b*. Solid and liquid media both contained dNaMTP and dTPT3TP. Cells were harvested at $OD_{600}$~1. Five colonies were inoculated for each of the pUCX2 variants indicated, but some colonies failed to grow (indicated by a blank space in the table). Retentions for samples isolated from transformants grown solely in liquid media were assayed from the same samples shown in FIG. 2*b*, but were assayed and normalized to an oligonucleotide control in parallel with the plated transformant samples to facilitate comparisons in retention. See Methods for additional details regarding UBP retention normalization. For samples with near zero shift, we cannot determine whether the UBP was completely lost in vivo or if the sample came from a colony that was transformed with a fully natural plasmid (some of which arises during plasmid construction, specifically during the PCR used to generate the UBP-containing insert).

FIG. 9A-FIG. 9B illustrate effect of dNaM-dTPT3 on Cas9-mediated cleavage of DNA in vitro. Cas9-mediated in vitro cleavage was assessed for six DNA substrates, wherein the third base pair upstream of the PAM was either one of the four natural base pairs or the UBP (in both strand contexts). The four sgRNAs that are complementary to each natural template were prepared by in vitro transcription with T7 RNAP. To account for differences in sgRNA activity and/or minor variations in preparation, a relative percent maximal cleavage for each sgRNA vs all six DNA substrates is shown in parentheses. Values represent means±1 s.d. (n=3 technical replicates). In several cases, the presence of an unnatural nucleotide significantly reduced cleavage compared to DNA complementary to the sgRNA. This data suggests that Cas9 programmed with sgRNA(s) complementary to one or more of the natural sequences would preferentially degrade DNA that had lost the UBP. FIG. 9B discloses SEQ ID NOS 201 and 202, respectively, in order of appearance.

FIG. 10A shows sgRNA sequences used to enhance retention of the UBP (SEQ ID NOS 203, 204, 204, 205, and 206, respectively, in order of appearance). FIG. 10B shows UBP retention for pUCX2 TK1 is enhanced by targeting Cas9 to the major mutation (dTPT3→dA). As cells continue to grow in the absence of correct sgRNAs targeting mutations, UBP retention declines. Error bars represent s.d. of the mean, n=3 transformations. In FIG. 10A and FIG. 10B, hEGFP is a non-target sgRNA. FIG. 10C shows Sanger sequencing chromatogram illustrating mutation of dNaM to dT in the absence of an sgRNA to target Cas9 nuclease activity (SEQ ID NOS 207 and 208, respectively, in order of appearance). FIG. 10D shows Sanger sequencing chromatogram illustrating that loss of retention in the presence of Cas9 and a targeting sgRNA (TK1-A) is due to growth of cells with plasmids possessing a single base pair mutation. UBP-containing species were depleted before sequencing. FIG. 10D discloses SEQ ID NOS 207 and 208, respectively, in order of appearance.

FIG. 11 shows Cas9 NXN sequences. 22-nt of each UBP-containing sequence examined in FIG. 3 is shown above. X=dNaM, Y=dTPT3 (SEQ ID NOS 209-224, respectively, in order of appearance). The sequence of the sgRNA targeting the substitution mutation of the UBP (N) is the 18-nt sequence 5' to the NGG PAM with X or Y replaced by the natural nucleotide indicated. The sequence of the sgRNA targeting the deletion mutation of the UBP (Δ) is the 19-nt sequence 5' to the NGG PAM without X or Y. YZ3 experiments were performed without IPTG. Retentions shown in FIG. 3C are averaged from the values and number of colonies indicated here.

FIG. 12 shows growth curves of YZ4 replicating pAIO2X. Growth curves for the first dilution-regrowth (point 2) in FIG. 4. Curves terminate at the $OD_{600}$ at which cultures were collected for both plasmid isolation and dilution for the next regrowth. Doubling times are calculated from the timepoints collected between $OD_{600}$ 0.1-1.0 for each curve and averaged for each strain and/or IPTG condition.

DETAILED DESCRIPTION OF THE DISCLOSURE

Figure 1A:
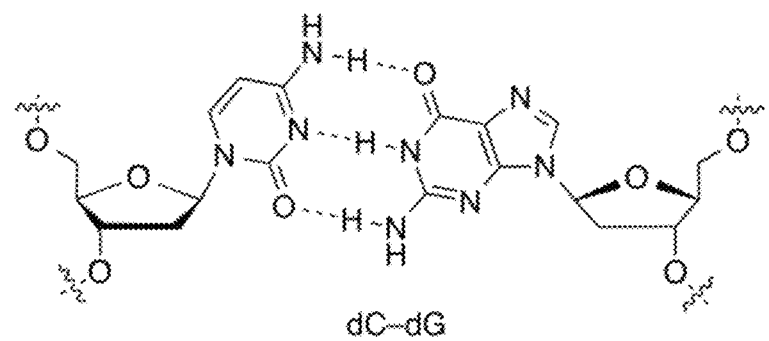
FIG. 1A-FIG. 1B illustrate UBPs and transporter optimization.
Figure 1A:
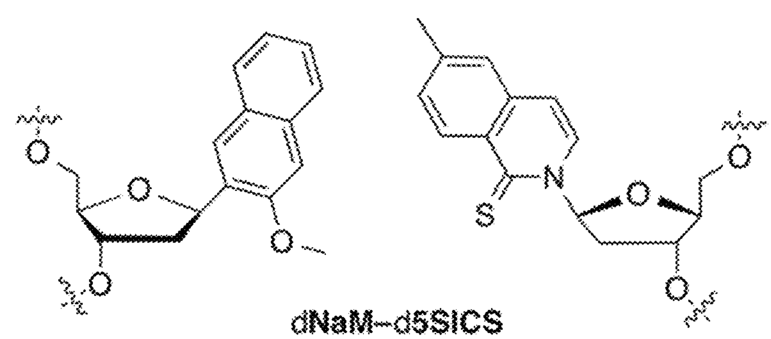
Figure 1A:
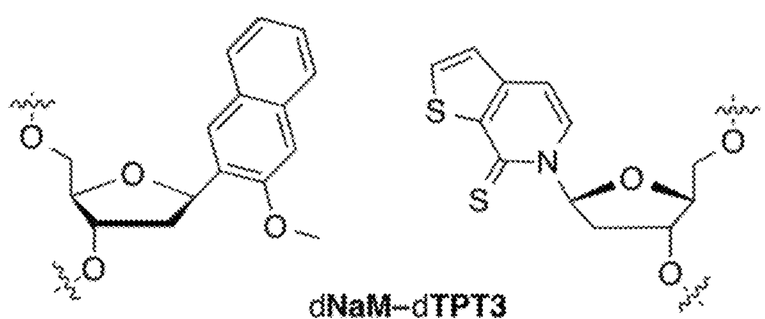

Nucleosides are hydrophilic molecules which requires transport proteins for permeation of cell membranes. Nucleoside transporters (NTs) are a group of membrane transport proteins that facilitate crossing of the nucleosides through cell membranes and vesicles. In some cases, there are two types of nucleoside transporters, concentrative nucleoside transporters which drives a concentrative process by electrochemical gradient, and equilibrative nucleoside transporters which drives an equilibrative bidirectional process by chemical gradient. In some instances, a nucleoside transporter further encompasses a nucleoside triphosphate transporter.

Natural nucleosides comprise adenine, guanine, thymine, uracil, and cytosine; and are recognized by nucleotide transporters for permeation of cell membranes. Unnatural nucleosides, in some cases, are either not recognized by endogenous nucleotide transporters or are recognized but the efficiency of transport is low.

In some embodiments, described herein are modified nucleotide transporters that recognize and facilitate transport of unnatural nucleic acids into a cell. In some instances, the modified nucleotide transporter enhances import of unnatural nucleic acids into a cell relative to an endogeneous nucleotide transporter. In some cases, the modified nucleotide transporter increases unnatural nucleic acid retention within a cell. In additional cases, the modified nucleotide transporter minimizes toxicity due to its expression, and optionally improves cell doubling time and fitness relative to a cell in the absence of the transporter.

Nucleoside Triphosphate Transporters

In certain embodiments, described herein are modified nucleoside triphosphate transporters for transporting unnatural nucleic acids into a cell. In some instances, the modified nucleoside triphosphate transporter is from *Phaeodactylum tricornutum*(PtNTT2). In some instances, the modified nucleoside triphosphate transporter further comprises a deletion. In some cases, the deletion is a terminal deletion (e.g., a N-terminal deletion or a C-terminal deletion) or is an internal deletion.

In some embodiments, described herein is an isolated and modified modified nucleoside triphosphate transporter from *Phaeodactylum tricornutum* (PtNTT2) comprising a deletion. In some instances, the deletion comprises about 5, 10, 15, 20, 22, 25, 30, 40, 44, 50, 60, 66, 70, 80, 90, or more amino acid residues. In some instances, the deletion comprises about 5, 10, 15, 20, 22, 25, 30, 40, 44, 50, 60, 66, 70, or more amino acid residues. In some cases, the modified modified nucleoside triphosphate transporter from *Phaeodactylum tricornutum* (PtNTT2) comprises a deletion of about 5 or more amino acid residues. In some cases, the modified modified nucleoside triphosphate transporter from *Phaeodactylum tricornutum* (PtNTT2) comprises a deletion of about 10 or more amino acid residues. In some cases, the modified modified nucleoside triphosphate transporter from *Phaeodactylum tricornutum* (PtNTT2) comprises a deletion of about 15 or more amino acid residues. In some cases, the modified modified nucleoside triphosphate transporter from *Phaeodactylum tricornutum* (PtNTT2) comprises a deletion of about 20 or more amino acid residues. In some cases, the modified modified nucleoside triphosphate transporter from *Phaeodactylum tricornutum* (PtNTT2) comprises a deletion of about 22 or more amino acid residues. In some cases, the modified modified nucleoside triphosphate transporter from *Phaeodactylum tricornutum* (PtNTT2) comprises a deletion of about 25 or more amino acid residues. In some cases, the modified modified nucleoside triphosphate transporter from *Phaeodactylum tricornutum* (PtNTT2) comprises a deletion of about 30 or more amino acid residues. In some cases, the modified modified nucleoside triphosphate transporter from *Phaeodactylum tricornutum* (PtNTT2) comprises a deletion of about 40 or more amino acid residues. In some cases, the modified modified nucleoside triphosphate transporter from *Phaeodactylum tricornutum* (PtNTT2) comprises a deletion of about 44 or more amino acid residues. In some cases, the modified modified nucleoside triphosphate transporter from *Phaeodactylum tricornutum* (PtNTT2) comprises a deletion of about 50 or more amino acid residues. In some cases, the modified modified nucleoside triphosphate transporter from *Phaeodactylum tricornutum* (PtNTT2) comprises a deletion of about 60 or more amino acid residues. In some cases, the modified modified nucleoside triphosphate transporter from *Phaeodactylum tricornutum* (PtNTT2) comprises a deletion of about 66 or more amino acid residues. In some cases, the modified modified nucleoside triphosphate transporter from *Phaeodactylum tricornutum* (PtNTT2) comprises a deletion of about 70 or more amino acid residues.

In some embodiments, described herein is an isolated and modified modified nucleoside triphosphate transporter from *Phaeodactylum tricornutum* (PtNTT2) comprising a N-terminal deletion. In some instances, the N-terminal deletion comprises about 5, 10, 15, 20, 22, 25, 30, 40, 44, 50, 60, 66, 70, 80, 90, or more amino acid residues. In some instances, the N-terminal deletion comprises about 5, 10, 15, 20, 22, 25, 30, 40, 44, 50, 60, 66, 70, or more amino acid residues. In some cases, the modified modified nucleoside triphosphate transporter from *Phaeodactylum tricornutum* (PtNTT2) comprises a N-terminal deletion of about 5 or more amino acid residues. In some cases, the modified modified nucleoside triphosphate transporter from *Phaeodactylum tricornutum* (PtNTT2) comprises a N-terminal deletion of about 10 or more amino acid residues. In some cases, the modified modified nucleoside triphosphate transporter from *Phaeodactylum tricornutum* (PtNTT2) comprises a N-terminal deletion of about 15 or more amino acid residues. In some cases, the modified modified nucleoside triphosphate transporter from *Phaeodactylum tricornutum* (PtNTT2) comprises a N-terminal deletion of about 20 or more amino acid residues. In some cases, the modified modified nucleoside triphosphate transporter from *Phaeodactylum tricornutum* (PtNTT2) comprises a N-terminal deletion of about 22 or more amino acid residues. In some cases, the isolated and modified modified nucleoside triphosphate transporter from *Phaeodactylum tricornutum* (PtNTT2) comprises a N-terminal deletion of about 25 or more amino acid residues. In some cases, the modified modified nucleoside triphosphate transporter from *Phaeodactylum tricornutum* (PtNTT2) comprises a N-terminal deletion of about 30 or more amino acid residues. In some cases, the modified modified nucleoside triphosphate transporter from *Phaeodactylum tricornutum* (PtNTT2) comprises a N-terminal deletion of about 40 or more amino acid residues. In some cases, the modified modified nucleoside triphosphate transporter from *Phaeodactylum tricornutum* (PtNTT2) comprises a N-terminal deletion of about 44 or more amino acid residues. In some cases, the modified modified nucleoside triphosphate transporter from *Phaeodactylum tricornutum* (PtNTT2) comprises a N-terminal deletion of about 50 or more amino acid residues. In some cases, the modified modified nucleoside triphosphate transporter from *Phaeodactylum tricornutum* (PtNTT2) comprises a N-terminal deletion of about 60 or more amino acid residues. In some cases, the modified modified nucleoside triphosphate transporter from *Phaeodactylum tricornutum* (PtNTT2) comprises a N-terminal deletion of about 66 or more amino acid residues. In some cases, the modified modified nucleoside triphosphate transporter from *Phaeodactylum tricornutum* (PtNTT2) comprises a N-terminal deletion of about 70 or more amino acid residues.

In some embodiments, the isolated and modified nucleoside triphosphate transporter comprises at least 80%, 85%, 90%, 95%, 96%, 97%, 98%, or 99% sequence identity to SEQ ID NO: 4. In some instances, the modified nucleoside triphosphate transporter comprises at least 80% sequence identity to SEQ ID NO: 4. In some instances, the modified nucleoside triphosphate transporter comprises at least 85% sequence identity to SEQ ID NO: 4. In some instances, the modified nucleoside triphosphate transporter comprises at least 90% sequence identity to SEQ ID NO: 4. In some instances, the modified nucleoside triphosphate transporter comprises at least 95% sequence identity to SEQ ID NO: 4. In some instances, the modified nucleoside triphosphate transporter comprises at least 96% sequence identity to SEQ ID NO: 4. In some instances, the modified nucleoside triphosphate transporter comprises at least 97% sequence identity to SEQ ID NO: 4. In some instances, the modified nucleoside triphosphate transporter comprises at least 98% sequence identity to SEQ ID NO: 4. In some instances, the modified nucleoside triphosphate transporter comprises at least 99% sequence identity to SEQ ID NO: 4. In some instances, the modified nucleoside triphosphate transporter comprises 100% sequence identity to SEQ ID NO: 4. In some instances, the modified nucleoside triphosphate transporter consists of 100% sequence identity to SEQ ID NO: 4.

In some embodiments, the isolated and modified nucleoside triphosphate transporter comprises at least 80%, 85%, 90%, 95%, 96%, 97%, 98%, or 99% sequence identity to SEQ ID NO: 6. In some instances, the modified nucleoside triphosphate transporter comprises at least 80% sequence identity to SEQ ID NO: 6. In some instances, the modified nucleoside triphosphate transporter comprises at least 85% sequence identity to SEQ ID NO: 6. In some instances, the modified nucleoside triphosphate transporter comprises at least 90% sequence identity to SEQ ID NO: 6. In some instances, the modified nucleoside triphosphate transporter comprises at least 95% sequence identity to SEQ ID NO: 6. In some instances, the modified nucleoside triphosphate transporter comprises at least 96% sequence identity to SEQ ID NO: 6. In some instances, the modified nucleoside triphosphate transporter comprises at least 97% sequence identity to SEQ ID NO: 6. In some instances, the modified nucleoside triphosphate transporter comprises at least 98% sequence identity to SEQ ID NO: 6. In some instances, the modified nucleoside triphosphate transporter comprises at least 99% sequence identity to SEQ ID NO: 6. In some instances, the modified nucleoside triphosphate transporter comprises 100% sequence identity to SEQ ID NO: 6. In some instances, the modified nucleoside triphosphate transporter consists of 100% sequence identity to SEQ ID NO: 6.

In some embodiments, the isolated and modified nucleoside triphosphate transporter comprises at least 80%, 85%, 90%, 95%, 96%, 97%, 98%, or 99% sequence identity to SEQ ID NO: 8. In some instances, the modified nucleoside triphosphate transporter comprises at least 80% sequence identity to SEQ ID NO: 8. In some instances, the modified nucleoside triphosphate transporter comprises at least 85% sequence identity to SEQ ID NO: 8. In some instances, the modified nucleoside triphosphate transporter comprises at least 90% sequence identity to SEQ ID NO: 8. In some instances, the modified nucleoside triphosphate transporter comprises at least 95% sequence identity to SEQ ID NO: 8. In some instances, the modified nucleoside triphosphate transporter comprises at least 96% sequence identity to SEQ ID NO: 8. In some instances, the modified nucleoside triphosphate transporter comprises at least 97% sequence identity to SEQ ID NO: 8. In some instances, the modified nucleoside triphosphate transporter comprises at least 98% sequence identity to SEQ ID NO: 8. In some instances, the modified nucleoside triphosphate transporter comprises at least 99% sequence identity to SEQ ID NO: 8. In some instances, the modified nucleoside triphosphate transporter comprises 100% sequence identity to SEQ ID NO: 8. In some instances, the modified nucleoside triphosphate transporter consists of 100% sequence identity to SEQ ID NO: 8.

In some embodiments, a modified nucleoside triphosphate transporter described herein has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward the unnatural nucleic acid. In some embodiments, the modified nucleoside triphosphate transporter has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward a natural nucleic acid and/or the unnatural nucleic acid without the modified sugar. In some embodiments, the modified nucleoside triphosphate transporter has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward a natural nucleic acid and/or the unnatural nucleic acid without the modified base. In some embodiments, the modified nucleoside triphosphate transporter has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward a nucleic acid comprising a triphosphate and/or the unnatural nucleic acid without the triphosphate. For example, a modified nucleoside triphosphate transporter can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward the unnatural nucleic acid with a diphosphate or monophosphate, or no phosphate, or a combination thereof.

In some embodiments, a modified nucleoside triphosphate transporter described herein has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward the natural nucleic acid. In some embodiments, the modified nucleoside triphosphate transporter has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward the natural nucleic acid. In some embodiments, the modified nucleoside triphosphate transporter has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type nucleoside triphosphate transporter toward the natural nucleic acid.

In some embodiments, a sequence of a modified nucleoside triphosphate transporter is further modified to improve the expression and cellular activity. In some instances, the codon usage is modified to introduce ribosomal pause sites to slow translation and to improve the targeting of the modified nucleoside triphosphate transporter polypeptide to membrane translocons (Fluman, et al., "mRNA-programmed translation pauses in the targeting of *E. coli* membrane proteins," eLife 2014; 3:e03440). In some instances, modification of one or more transmembrane helices, for example, modification of a first transmembrane helix and/or generating a chimeric transporter comprising a first transmembrane helix of a different protein (e.g., a related transporter) may enhance expression and cellular activities (Marshall, et al., "A link between integral membrane protein expression and simulated integration efficiency," Cell Reports, 16(8): 2169-2177 (2016)). In some instances, an endogenous, a modified, or a heterologous signal peptide is incorporated into the sequence of a modified nucleoside triphosphate transporter to improve expression and cellular activity. In some cases, the signal peptide is optionally linked in-frame with the sequence of the modified nucleoside triphosphate transporter through a linker. In some cases, the linker is a non-cleavable linker. In other cases, the linker is a cleavable linker. Exemplary signal peptides are illustrated in Table 3. In some cases, a signal peptide from Table 3, optionally linked to a linker, is incorporated into the sequence of a modified nucleoside triphosphate transporter described herein.

In some embodiments, the expression of the modified nucleoside triphosphate transporter is tuned through modification of the ribosomal binding site to modulate the rate of the modified nucleoside triphosphate transporter polypeptide's synthesis. See, e.g., Howard, et al., "Automated design of synthetic ribosome binding sites to control protein expression," *Nature Biotechnology* 27: 946-950 (2009); and Mutalik, et al., "Precise and reliable gene expression via standard transcription and translation initiation elements," *Nature Methods* 10: 354-360 (2013).

In some embodiments, the expression of the modified nucleoside triphosphate transporter is modulated by the attachment of a tunable degradation tag. In some instances, a tunable degradation tag comprises a small amino acid sequence that, when fused to a target protein, marks the protein for degradation by a cognate protease in a bacterial cell. Exemplary tunable degradation tag and cognate protease pairs include, but are not limited to, *E. coli* ssrA (ec-ssrA)/*E. coli* Lon (ec-Lon), and *Mesoplasma florma* ssrA (mf-ssrA)/*Mesoplasma florma* Lon (mf-Lon). In some instances, the tunable degradation tag comprises a modified tag that alters expression and/or degradation dynamis relative to an unmodified degradation tag. In some instances, a tunable degradation tag contemplated herein comprises a degradation tag described in PCT Patent Publication WO2014/160025A2. In some instances, a tunable degradation tag contemplated herein comprises a degradation tag described in Cameron, et al., "Tunable protein degradation in bacteria," *Nature Biotechnology* 32: 1276-1281 (2014).

In some embodiments, the expression of the modified nucleoside triphosphate transporter is modulated by the availability of an endogenous or exogenous (e.g. unnatural nucleotide triphosphate or unnatural amino acid) molecule during translation. In some instances, the expression of the modified nucleoside triphosphate transporter is correlated with the copy number of rare codons, in which the rate of a ribosomal read-through of a rare codon modulates translation of the transporter. See, e.g., Wang, et al., "An engineered rare codon device for optimization of metabolic pathways," *Scientific Reports* 6:20608 (2016).

In some instances, a modified nucleoside triphosphate transporter is characterized according to its rate of dissociation from a nucleic acid substrate. In some embodiments, a modified nucleoside triphosphate transporter has a relatively low dissociation rate for one or more natural and unnatural nucleic acids. In some embodiments, a modified nucleoside triphosphate transporter has a relatively high dissociation rate for one or more natural and unnatural nucleic acids. The dissociation rate is an activity of an isolated and modified nucleoside triphosphate transporter that can be adjusted to tune reaction rates in methods set forth herein.

Modified nucleoside triphosphate transporters from native sources or variants thereof can be screened using an assay that detects importation of an unnatural nucleic acid having a particular structure. In one example, the modified nucleoside triphosphate transporters can be screened for the ability to import an unnatural nucleic acid or UBP; e.g., d5SICSTP, dNaMTP, or d5SICSTP-dNaMTP UBP. A NTT, e.g., a heterologous transporter, can be used that displays a modified property for the unnatural nucleic acid as compared to the wild-type transporter. For example, the modified property can be, e.g., $K_m$, $k_{cat}$, $V_{max}$, NTT importation in the presence of an unnatural nucleic acid (or of a naturally occurring nucleotide), average template read-length by a cell with the modified nucleoside triphosphate transporter in the presence of an unnatural nucleic acid, specificity of the transporter for an unnatural nucleic acid, rate of binding of an unnatural nucleic acid, or rate of product release, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the modified nucleoside triphosphate transporter optionally has an increased rate of binding of an unnatural nucleic acid, an increased rate of product release, and/or an increased cell importation rate, as compared to a wild-type transporter.

At the same time, a modified nucleoside triphosphate transporter can import natural nucleic acids, e.g., A, C, G, and T, into cell. For example, a modified nucleoside triphosphate transporter optionally displays a specific importation activity for a natural nucleic acid that is at least about 5% as high (e.g., 5%, 10%, 25%, 50%, 75%, 100% or higher), as a corresponding wild-type transporter. Optionally, the modified nucleoside triphosphate transporter displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type NTT.

Modified nucleoside triphosphate transporters used herein that can have the ability to import an unnatural nucleic acid of a particular structure can also be produced using a directed evolution approach. A nucleic acid synthesis assay can be used to screen for transporter variants having specificity for any of a variety of unnatural nucleic acids. For example, transporter variants can be screened for the ability to import an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant transporter variant. In some embodiments, such an assay is an in vivo assay, e.g., expressing a transporter variant in a cell. Such directed evolution techniques can be used to screen variants of any suitable transporter for activity toward any of the unnatural nucleic acids set forth herein.

Engineered Cells

In some embodiments, described herein is an engineered cell comprising a nucleic acid molecule encoding a modified nucleoside triphosphate transporter. In some instances, the nucleic acid molecule encodes a modified nucleoside triphosphate transporter from *Phaeodactylum tricornutum* (PtNTT2). In some instances, the nucleic acid of the modified nucleoside triphosphate transporter is incorporated in the genomic sequence of the engineered cell.

The engineered cell can be any suitable prokaryote. In some instances, the engineered cell is a Gram negative bacteria. In other instances, the engineered cell is a Gram positive bacteria. Exemplary bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stb12, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

In some instances, the engineered cell comprises a plasmid comprising the modified nucleoside triphosphate transporter. In some cases, the modified nucleoside triphosphate transporter is a codon optimized nucleoside triphosphate transporter from *Phaeodactylum tricornutum.*

In some embodiments, the modified nucleoside triphosphate transporter comprises a deletion. In some cases, the deletion is a terminal deletion (e.g., a N-terminal or a C-terminal deletion). In other cases, the deletion is an internal deletion.

As described above, the modified nucleoside triphosphate transporter comprises a deletion of about 5, 10, 15, 20, 22, 25, 30, 40, 44, 50, 60, 66, 70, or more amino acid residues. In some cases, the deletion is a N-terminal deletion, and the modified nucleoside triphosphate transporter comprises a deletion of about 5, 10, 15, 20, 22, 25, 30, 40, 44, 50, 60, 66, 70, or more amino acid residues at the N-terminus. In some cases, the modified nucleoside triphosphate transporter comprises a deletion of about 66 amino acid residues at the N-terminus.

In some instances, the isolated and modified nucleoside triphosphate transporter comprises at least 80%, 85%, 90%, 95%, 96%, 97%, 98%, or 99% sequence identity sequence identity to SEQ ID NOs: 4, 6, or 8. In some cases, the isolated and modified nucleoside triphosphate transporter comprises at least 80%, 85%, 90%, 95%, 96%, 97%, 98%, or 99% sequence identity sequence identity to SEQ ID NO: 4. In some cases, the isolated and modified nucleoside triphosphate transporter comprises 100% sequence identity to SEQ ID NO: 4. In some cases, the isolated and modified nucleoside triphosphate transporter comprises at least 80%, 85%, 90%, 95%, 96%, 97%, 98%, or 99% sequence identity to SEQ ID NO: 6. In some cases, the isolated and modified nucleoside triphosphate transporter comprises 100% sequence identity to SEQ ID NO: 6. In some cases, the isolated and modified nucleoside triphosphate transporter comprises at least 80%, 85%, 90%, 95%, 96%, 97%, 98%, or 99% sequence identity to SEQ ID NO: 8. In some cases, the isolated and modified nucleoside triphosphate transporter comprises 100% sequence identity to SEQ ID NO: 8.

In some embodiments, the modified nucleoside triphosphate transporter is under the control of a promoter. In some instances, the promoter is derived from an *E. coli* source. In other instances, the promoter is derived from a phage source. Exemplary promoters, include, but are not limited to, $P_{bla}$, $P_{lac}$, $P_{lacUV5}$, $P_{H207}$, $P_{\lambda}$, $P_{tac}$, or $P_{N25}$. In some instances, the promoter replaces the lac operon. In some cases, the modified nucleoside triphosphate transporter is under the control of a promoter selected from $P_{bla}$, $P_{lac}$, $P_{lacUV5}$, $P_{H207}$, $P_{\lambda}$, $P_{tac}$, or $P_{N25}$. In some cases, the modified nucleoside triphosphate transporter is under the control of promoter $P_{lacUV5}$.

In some instances, the modified nucleoside triphosphate transporter is encoded within a pSC plasmid.

In some embodiments, the engineered cell further comprises a second nucleic acid molecule encoding a Cas9 polypeptide or variants thereof, a third nucleic acid molecule encoding a single guide RNA (sgRNA) comprising a crRNA-tracrRNA scaffold; and a fourth nucleic acid molecule comprising an unnatural nucleotide.

The CRISPR/Cas system involves (1) an integration of short regions of genetic material that are homologous to a nucleic acid molecule of interest comprising an unnatural nucleotide, called "spacers", in clustered arrays in the host genome, (2) expression of short guiding RNAs (crRNAs) from the spacers, (3) binding of the crRNAs to specific portions of the nucleic acid molecule of interest referred to as protospacers, and (4) degradation of protospacers by CRISPR-associated nucleases (Cas). In some cases, a Type-II CRISPR system has been described in the bacterium *Streptococcus pyogenes*, in which Cas9 and two non-coding small RNAs (pre-crRNA and tracrRNA (trans-activating CRISPR RNA)) act in concert to target and degrade a nucleic acid molecule of interest in a sequence-specific manner (Jinek et al., "A Programmable Dual-RNA-Guided DNA Endonuclease in Adaptive Bacterial Immunity," Science 337(6096):816-821 (August 2012, epub Jun. 28, 2012)).

In some instances, a CRISPR/Cas system utilizes a Cas9 polypeptide or a variant thereof, Cas9 is a double stranded nuclease with two active cutting sites, one for each strand of the double helix. In some instances, the Cas9 polypeptide or variants thereof generate a double-stranded break. In some cases, the Cas9 polypeptide is a wild-type Cas9. In some instances, the Cas9 polypeptide is an optimized Cas9 for expression in an engineered cell described herein.

In some instances, the two noncoding RNAs are further fused into one single guide RNA (sgRNA). In some instances, the sgRNA comprises a target motif that recognizes a modification at the unnatural nucleotide position within a nucleic acid molecule of interest. In some embodiments, the modification is a substitution, insertion, or deletion. In some cases, the sgRNA comprises a target motif that recognizes a substitution at the unnatural nucleotide position within a nucleic acid molecule of interest. In some cases, the sgRNA comprises a target motif that recognizes a deletion at the unnatural nucleotide position within a nucleic acid molecule of interest. In some cases, the sgRNA comprises a target motif that recognizes an insertion at the unnatural nucleotide position within a nucleic acid molecule of interest.

In some cases, the target motif is between 10 to 30 nucleotides in length. In some instances, the target motif is between 15 to 30 nucleotides in length. In some cases, the target motif is about 11, 12, 13, 14, 15, 16, 17, 18, 19, 20, 21, 22, 23, 24, 25, 26, 27, 28, 29, or 30 nucleotides in length. In some cases, the target motif is about 15, 16, 17, 18, 19, 20, 21, or 22 nucleotides in length.

In some cases, the sgRNA further comprises a protospacer adjacent motif (PAM) recognition element. In some instances, PAM is located adjacent to the 3' terminus of the target motif. In some cases, a nucleotide within the target motif that forms Watson-Crick base pairing with the modification at the unnatural nucleotide position within the nucleic acid molecule of interest is located between 3 to 22, between 5 to 20, between 5 to 18, between 5 to 15, between 5 to 12, or between 5 to 10 nucleotides from the 5' terminus of PAM. In some cases, a nucleotide within the target motif that forms Watson-Crick base pairing with the modification at the unnatural nucleotide position within the nucleic acid molecule of interest is located about 3, 4, 5, 6, 7, 8, 9, 10, 11, 12, 13, 14, or 15 nucleotides from the 5' terminus of PAM.

In some instances, the second nucleic acid molecule, the third nucleic acid molecule, and the fourth nucleic acid molecule are encoded in one or more plasmids. In some instances, the sgRNA encoded by the third nucleic acid molecule comprises a target motif that recognizes a modification at the unnatural nucleotide position within the fourth nucleic acid molecule. In some cases, the modification at the unnatural nucleotide position within the third nucleic acid molecule generates a modified third nucleic acid molecule. In some cases, the modification is a substitution, a deletion, or an insertion. In some cases, the sgRNA encoded by the third nucleic acid molecule further comprises a protospacer adjacent motif (PAM) recognition element. In some cases, the PAM element is adjacent to the 3' terminus of the target motif. In some cases, the combination of Cas9 polypeptide or variants thereof and sgRNA modulates replication of the modified fourth nucleic acid molecule. In some cases, the combination of Cas9 polypeptide or variants thereof, sgRNA and the modified nucleoside triphosphate transporter modulates replication of the modified fourth nucleic acid molecule.

In some cases, the engineered cell further comprises an additional nucleic acid molecule that encodes an additional single guide RNA (sgRNA) comprising a crRNA-tracrRNA scaffold.

In some instances, the combination of Cas9 polypeptide or variants thereof, sgRNA and the modified nucleoside triphosphate transporter decreases the replication rate of the modified fourth nucleic acid molecule by about 80%, 85%, 95%, 99%, or higher. In some instances, the production of the fourth nucleic acid molecule in the engineered cell increases by about 50%, 60%, 70%, 80%, 90%, 95%, 96%, 97%, 98%, 99%, or higher.

In some embodiments, the modified nucleoside triphosphate transporter is expressed in a modified host strain (e.g., the engineered cell), optimized for the expression and activity of the modified nucleoside triphosphate transporter and/or general uptake of nucleoside triphosphates, natural or non-natural. For example, the expression of outer membrane porins, including, but not limited to, OmpA, OmpF, OmpC, may be modified, or the modified nucleoside triphosphate transporter may be expressed in the host cell (e.g., the engineered cell) that also expresses a heterologous outer membrane porin. Alternatively, the host cell (e.g., the engineered cell) may be permeabilized (chemically or by genetic means) to improve the uptake of nucleoside triphosphates. In some embodiments, the host cell (e.g., the engineered cell) may contain deletions of non-essential, endogenously secreted proteins to improve the capacity of the host secretion machinery for expression of the modified nucleoside triphosphate transporter.

In some embodiments, the modified nucleoside triphosphate transporter decreases doubling time of the host cell (e.g., the engineered cell).

In some cases, the modified nucleoside triphosphate transporter enables unnatural base pair retention of about 50%, 60%, 70%, 80%, 90%, 95%, 99%, or more.

Plasmids Encoding a Modified Nucleoside Triphosphate Transporter

In some embodiments, also described herein is an isolated and purified plasmid comprising a nucleic acid molecule encoding a modified nucleoside triphosphate transporter from *Phaeodactylum tricornutum* (PtNTT2); and a promoter region selected from a pSC plasmid or lacZYA locus.

In some instances, the modified nucleoside triphosphate transporter is a codon optimized nucleoside triphosphate transporter from *Phaeodactylum tricornutum.*

In some instances, the modified nucleoside triphosphate transporter comprises a deletion. In some cases, the deletion is a terminal deletion or an internal deletion. In some cases, the deletion is a N-terminal truncation, a C-terminal truncation, or a truncation of both termini.

In some embodiments, the modified nucleoside triphosphate transporter comprises a deletion of about 5, 10, 15, 20, 22, 25, 30, 40, 44, 50, 60, 66, 70, or more amino acid residues. In some instances, the deletion is a N-terminal deletion. In some cases, the modified nucleoside triphosphate transporter comprises a deletion of about 5, 10, 15, 20, 22, 25, 30, 40, 44, 50, 60, 66, 70, or more amino acid residues at the N-terminus. In some cases, the modified nucleoside triphosphate transporter comprises a deletion of about 66 amino acid residues at the N-terminus.

In some instances, the isolated and modified nucleoside triphosphate transporter comprises at least 80%, 85%, 90%, 95%, 96%, 97%, 98%, or 99% sequence identity sequence identity to SEQ ID NOs: 4, 6, or 8. In some cases, the isolated and modified nucleoside triphosphate transporter comprises at least 80%, 85%, 90%, 95%, 96%, 97%, 98%, or 99% sequence identity sequence identity to SEQ ID NO: 4. In some cases, the isolated and modified nucleoside triphosphate transporter comprises 100% sequence identity to SEQ ID NO: 4. In some cases, the isolated and modified nucleoside triphosphate transporter comprises at least 80%, 85%, 90%, 95%, 96%, 97%, 98%, or 99% sequence identity to SEQ ID NO: 6. In some cases, the isolated and modified nucleoside triphosphate transporter comprises 100% sequence identity to SEQ ID NO: 6. In some cases, the isolated and modified nucleoside triphosphate transporter comprises at least 80%, 85%, 90%, 95%, 96%, 97%, 98%, or 99% sequence identity to SEQ ID NO: 8. In some cases, the isolated and modified nucleoside triphosphate transporter comprises 100% sequence identity to SEQ ID NO: 8.

In some embodiments, the modified nucleoside triphosphate transporter is under the control of a promoter. Exemplary promoters, include, but are not limited to, $P_{bla}$, $P_{lac}$, $P_{lacUV5}$, $P_{H207}$, $P_{\lambda}$, $P_{tac}$, or $P_{N25}$. In some instances, the promoter replaces the lac operon. In some cases, the modified nucleoside triphosphate transporter is under the control of a promoter selected from $P_{bla}$, $P_{lac}$, $P_{lacUV5}$, $P_{H207}$, $P_{\lambda}$, $P_{tac}$, or $P_{N25}$. In some cases, the modified nucleoside triphosphate transporter is under the control of promoter $P_{lacUV5}$.

In some instances, the modified nucleoside triphosphate transporter is encoded within a pSC plasmid.

In some embodiments, also disclosed herein is an in vivo method of increasing the production of a nucleic acid molecule containing an unnatural nucleotide comprising incubating a cell with an isolated and purified plasmid described supra.

Nucleic Acid Molecules

In some embodiments, a nucleic acid (e.g., also referred to herein as nucleic acid molecule of interest) is from any source or composition, such as DNA, cDNA, gDNA (genomic DNA), RNA, siRNA (short inhibitory RNA), RNAi, tRNA, mRNA or rRNA (ribosomal RNA), for example, and is in any form (e.g., linear, circular, supercoiled, single-stranded, double-stranded, and the like). In some embodiments, nucleic acids comprise nucleotides, nucleosides, or polynucleotides. In some cases, nucleic acids comprise natural and unnatural nucleic acids. In some cases, a nucleic acid also comprises unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phagemid, autonomously replicating sequence (ARS), centromere, artificial chromosome, yeast artificial chromosome (e.g., YAC) or other nucleic acid able to replicate or be replicated in a host cell. In some cases, an unnatural nucleic acid is a nucleic acid analogue. In additional cases, an unnatural nucleic acid is from an extracellular source. In other cases, an unnatural nucleic acid is available to the intracellular space of an organism provided herein, e.g., a genetically modified organism.

Unnatural Nucleic Acids

A nucleotide analog, or unnatural nucleotide, comprises a nucleotide which contains some type of modification to either the base, sugar, or phosphate moieties. In some embodiments, a modification comprises a chemical modification. In some cases, modifications occur at the 3'OH or 5'OH group, at the backbone, at the sugar component, or at the nucleotide base. Modifications, in some instances, optionally include non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect, a modified backbone comprises a backbone other than a phosphodiester backbone. In one aspect, a modified sugar comprises a sugar other than deoxyribose (in modified DNA) or other than ribose (modified RNA). In one aspect, a modified base comprises a base other than adenine, guanine, cytosine or thymine (in modified DNA) or a base other than adenine, guanine, cytosine or uracil (in modified RNA).

In some embodiments, the nucleic acid comprises at least one modified base. In some instances, the nucleic acid comprises 2, 3, 4, 5, 6, 7, 8, 9, 10, 15, 20, or more modified bases. In some cases, modifications to the base moiety include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes, but is not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CI¼) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyl adenine, 2-F-adenine, 2-aminoadenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, $N_4$-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acid in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, 2-amino-4-oxopyrrolo[2.3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, a modified base of a unnatural nucleic acid is depicted below, wherein the wavy line identifies a point of attachment to the (deoxy)ribose or ribose.

-continued

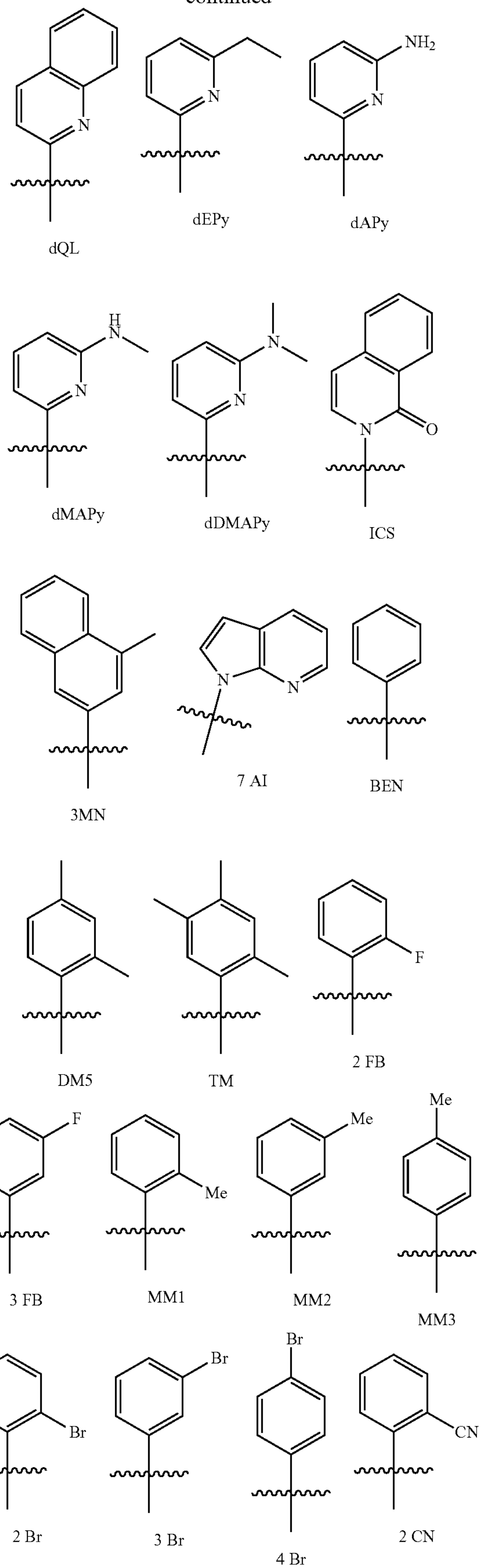

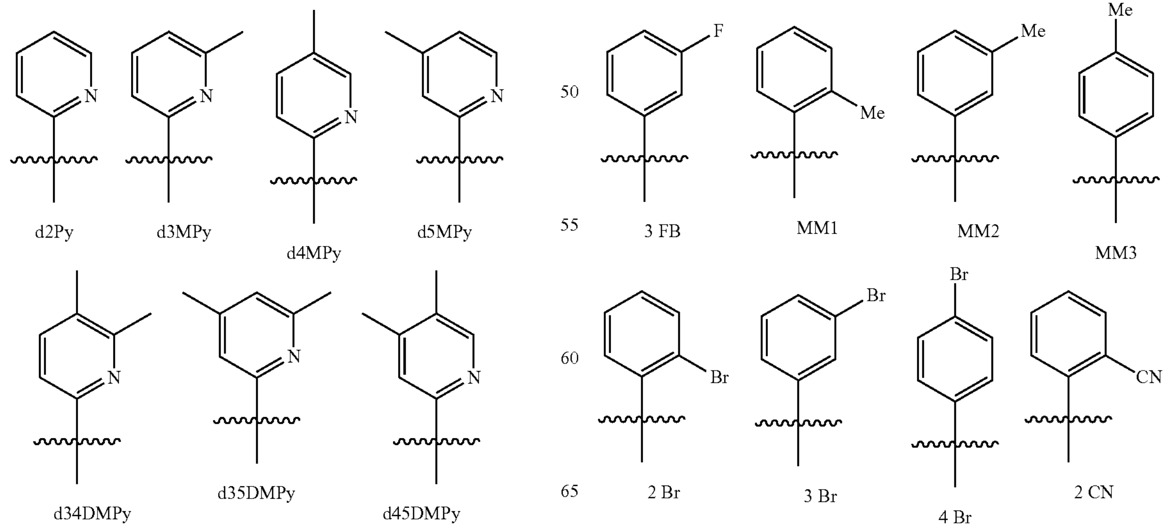

-continued
-continued
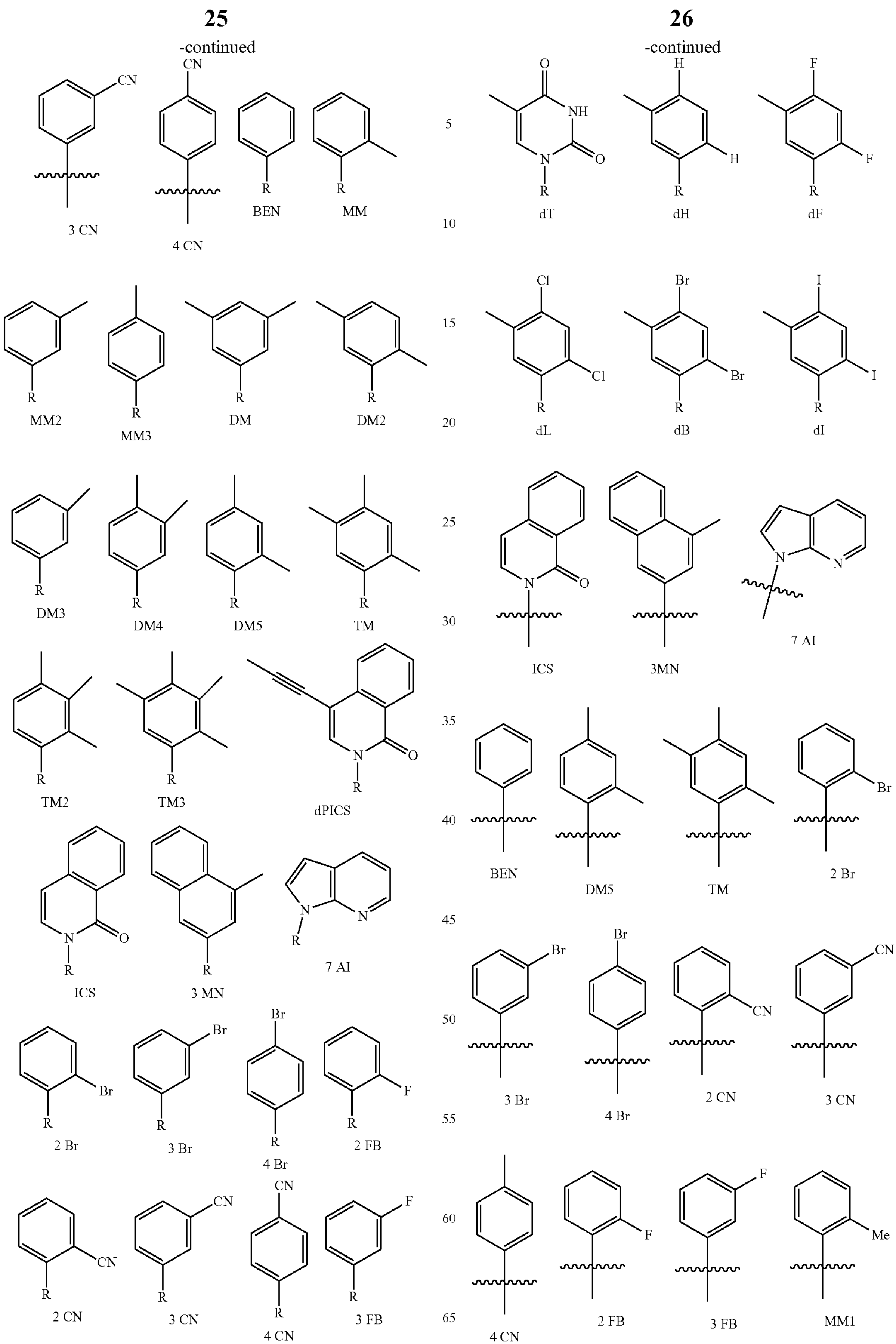
3 CN, 4 CN, BEN, MM, dT, dH, dF, MM2, MM3, DM, DM2, dL, dB, dI, DM3, DM4, DM5, TM, ICS, 3MN, 7 AI, TM2, TM3, dPICS, BEN, DM5, TM, 2 Br, ICS, 3 MN, 7 AI, 3 Br, 4 Br, 2 CN, 3 CN, 2 Br, 3 Br, 4 Br, 2 FB, 4 CN, 2 FB, 3 FB, MM1, 2 CN, 3 CN, 4 CN, 3 FB -continued
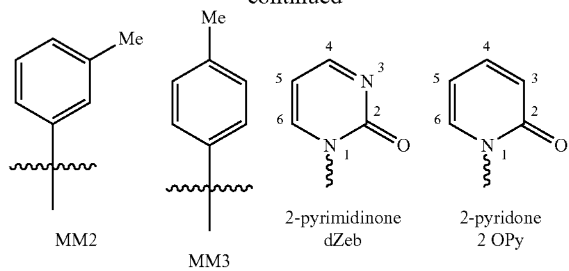
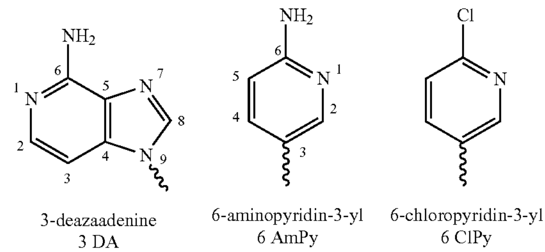
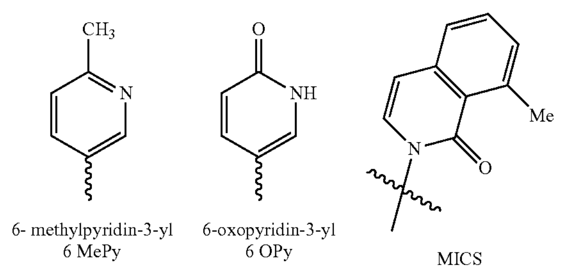
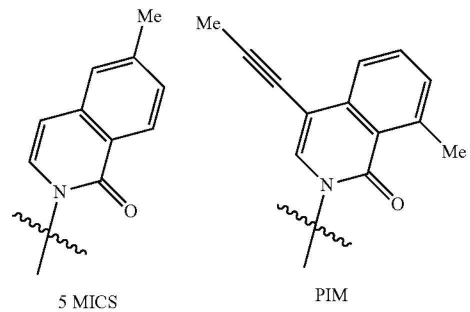
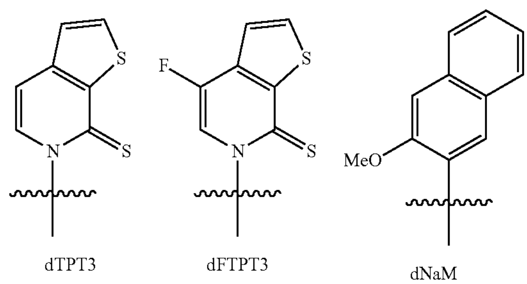
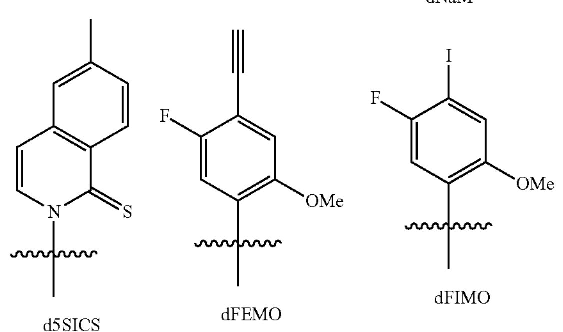
-continued
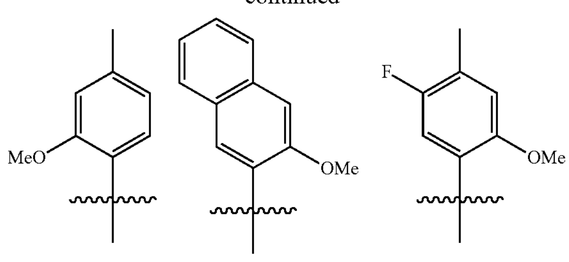
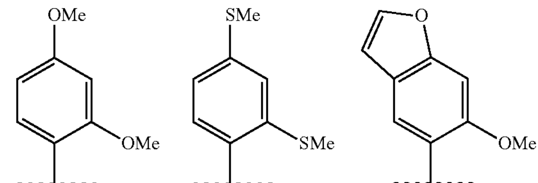
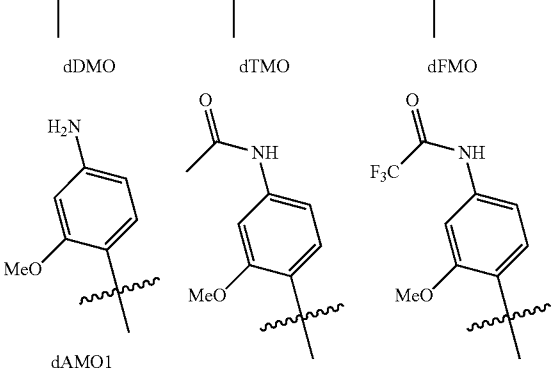
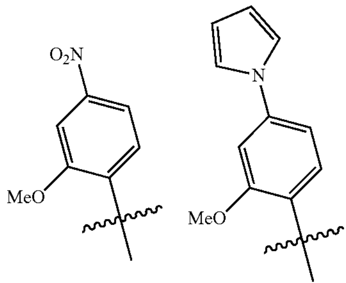
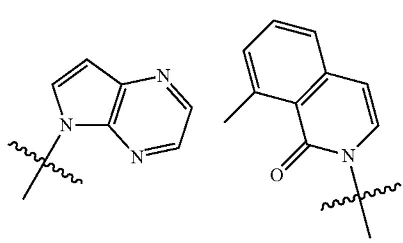
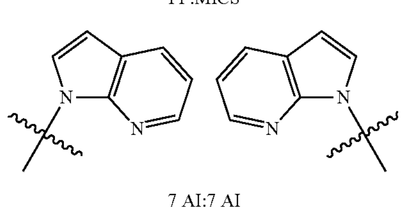

-continued

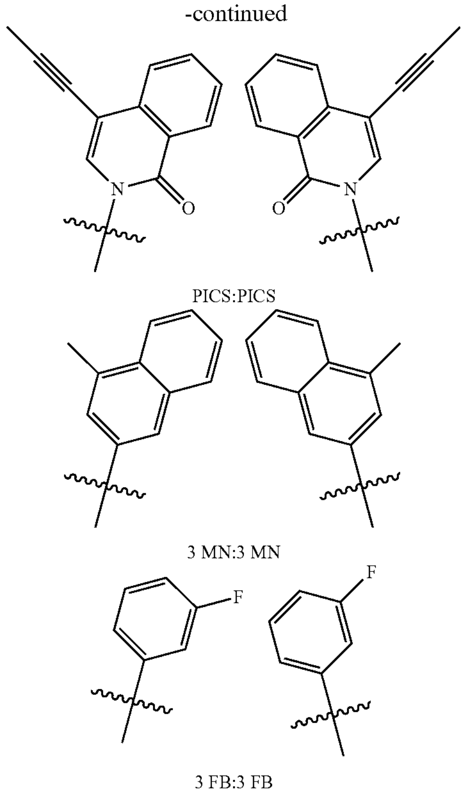

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or C(Ri)($R_2$) (R=H, $C_1$-$C_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxy-pentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta]anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —$O[(CH_2)_nO]_mCH_3$, —$O(CH_2)_nOCH_3$, —$O(CH_2)_nNH_2$, —$O(CH_2)_nCH_3$, —$O(CH_{2-})_nONH_2$, and —$O(CH_2)_nON[(CH_2)_n CH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-$O(CH_2)_2$ $OCH_3$ substituent groups. The substituent at the 2' position can also be selected from allyl, amino, azido, thio, O-allyl, O—($C_1$-$C_{10}$alkyl), $OCF_3$, $O(CH_2)_2SCH_3$, $O(CH_2)_2$—O—N$(R_m)(R_n)$, and O—$CH_2$—C(═O)—N$(R_m)(R_n)$, where each $R_m$ and $R^n$ is, independently, H or substituted or unsubstituted $C_1$-$C_{10}$alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-CH$(CH_2OCH_3)$—O-2', and analogs thereof (see, U.S. Pat. No. 7,399,845); 4'-$C(CH_3)(CH_3)$—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P═S). Representative non-phosphorus containing inter nucleic acid linking groups include, but are not limited to, methylenemethylimino (—$CH_2$—N$(CH_3)$—O—$CH_2$—), thiodiester (—O—C(O)—S—), thionocarbamate (—O—C(O)(NH)—S—); siloxane (—O—$Si(H)_2$—O—); and N,N*-dimethylhydrazine (—$CH_2$—N$(CH_3)$—N$(CH_3)$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Nucleic Acid Base Pairing Properties

In some embodiments, an unnatural nucleic acid forms a base pair with another nucleic acid. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleotide triphosphates that can base pair when incorporated into nucleic acids include a triphosphate of d5SICS (d5SICSTP) and a triphosphate of dNaM (dNaMTP). Such unnatural nucleotides can have a ribose or deoxyribose sugar moiety. In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural nucleic acid is an unnatural nucleic acid that can form a UBP, but does not substantially form a base pair with each of the four natural nucleic acids. In some embodiments, a stably integrated unnatural nucleic acid is an unnatural nucleic acid that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo includes, but is not limited to, 5SICS, d5SICS, NAM, dNaM, and combinations thereof. In some embodiments, unnatural nucleotides include:

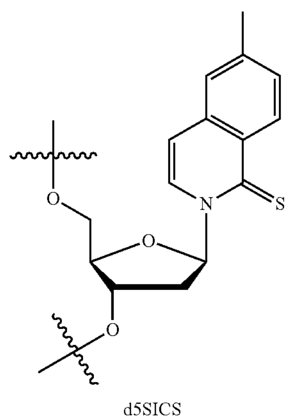

d5SICS

-continued

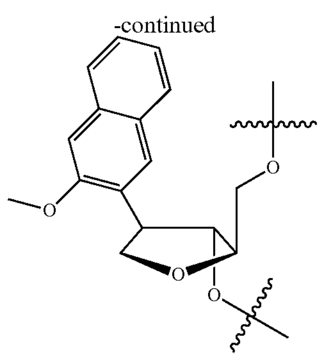

dNAM

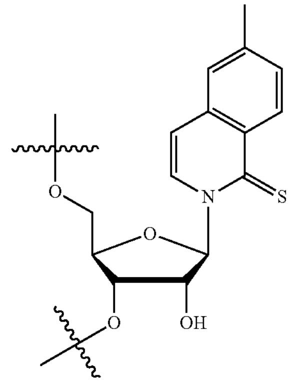

5SICS

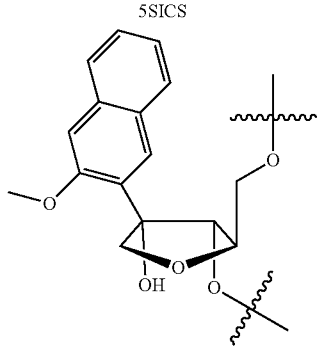

NAM

Polymerase

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

In some instances, disclosed herein includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3 to 5' exonuclease proofreading activity or where a 3 to 5' exonuclease proofreading activity has been disabled, e.g. through mutation. Examples of DNA polymerases include polA, polB (see e.g. Parrel & Loeb, Nature Struc Biol 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In some embodiments, polymerases are characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

In some embodiments, polymerases are characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of ($k_{cat}/K_m$) for the natural and unnatural nucleic acid and ($kc_{at}/K_m$) for the incorrect natural and unnatural nucleic acid; where $k_{cat}$ and $K_m$ are Michaelis-Menten parameters in steady state enzyme kinetics (Fersht, A. R. (1985) Enzyme Structure and Mechanism, 2nd ed., p 350, W. H. Freeman & Co., New York, incorporated herein by reference). In some embodiments, a polymerase has a fidelity value of at least about 100, 1000, 10,000, 100,000, or $1\times10^6$, with or without a proofreading activity.

In some embodiments, polymerases from native sources or variants thereof are screened using an assay that detects incorporation of an unnatural nucleic acid having a particular structure. In one example, polymerases can be screened for the ability to incorporate an unnatural nucleic acid or UBP; e.g., d5SICSTP, dNaMTP, or d5SICSTP-dNaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., d5SICSTP, dNaMTP, or d5SICSTP-dNaMTP UBP into nucleic acids. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, G1, Cp-1, PRD1, PZE, SFS, Cp-5, Cp-7, PR4, PR5, PR722, or L17 polymerase.

Nucleic acid polymerases generally useful in the invention include DNA polymerases, RNA polymerases, reverse transcriptases, and mutant or altered forms thereof. DNA polymerases and their properties are described in detail in, among other places, DNA Replication 2nd edition, Kornberg and Baker, W. H. Freeman, New York, N. Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al, 1991, Polynucleotides Res, 19: 4193, New England Biolabs), 9° Nm™ DNA polymerase (New England Biolabs), Stoffel fragment, Thermo Sequenase® (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al, 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al, 1981, J Biol. Chem. 256:3112), and archaeal DP1I/DP2 DNA polymerase II (Cann et al, 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3 exonuclease-deficient mutant is also contemplated.

Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al, CRC Crit Rev Biochem. 3:289-347(1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase Gardner et al. (2004) "Comparative Kinetics of Nucleotide Analog Incorporation by Vent DNA Polymerase (J. Biol. Chem., 279(12), 11834-11842; Gardner and Jack "Determinants of nucleotide sugar recognition in an archaeon DNA polymerase" Nucleic Acids Research, 27(12) 2545-2553.) Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

In some embodiments, the polymerase comprises Φ29, B103, GA-1, PZA, Φ15, BS32, M2Y, Nf, G1, Cp-1, PRD1, PZE, SFS, Cp-5, Cp-7, PR4, PR5, PR722, L17, ThermoSequenase®, 9° Nm™, Therminator™ DNA polymerase, Tne, Tma, TfI, Tth, TIi, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some embodiments, the polymerase is DNA polymerase 1-Klenow fragment, Vent polymerase, Phusion® DNA polymerase, KOD DNA polymerase, Taq polymerase, T7 DNA polymerase, T7 RNA polymerase, Therminator™ DNA polymerase, POLB polymerase, SP6 RNA polymerase, *E. coli* DNA polymerase I, *E. coli* DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Nucleic Acid Reagents & Tools

A nucleic acid reagent for use with a method, cell, or engineered microorganism described herein comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleic acid reagent or other reagent described herein is isolated or purified.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A nucleic acid or nucleic acid reagent can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

As noted above, nucleic acid reagents may also comprise one or more 5' UTR's, and one or more 3'UTR's. For example, expression vectors used in prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR is used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

Cloning

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, BsaI, Bsm I, BsmBI, BssH II, BstE II, Cfo I, CIa I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein λ, Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993)).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another function efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern et al., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985)).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, a kit includes a suitable packaging material to house the contents of the kit. In some cases, the packaging material is constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

In some embodiments, a kit is provided that is useful for stably incorporating an unnatural nucleic acid into a cellular nucleic acid, e.g., using the methods provided by the present invention for preparing genetically engineered cells. In one embodiment, a kit described herein includes a genetically engineered cell and one or more unnatural nucleic acids. In another embodiment, a kit described herein includes an isolated and purified plasmid comprising a sequence selected from SEQ ID NOs: 1-9. In a further embodiment, a kit described herein includes an isolated and purified plasmid comprises a sequence of SEQ ID NOs: 2, 3, 5, or 7.

In additional embodiments, the kit described herein provides a cell and a nucleic acid molecule containing a heterologous gene for introduction into the cell to thereby provide a genetically engineered cell, such as expression vectors comprising the nucleic acid of any of the embodiments hereinabove described in this paragraph.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

EXAMPLES

These examples are provided for illustrative purposes only and not to limit the scope of the claims provided herein.

Example 1

All natural organisms store genetic information in a four letter, and two base pair genetic alphabet. In some instances, a mutant form of *Escherichia coli* was generated, grown in the presence of the unnatural nucleoside triphosphates dNaMTP and d5SICSTP, and provided with the means to import them via expression of a plasmid-borne nucleoside triphosphate transporter, replicates DNA containing a single dNaM-d5SICS UBP. In some cases, the organism grew poorly, and was unable to indefinitely store the unnatural information, which is a prerequisite for true semi-synthetic life. Described below comprise an engineered transporter, coupled with a chemically optimized UBP, to generate a semi-synthetic organism (SSO).

Methods

Unless otherwise stated, liquid bacterial cultures were grown in 2×YT (casein peptone 16 g/L, yeast extract 10 g/L, NaCl 5 g/L) supplemented with potassium phosphate (50 mM, pH 7), referred to hereafter as "media", and incubated at 37° C. in a 48-well flat bottomed plate (CELLSTAR, Greiner Bio-One) with shaking at 200 rpm. Solid growth media was prepared with 2% agar. Antibiotics were used, as appropriate, at the following concentrations: carbenicillin, 100 μg/mL; streptomycin, 50 μg/mL; kanamycin, 50 μg/mL; zeocin, 50 μg/mL; chloramphenicol, 33 μg/mL for plasmids, 5 μg/mL for chromosomal integrants. All selective agents were purchased commercially. Cell growth, indicated as $OD_{600}$, was measured using a Perkin Elmer Envision 2103 Multilabel Reader with a 590/20 nm filter.

Unless otherwise stated, all molecular biology reagents were obtained from New England Biolabs (NEB) and were used according to the manufacturer's protocols. PCRs for cloning and strain construction were performed with Q5 DNA polymerase. Thermocycling was performed using a PTC-200 thermocycler (MJ Research), except for the PCRs used to generate UBP-containing Golden Gate inserts and the PCRs used in the biotin shift assay, which were performed with a CFX-Connect Real-Time Thermal Cycler (Bio-Rad) to monitor product amplification with SYBR Green (Thermo Fisher). Where necessary, primers were phosphorylated using T4 polynucleotide kinase. Plasmids linearized by PCR were treated with Dpnl to remove the plasmid template, and ligations were performed with T4 DNA ligase. PCRs and Golden Gate assembled plasmids were purified by spin column (DNA Clean and Concentrator-5, Zymo Research). DNA fragments isolated by agarose gel electrophoresis were purified using the Zymoclean Gel DNA recovery kit (Zymo Research). Colony PCRs were performed with Taq DNA polymerase. Natural DNA fragments and plasmids were quantified by A260/280 using a NanoDrop 2000 (Thermo Fisher) or an Infinite M200 Pro (Tecan). DNA fragments and plasmids that contain UBP(s), which were typically <20 ng/μL, were quantified using the Qubit dsDNA HS Assay Kit (Thermo Fisher).

The sequences of all DNA oligonucleotides used in this study are provided in Table 2. Natural oligonucleotides were purchased from IDT (San Diego, California, USA) with standard purification and desalting. Gene synthesis of the codon optimized PtNTT2 and GFP gene sequences was performed by GeneArt Gene Synthesis (Thermo Fisher) and GenScript, respectively, and kindly provided by Synthorx. Sequencing was performed by Eton Biosciences (San Diego, California, USA) or Genewiz (San Diego, California, USA). Plasmids were isolated using commercial miniprep kits (QIAprep, Qiagen or ZR Plasmid Miniprep Classic, Zymo Research).

[$\alpha$-$^{32}$P]-dATP (3000 Ci/mmol, 10 mCi/mL) was purchased from PerkinElmer (Shelton, Connecticut, USA). Triphosphates of dNaM, d5SICS, dTPT3, and dMMO2$^{bio}$ were synthesized as described in Li et al, "Natural-like replication of an unnatural base pair for the expansion of the genetic alphabet and biotechnology applications," *J. Am. Chem. Soc.* 136, 825-829 (2014); or kindly provided by Synthorx (San Diego, California, USA). The dNaM-containing TK1 oligonucleotide was described in Malyshev, et al., "A semi-synthetic organism with an expanded genetic alphabet," *Nature,* 509, 385-388 (2014). All other unnatural oligonucleotides containing dNaM were synthesized by Biosearch Technologies (Petaluma, California, USA) with purification by reverse phase cartridge.

The C41(DE3) *E. coli* strain was kindly provided by J. P. Audia (University of South Alabama, USA). pKIKOarsBKm was a gift from Lars Nielsen & Claudia Vickers (Addgene plasmid #46766). pRS426 was kindly provided by Richard Kolodner (University of California San Diego, USA).

Construction of PtNTT2 Plasmids

Construction of pCDF-1b-PtNTT2 was described Malyshev, et al., "A semi-synthetic organism with an expanded genetic alphabet," *Nature,* 509, 385-388 (2014). To create pCDF-1b-PtNTT2(66-575), phosphorylated primers YZ552 and pCDF-1b-fwd were used to linearize pCDF-1b-PtNTT2 by PCR and the resulting product was intramolecularly ligated. Plasmids from single clones were isolated and confirmed by sequencing the PtNTT2 gene using primers T7 seq and T7 term seq.

To create plasmids pSC-$P_{(lacI,\ bla,\ lac,\ lacuv5)}$PtNTT2(66-575)-$T_0$, phosphorylated primers YZ581 and YZ576 were used to amplify the PtNTT2(66-575) gene, and its corresponding ribosomal binding sequence and terminator, from a version of pCDF-1b-PtNTT2(66-575) that replaces the T7 terminator with a $\lambda$ $T_0$ terminator. This insert was ligated into plasmid pHSG576 linearized with primers DM002 and YZ580. A single clone of the resulting plasmid pSC-PtNTT2 (66-575)-$T_0$ was verified by sequencing the PtNTT2 gene using primers DM052 and YZ50. pSC-PtNTT2(66-575)-$T_0$ was then linearized with primers YZ580 and YZ581, and ligated to a phosphorylated primer duplex corresponding to the $P_{lacI}$, $P_{bla}$, $P_{lac}$ or $P_{lacUV5}$ promoter (YZ584/YZ585, YZ582/YZ583, YZ599/YZ600, and YZ595/YZ596, respectively) to yield plasmids pSC-$P_{(lacI,\ bla,\ lac,\ lacUV5)}$/PtNTT2 (66-575)-$T_0$. Correct promoter orientation and promoter-gene sequences were again confirmed by sequencing using primers DM052 and YZ50. pSC-$P_{bla}$PtNTT2(66-575 co)-$T_0$ was generated analogously to pSC-$P_{bla}$PtNTT2(66-575)-$T_0$ by using a $\lambda$ $T_0$ terminator version of pCDF-1b-PtNTT2(66-575) containing a codon optimized PtNTT2 sequence (see Table 2).

Construction of PtNTT2 and Cas9 Strains

The PtNTT2(66-575) expression cassette and its chloramphenicol resistance marker $Cm^R$ in the pSC plasmids is ~2.8 kb, a size that is prohibitive for chromosomal integration with the small (~50 bp) stretches of homology that can be introduced via primers during PCR, as is traditionally done in recombineering. Homologous recombination in *S. cerevisiae* was used to construct a series of integration template plasmids with the PtNTT2(66-575) expression cassette and $Cm^R$ flanked by ~1 kb of sequence 5' to lacZ and ~1 kb of sequence 3' to 246 bp downstream of the lacA start codon. The lacZYA locus was chosen so that integration of the transporter would also knockout the lactose permease lacY, thus creating a BL21(DE3) strain that allows for uniform cellular entry of IPTG, and thereby homogenous, finely titratable induction of promoters containing lac operators.

To create the integration template plasmids, pRS426 was digested with PvuI-HF and the resulting 3810-bp plasmid fragment was isolated by agarose gel electrophoresis and purification. This fragment was then gap repaired in the *S. cerevisiae* strain BY4741 via lithium acetate mediated chemical transformation of the plasmid fragment and PCR products of the following primer/primer/template combinations: YZ7/YZ12/pBR322, YZ613/YZ580/*E. coli* genomic DNA, YZ614/615/*E. coli* genomic DNA, and DM052/YZ612/pSC-Piacuv5(66-575)-$T_0$. The resulting plasmid, 426.lacZYA:$P_{lacUV5}$PtNTT2(66-575)-$T_0$ $Cm^R$, was isolated (Zymoprep Yeast Plasmid Miniprep, Zymo Research), digested with PvuI-HF and XbaI (to reduce background during integration, since the pRS426 shuttle plasmid also contains an *E. coli* pMB1 origin), and used as the template to generate a linear integration fragment via PCR with primers YZ616 and YZ617. Integration of this fragment into BL21(DE3) to generate strain YZ2 was performed using pKD46 as described in Datsenko, et al., "One-step inactivation of chromosomal genes in *Escherichia coli* K-12 using PCR products," PNAS 97, 6640-6645 (2000). Integrants were confirmed by colony PCR of the 5' and 3' junctions using primers YZ618 and YZ587 (1601-bp product) and YZ69 and YZ619 (1402-bp product), respectively, detection of lacZ deletion via growth on plates containing X-gal (80 μg/mL) and IPTG (100 μM), and PCR and sequencing of the transporter with primers DM053 and YZ50.

Plasmid 426.lacZYA::$Cm^R$ was generated from the linearization of 426.lacZYA::$P_{lacuv5}$PtNTT2(66-575)-$T_0$ $Cm^R$ using phosphorylated primers YZ580 and pCDF-1b-rev, and subsequent intramolecular ligation. 426.lacZYA::$Cm^R$ was then integrated into BL21(DE3) to create an isogenic, transporter-less control strain for dATP uptake assays.

To create plasmids 426.lacZYA::$P_{(bla,\ lac,\ lacuv5)}$PtNTT2 (66-575 co)-$T_0$ $Cm^R$, plasmid 426.lacZYA::PtNTT2(66-575)-$T_0$ $Cm^R$ (a promoter-less plasmid generated analogously to 426.lacZYA::$P_{lacUV5}$PtNTT2(66-575)-$T_0$ $Cm^R$ using pSC-PtNTT2(66-575)-$T_0$), referred to hereafter as 426.trunc, was digested with PvuI-HF and AvrII, and the resulting 5969-bp plasmid fragment was isolated by agarose gel electrophoresis and purification, and gap repaired using PCR products of the following primer/primer/template combinations: 1, YZ12/YZ580/426.trunc; 2, DM053/YZ610/pSC-$P_{(bla,\ lac,\ lacUV5}$PtNTT2(66-575)-$T_0$; 3, YZ581/YZ50/pSC-PSC-$P_{bla}$PtNTT2(66-575 co)-$T_0$. Plasmids 426.lacZYA::$P_{(tac,\ N25,\ \lambda,\ H207)}$PtNTT2(66-575 co)-$T_0$ $Cm^R$ were generated analogously except fragments 2 were replaced with fragments corresponding to the promoters $P_{tac}$, $P_{N25}$, $P_{\lambda}$, and $P_{H207}$, which were generated by annealing and extension of primer pairs YZ703/YZ704, YZ707/YZ708, YZ709/YZ710, and YZ711/YZ712, respectively, with Klenow fragment. Plasmids 426.1acZYA:$P_{(bla,\ lac,\ lacUV5,\ tac,\ N25,\ H207)}$PtNTT2(66-575 co)-$T_0$ $Cm^R$ were then used to integrate the transporter into BL21(DE3) using primers YZ616 and YZ617, and recombineering, as described above. Strain YZ3 denotes BL21(DE3) integrated with lacZYA::$P_{lacUV5}$PtNTT2(66-575 co)-$T_0$ $Cm^R$.

To create strain YZ4, the 4362-bp fragment of SpeI and AvrII digested pCas9-Multi was ligated into SpeI digested pKIKOarsBKm and the resulting plasmid, pKIKOarsB:$P_{lacO}$-Cas9-$T_{rrnB}$ $Km^R$, was used as the template to generate a linear integration fragment via PCR with primers YZ720 and YZ721. The fragment was then integrated into BL21 (DE3) as described above, and confirmed by colony PCR with primers YZ720 and YZ721 and sequencing of the product with primers TG1-TG6. $P_{lacUV5}$PtNTT2(66-575 co)-$T_0$ $Cm^R$ was subsequently integrated into this strain, as described above, to generate strain YZ4.

dATP Uptake Assay

Radioactive uptake assays were conducted as described in Haferkamp, et al., "Tapping the nucleotide pool of the host: novel nucleotide carrier proteins of *Protochlamydia amoebophila,*" *Mol. Microbial.* 60, 1534-1545 (2006) with the following modifications: C41(DE3) and BL21(DE3) strains carrying plasmid-based transporters and their appropriate empty plasmid controls, as well as BL21(DE3) chromosomal transporter integrants and their appropriate isogenic transporter-less control, were grown overnight with appropriate antibiotics (streptomycin for pCDF plasmids and chloramphenicol for pSC plasmids and integrants) in 500 μL of media. Cultures were diluted to an $OD_{600}$ of 0.02 in 500 μL of fresh media, grown for 2.5 h, induced with IPTG (0-1 mM, pCDF strains only) or grown (all other strains) for 1 h, and incubated with dATP spiked with [$\alpha$-$^{32}$P]-dATP (final concentration=250 μM (0.5 μCi/mL)) for ~1 h. This experimental scheme is analogous to the protocol used to prepare cells for transformation with UBP-containing plasmids, with the 1 h of dATP incubation simulating the 1 h of recovery in the presence of unnatural triphosphates following electroporation. A duplicate 48-well plate without [$\alpha$-$^{32}$P]-dATP was grown in parallel to monitor growth.

Following incubation with dATP, 200 μL of each culture was collected through a 96-well 0.65 μm glass fiber filter plate (Multi Screen, EMD Millipore) under vacuum and washed with cold potassium phosphate (3×200 μL, 50 mM, pH 7) and cold dd$H_2O$ (1×200 μL). Filters were removed from the plate and exposed overnight to a storage phosphor screen (BAS-IP MS, GE Healthcare Life Sciences), which was subsequently imaged using a flatbed laser scanner (Typhoon 9410, GE Healthcare Life Sciences). The resulting image was quantified by densitometric analysis using Image Studio Lite (LI-COR). Raw image intensities of each sample were normalized to the length of time and average $OD_{600}$ during dATP incubation (i.e. normalized to an estimate of the area under the growth curve corresponding to the window of uptake), followed by subtracting the normalized signals of the appropriate negative, no transporter controls.

Doubling times for strains grown in the dATP uptake assay were calculated by doubling time as $(t_2-t_1)/\log_2(OD_{600,2}/OD_{600,1})$, averaging across three, ~30 min time intervals roughly corresponding to 30 min prior to dATP uptake and 60 min during dATP uptake.

Construction of Golden Gate Destination Plasmids for pUCX1, pUCX2, and pBRX2

Although the UBP was cloned into plasmids via circular polymerase extension cloning (CPEC)[4,27], the method results in a doubly-nicked plasmid that cannot be treated with T5 exonuclease to degrade unincorporated linear plasmid and inserts, and thus makes it difficult to accurately quantify the yield of the cloning reaction and control the amount of input plasmid used to transform cells during an in vivo replication experiment. Furthermore, the unincorporated linear plasmid and inserts of a CPEC reaction can also template PCR reactions with the primers used in the biotin shift assay, and thus biotin shift assays on CPEC products do not truly reflect the UBP content of the plasmids that are actually transformed into cells. To circumvent these complications, the UBP was incorporated into plasmids using Golden Gate Assembly.

To create pUCX1 GG and pUCX2 GG, the Golden Gate destination plasmids for pUCX1 and pUCX2, respectively, pUC19 was linearized with phosphorylated primers pUC19-lin-fwd and pUC19-lin-rev, and the resulting product was intramolecularly ligated to delete the natural 75-nt TK1 sequence. The resulting plasmid was then linearized with phosphorylated primers YZ51 and YZ52, and the resulting product was intramolecularly ligated to mutate the BsaI recognition site within the ampicillin resistance marker $Amp^R$. This plasmid was then linearized with primers pUC19-lin-fwd and pUC19-lin-rev (for pUCX1), or primers YZ95 and YZ96 (for pUCX2), and ligated to an insert generated from PCR with phosphorylated primers YZ93 and YZ94 and template pCas9-Multi, to introduce two BsaI recognition sites (for cloning by Golden Gate Assembly) and a zeocin resistance marker (a stuffer cassette used to differentiate between plasmids with or without an insert) into pUC19.

To create pBRX2 GG, the Golden Gate destination plasmid for pBRX2, the 2934-bp fragment of AvaI and EcoRI-HF digested pBR322 was end-filled with Klenow fragment and intramolecularly ligated to delete the tetracycline resistance cassette. The BsaI recognition site within $Amp^R$ was mutated as described above. The plasmid was then linearized with primers YZ95 and YZ96, and ligated to the BsaI-$zeo^R$-BsaI cassette as described above. Thus, pBRX2 is a lower copy analog of pUCX2.

Golden Gate Assembly of UBP-Containing Plasmids

Plasmids containing UBP(s) were generated by Golden Gate Assembly. Inserts containing the UBP were generated by PCR of chemically synthesized oligonucleotides containing dNaM, using dTPT3TP and dNaMTP, and primers that introduce terminal BsaI recognition sites that, when digested, produce overhangs compatible with an appropriate destination plasmid; see Table 2 for a full list of primers, templates and their corresponding Golden Gate destination plasmids. Template oligonucleotides (0.025 ng per 50 μL reaction) were PCR amplified using reagent concentrations and equipment under the following thermocycling conditions (times denoted as mm:ss): [96° C. 1:00|20×[96° C. 0:15|60° C. 0:15| 68° C. 4:00]].

To assemble the UBP-containing plasmids, destination plasmid (200-400 ng), PCR insert(s) (3:1 insert:plasmid molar ratio), T4 DNA ligase (200 U), BsaI-HF (20 U), and ATP (1 mM) were combined in 1×NEB CutSmart buffer (final volume 30 μL) and thermocycled under the following conditions: [37° C. 20:00|40× [37° C. 5:00||6° C. 5:00|22° C. 2:30]37° C. 20:00|55° C. 15:00|80° C. 30:00]. Following the Golden Gate reaction, T5 exonuclease (10 U) and additional BsaI-HF (20 U) were added, and the reaction was incubated (37° C., 1 h) to digest unincorporated plasmid and insert fragments. Assembled plasmids were quantified by Qubit.

Construction of Golden Gate Destination Plasmids for pCas9 and pAIO

To create pCas9-Multi, the Golden Gate destination plasmid for cloning sgRNA cassettes alongside Cas9, pPDAZ[29] and a PCR amplified Cas9 gene (Primers JL126 and JL128, template Addgene plasmid #41815) were digested with KpnI and XbaI, and ligated to create pCas9(-). This plasmid and a PCR amplified GFPT2-sgRNA cassette (template Addgene plasmid #41820, which contains the sgRNA sequence; the ProK promoter and terminator were introduced by PCR) were digested with SalI and ligated to created pCas9-GFPT2. This plasmid was then linearized with primers BL557 and BL558 (to remove the BsmBI recognition sites within Cas9) and circularized via Gibson Assembly. The resulting plasmid was then linearized with primers BL559 and BL560 (to reintroduce two BsmBI sites in the plasmid backbone), and circularized via Gibson Assembly to yield pCas9-Multi, which was confirmed by sequencing with primers TG1-TG6. Digestion of pCas9-Multi with BsmBI results in a linearized plasmid with overhangs that allow for the simultaneous cloning of one or more sgRNAs by Golden Gate Assembly (see section below).

To create pAIO-Multi, pCas9-Multi was linearized with primers BL731 and BL732 (to remove Cas9 and introduce BsaI recognition sites for UBP cloning), phosphorylated, and intramolecularly ligated, and confirmed by sequencing with primer BL450. Digestion of pAIO-Multi with BsaI results in a linearized plasmid with overhangs identical to the ones produced by BsaI digestion of the pUCX2 destination plasmid, and thus PCR-generated inserts for cloning the UBP into pUCX2 can also be used to clone the UBP into pAIO-Multi and its derivatives. After the sgRNA cassettes were cloned into pAIO-Multi (see next section below), the Golden Gate Assembly protocol for cloning in a UBP was identical to the one described above for pUCX2, except the product of pAIO-Multi (with sgRNAs) amplified with BL731 and BL732 was used in place of the plasmid itself.

sgRNA Cloning into pCas9 and pAIO

Dual sgRNA cassettes were cloned into pCas9-Multi or pAIO-Multi via Golden Gate Assembly. To generate the first sgRNA cassette of each pair, pCas9-GFPT2 (1 ng) was PCR amplified with primers 1$^{st}$ sgRNA GG (200 nM) and BL562 (200 nM), and OneTaq DNA polymerase, under the following thermocycling conditions: [30× [94° C. 0:30|52° C. 0:15|68° C. 0:30]]. PCR products were purified by agarose gel electrophoresis and purification. The 1$^{st}$ sgRNA GG primer is a 70-nt primer that possesses (from 5' to 3') a BsmBI restriction site, 10-nt of homology with the ProK promoter, an 18-nt variable guide (spacer) complementary to a UBP-mutation, and 25-nt of homology to the non-variable sgRNA scaffold. To generate the second sgRNA cassette, pCas9-GFPT2 was PCR amplified with primers BL563 and 2$^{nd}$ sgRNA Rev, and primers BL566 and 2$^{nd}$ sgRNA Fwd, and the resulting two products were combined and amplified by overlap extension PCR using primers BL563 and BL566, followed by agarose gel electrophoresis and purification.

To assemble the guide plasmids, pCas9-Multi (40 ng) or pAIO-Multi (20 ng), purified DNA of the first sgRNA cassette (4.5 ng) and second sgRNA cassette (8 ng), T4 DNA ligase (200 U), BsmBI (5 U), and ATP (1 mM) were combined in 1×NEB CutSmart reaction buffer (final volume 20 μL) and thermocycled under the following conditions: [5× [37° C. 6:00||6° C. 8:00]15×[55° C. 6:00||6° C. 8:00]]. Assembled plasmids were transformed into electrocompetent cells for subsequent sequencing and testing.

To assemble pCas9-TK1-A, a plasmid containing only one sgRNA cassette, pCas9-GFPT2 was amplified with primers BL566 and BL567, and the resulting product was ligated into pCas9-Multi by Golden Gate Assembly as described above.

To assemble pCas9-hEGFP, a plasmid containing a non-target sgRNA cassette for TK1 experiments, primers BL514 and BL515 were annealed and ligated, by Gibson Assembly, into pCas9-GFPT2 linearized with primers BL464 and BL465.

Construction of pAIO2X pAIO2X GG, the Golden Gate destination plasmid for pAIO2X, is derived from three plasmids, using PCR-generated inserts and multiple steps of cloning by restriction enzyme digest and ligation. Inserts from pSYN36, which contains a codon-optimized superfolder gfp, with a Golden Gate entry site for cloning in sequences that correspond to nucleotides 409-483 of gfp, and pET-22b-ESerGG, which contains an *E. coli* serT gene with a Golden Gate entry site for cloning in sequences that correspond to nucleotides 10-65 of serT, were cloned into pAIO dual guide BsmBI, a version of pAIO-Multi that contains two sgRNA cassettes, with the targeting guide (spacer) sequences replaced by two orthogonal pairs of BsmBI recognition sites that enable guide cloning using annealed primer duplexes.

To create pAIO2X-GFP151/Eser-69 GG, annealed primer duplexes of YZ310/YZ316 and YZ359/YZ360 were ligated into pAIO2X GG using the same Golden Gate Assembly reagents and thermocycling conditions used for UBP cloning, with the exception that BsaI was replaced by BsmBI, each primer duplex was used at a 50:1 insert:plasmid molar ratio with 30 fmol of destination plasmid, and the reaction was scaled by one third to 10 μL. Following assembly, the reaction was not digested with additional enzymes or purified, and was directly transformed into chemically competent *E. coli* DH5α. Following isolation of single plasmid clones and confirmation of the guides by sequencing using primer BL450, the UBPs were cloned into the plasmid by Golden Gate assembly with BsaI, as described in the section, Golden Gate Assembly of UBP-containing plasmids.

Cas9 In Vitro Cleavage Assay

To generate the DNA substrates for in vitro Cas9 cleavage assays, templates BL408, BL409, BL410, BL487, BL488, and BL489 (1 ng per 50 μL reaction) were PCR amplified with primers BL415 (400 nM) and BL416 (400 nM), and OneTaq DNA polymerase in 1× OneTaq standard reaction buffer supplemented with dNaMTP (100 μM), dTPT3TP (100 μM), and $MgCl_2$ (1.5 mM), under the following thermocycling conditions: [25×[95° C. 0:15|56° C. 0:15|68° C. 1:30]].

To generate the DNA templates for in vitro transcription of sgRNAs, templates BL318, BL484, BL485, and BL486 (1 ng per 50 μL reaction), which contain the T7 promoter and a CRISPR RNA (crRNA) spacer sequence, were PCR amplified with primers BL472 (200 nM) and BL473 (200 nM), and OneTaq DNA polymerase in 1× OneTaq standard reaction buffer supplemented with $MgCl_2$ (6 mM), under the following thermocycling conditions: [20×[95° C. 0:15|60° C. 0:15|68° C. 1:30]]. DNA from this first PCR reaction (0.5 μL) was then transferred into a second PCR reaction (100 μL) containing primers BL472 (400 nM), BL439 (500 nM), and BL440 (600 nM), and thermocycled under the following conditions: [4×[95° C. 0:15|68° C. 0:15|68° C. 1:30]20×[95° C. 0:15|60° C. 0:15|68° C. 1:30]]. In vitro transcription of the PCR products with T7 RNA polymerase was performed, and transcribed sgRNAs were purified by PAGE, band excision, and extraction (37° C., overnight) into an aqueous solution of NaCl (200 mM) and EDTA (1 mM, pH 7), followed by concentration and purification by ethanol precipitation.

For in vitro cleavage reactions, Cas9 nuclease (125 nM) was incubated with each transcribed sgRNA (125 nM) in 1×Cas9 nuclease reaction buffer for 5 min, then DNA substrate was added and the reaction was incubated (37° C., 10 min). The reaction was quenched with SDS-PAGE loading buffer (62 mM Tris-HCl, 2.5% SDS, 0.002% bromophenol blue, 0.7 M β-mercaptoethanol, and 10% glycerol), heat denatured (95° C., 10 min), and then loaded onto an SDS-PAGE gel. The resulting cleavage bands were quantified by densitometric analysis using ImageJ[31]. For each sgRNA, raw cleavage efficiencies were divided by the maximum cleavage observed for that sgRNA across the set of the six DNA substrates, to account for differences in sgRNA activity and/or minor variations in preparation. Experiments were performed in technical triplicate and averages represent an average of three in vitro cleavage reactions performed in parallel.

In Vivo Plasmid Replication Experiments

Electrocompetent YZ3 cells were prepared by overnight growth in ~5 mL of media supplemented with chloramphenicol, dilution to $OD_{600}$ of 0.02 in the same media (variable volumes, ~10 mL of media per transformation), and growth to $OD_{600}$ of ~0.3-0.4. Cells were then rapidly chilled in an ice water bath with shaking, pelleted (2500×g, 10 min), and washed twice with one culture volume of ice-cold $ddH_2O$. Electrocompetent cells were then resuspended in ice-cold $ddH_2O$ (50 μL per transformation), mixed with a Golden Gate assembled plasmid (~1 μL, ~1 ng) containing the UBP, and transferred to a pre-chilled 0.2 cm gap electroporation cuvette. Cells were electroporated (Gene Pulser II, Bio-Rad) according to the manufacturer's recommendations (voltage 25 kV, capacitor 2.5 μF, resistor 200Ω) then immediately diluted with 950 μL of pre-warmed media supplemented with chloramphenicol. An aliquot (10-40 μL) of this dilution was then immediately diluted 5-fold with the same pre-warmed media, but additionally supplemented with dNaMTP (250 μM) and d5SICSTP (250 μM). The samples were incubated (37° C., 1 h) and then ~15% of the sample was used to inoculate media (final volume 250-300 μL) supplemented with chloramphenicol, carbenicillin, dNaMTP (250 μM) and d5SICSTP (250 μM). Cells were then monitored for growth, collected at the density ($OD_{600}$) indicated in the main text, and subjected to plasmid isolation. Dilutions of the recovery mixture were also spread onto solid media with chloramphenicol and carbenicillin to ascertain transformation efficiencies. Experiments with dNaMTP (150 μM) and dTPT3TP (37.5 μM) were performed analogously.

Experiments with DM1 were performed analogously using media supplemented with streptomycin, with the additional step of inducing transporter expression with IPTG (1 mM, 1 h) prior to pelleting the cells. All media following electrocompetent cell preparation was also supplemented with streptomycin and IPTG (1 mM) to maintain expression of the transporter.

In Vivo Plasmid Replication Experiments with Cas9 (Liquid Culture Only)

Electrocompetent YZ2 cells were transformed with various pCas9 guide plasmids and single clones were used to inoculate overnight cultures. Cells were then grown, prepared and electroporated as described above for YZ3, with the following modifications: all media was additionally supplemented with zeocin (to select for pCas9) and 0.2% glucose, electrocompetent cells were stored in 10% (v/v $ddH_2O$) DMSO at −80° C. until use, and recovery and growth media were supplemented with dNaMTP (250 μM) and dTPT3TP (75 μM). Varying concentrations of IPTG (0-100 μM) were added to the growth media (but not the recovery media) to induce Cas9 expression. The sgRNAs corresponding to the d(AXT) sequence are the non-target guides for all sequences except for the d(AXT)-containing sequence itself, the non-target guides for which correspond to the d(GXT) sequence and all experiments with non-target sgRNAs were conducted with the addition of IPTG (10 μM) to the growth media. For growth and regrowth experiments, cells were grown to an $OD_{600}$ of 3.5-4.0, then diluted 1:250 and regrown to an $OD_{600}$ of 3.5-4.0, after which plasmids were isolated.

In Vivo Plasmid Replication Experiments with Cas9 (Plating and Liquid Culture)

Electrocompetent YZ4 cells were grown, prepared and electroporated as described above for YZ2, with the following modifications: media for growing cells prior to electroporation only contained chloramphenicol (i.e. no zeocin), zeocin was used to select for pAIO (i.e. no carbenicillin), and recovery and growth media were supplemented with dNaMTP (150 μM) and dTPT3TP (37.5 μM). Following transformation with pAIO, dilutions of the recovery mixture were spread onto solid media containing chloramphenicol, zeocin, dNaMTP (150 μM), dTPT3TP (37.5 μM), 0.2% glucose, and various concentrations of IPTG (0-50 μM). Following overnight growth (37° C., ~14 h), individual colonies were used to inoculate liquid media of the same composition as the solid media. Experiments performed with pAIO2X were conducted as described above for YZ4 without using frozen electrocompetent cells or glucose. The second plating depicted in FIG. 4 was performed by streaking cells from liquid culture onto solid media of the same composition as the liquid media, and growth at 37° C. (~14 h). Six random colonies were selected to continue propagation in liquid culture.

Cell Doubling Calculation

Cell doublings for liquid culture growth-dilution-regrowth experiments were calculated by $\log_2$ of the dilution factor (30,000 or 300,000) between growths, except for growths inoculated from a plated colony, the cell doublings for which were calculated by averaging, for each individual clone, the time from inoculation to target $OD_{600}$ (9.4±1.1 h (1 SD) for the first plating inoculation, 10.2±3 h for the second plating inoculation) and dividing these averages by an estimated doubling time of 40 min. Growth times varied for each clone because colonies were isolated when they were barely visible to the naked eye, and thus it was not attempted to control for variability in the number of cells inoculated into the liquid cultures. Note that the reported cell doublings was only an estimate of doublings in liquid culture, which underreported the total number of cell doublings, as it was not attempted to estimate the number of cell doublings that occurred during each of the growths on solid media.

Biotin Shift Assay

The retention of the UBP(s) in isolated plasmids was determined and validated as follows: plasmid minipreps or Golden Gate assembled plasmids (0.5·L, 0.5-5 ng/μL), or dNaM-containing oligonucleotides (0.5 fmol), were PCR amplified with dNTPs (400 μM), 1× SYBR Green, $MgSO_4$ (2.2 mM), primers (10 nM each), d5SICSTP (65 μM), $dMMO2^{Bio}TP$ (65 μM), OneTaq DNA polymerase (0.018 U/μL), and DeepVent DNA polymerase (0.007 U/μL) in 1× OneTaq standard reaction buffer (final volume 15 μL), under the following thermocycling conditions: [20×[95° C. 0:15|x° C. 0:15|68° C. 4:00]]; see Table 2 for a list of primers and their corresponding annealing temperatures used in this assay. After amplification, 1 μL of each reaction was mixed with streptavidin (2.5 μL, 2 μg/μL, Promega) and briefly incubated at 37° C. After incubation, samples were mixed with loading buffer and run on a 6% polyacrylamide (29:1 acrylamide:bis-acrylamide) TBE gel, at 120 V for ~30 min. Gels were then stained with 1×SYBR Gold dye (Thermo Fisher) and imaged using a Molecular Imager Gel Doc XR+(Bio-Rad) equipped with a 520DF30 filter (Bio-Rad).

Calculation of UBP Retention

Figure 7A:
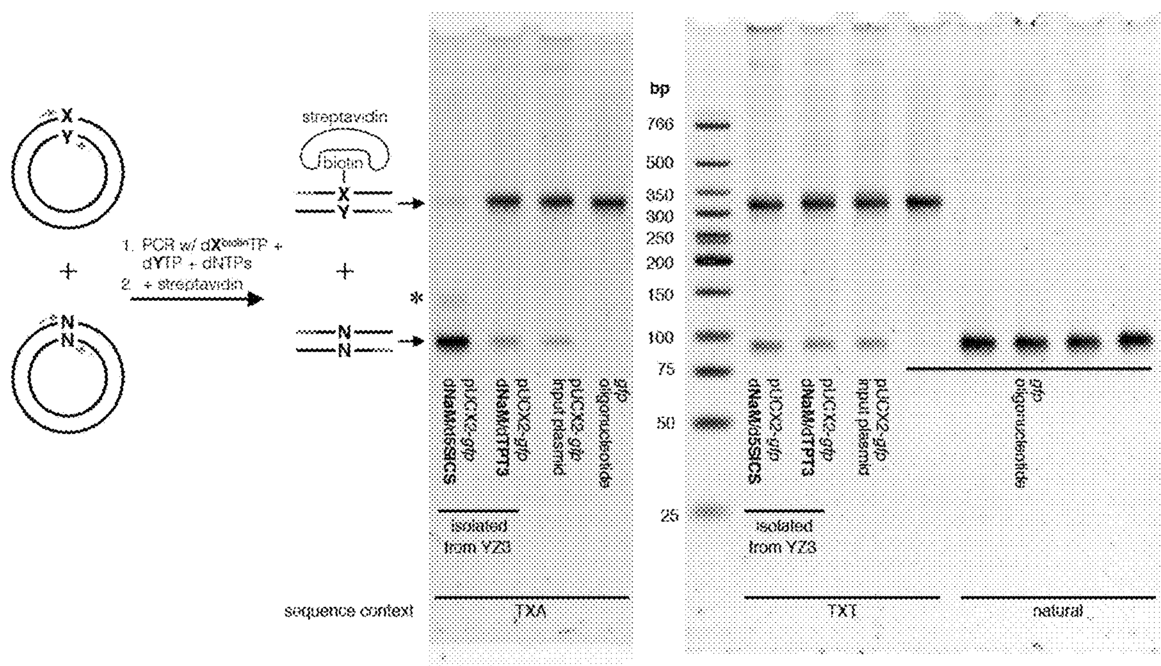
FIG. 7A-FIG. 7B illustrate biotin shift assay gels.
Figure 7B:
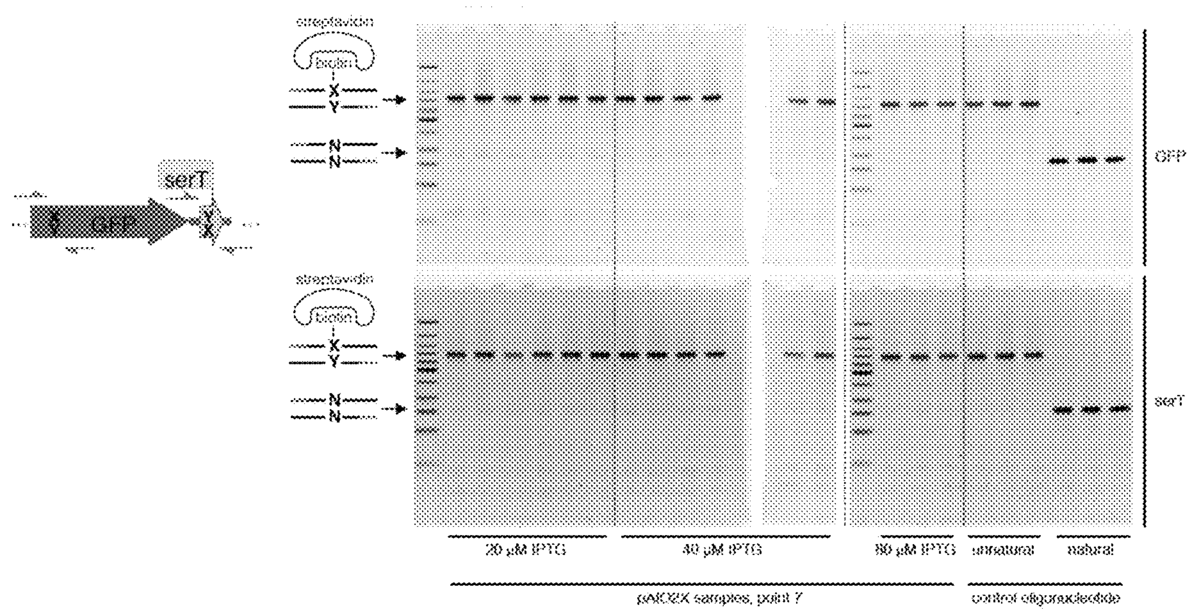

UBP retention was assessed by densitometric analysis of the gels (ImageJ or Image Studio Lite, LICOR) from the biotin shift assay and calculation of a percent raw shift, which equals the intensity of the streptavidin-shifted band divided by the sum of the intensities of the shifted and unshifted bands. See FIG. 7 for representative gels. Reported UBP retentions are normalized values.

Unless otherwise indicated, for experiments not involving plating on solid media, UBP retention was normalized by dividing the percent raw shift of each propagated plasmid sample by the percent raw shift of the Golden Gate assembled input plasmid. It was assumed that the starting UBP content of the cellular plasmid population was equivalent to the UBP content of the input plasmid, based on direct inoculation of the transformation into liquid culture. Thus, in these experiments, normalized UBP retention was a relative value that related the UBP content of the propagated plasmid population to the UBP content of the starting population, which was not 100% due to loss during the PCR used to generate the insert for input plasmid assembly (FIG. 7).

For experiments involving plating on solid media, UBP retention was normalized by dividing the percent raw shift of each propagated plasmid sample by the percent raw shift of the dNaM-containing oligonucleotide template used in the assembly of the input plasmid. Plating enabled clonal isolation of UBP-containing plasmids from fully natural plasmids that arose during plasmid construction (some of which may contain sequences that were not recognized by the sgRNA(s) employed). Because there was no PCR-mediated loss of the UBP in the oligonucleotide template, normalization to the oligonucleotide template was a better indicator of absolute UBP retention than normalization to the input plasmid. Under the conditions used in the biotin shift assay, most oligonucleotide templates and sequence contexts gave >90% raw shift, with <2% shift for a cognate fully natural template (i.e. UBP misincorporation during the biotin shift assay was negligible).

Plating allowed for the differentiation between UBP loss that occurred in vivo from loss that occurred in vitro, with the exception of clonally-derived samples that gave <2% shift, for which it was unable to differentiate between whether the UBP was completely lost in vivo or if the sample came from a transformant that originally received a fully natural plasmid. Such samples were excluded from reported average values when other samples from the same transformation give higher shifts.

Biotin Shift Depletion and In Vivo Mutation Analysis

To determine the mutational spectrum of the UBP in isolated plasmid samples, biotin shift assays were performed as described above. Non-shifted bands, which corresponded to natural mutations of the UBP-containing sequences, were excised and extracted (37° C., overnight) into a minimal amount of an aqueous solution of NaCl (200 mM) and EDTA (1 mM, pH 7), followed by concentration and purification by ethanol precipitation. A sample of extract (1 μL) was PCR amplified under standard conditions (natural dNTPs only), with OneTaq DNA polymerase and the same primers used for the biotin shift PCR, and the resulting products were sequenced by Sanger sequencing.

Functional Characterization of a Mutant PtNTT2 Transporter

Figure 1B:
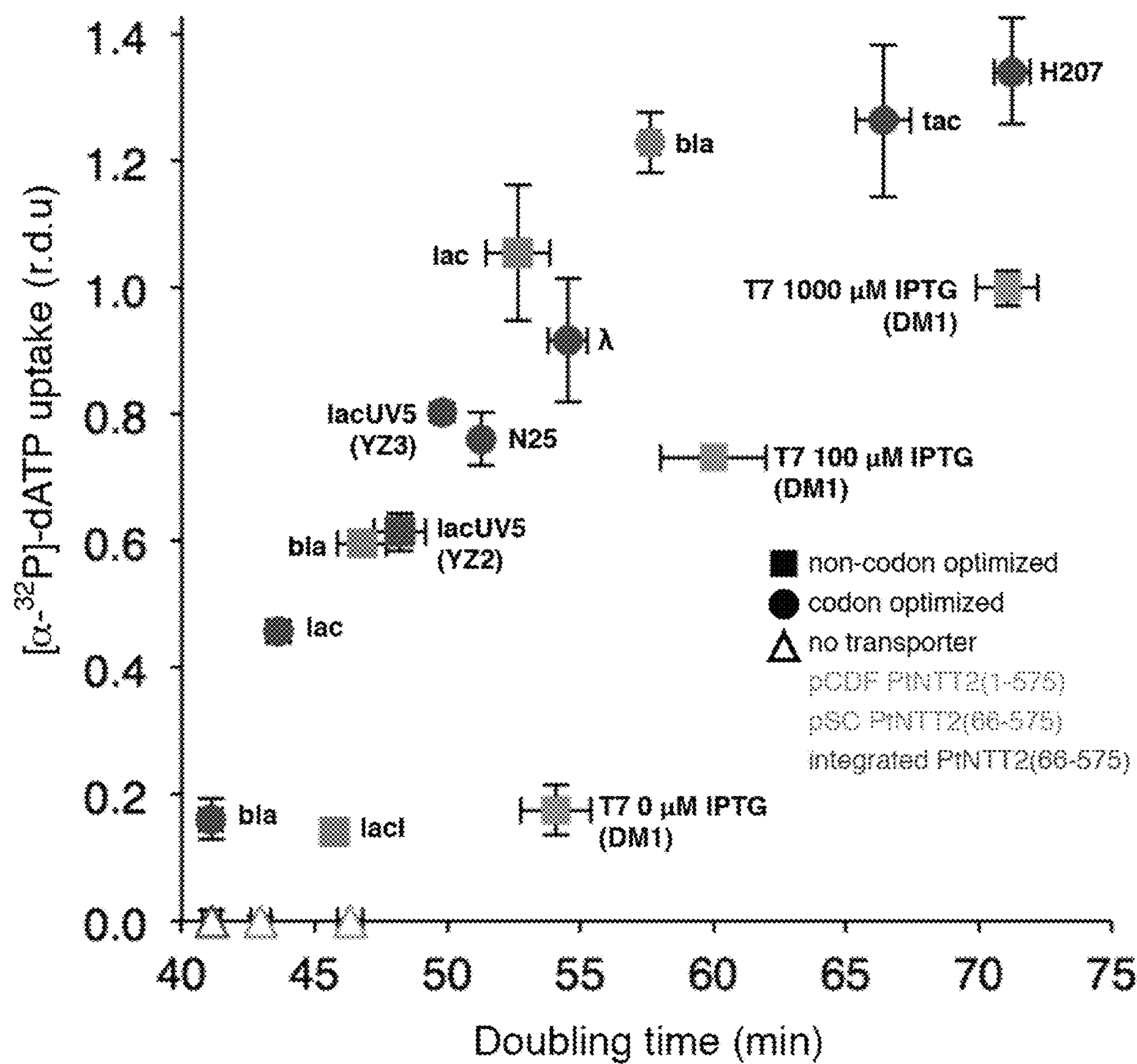
Figure 5A:
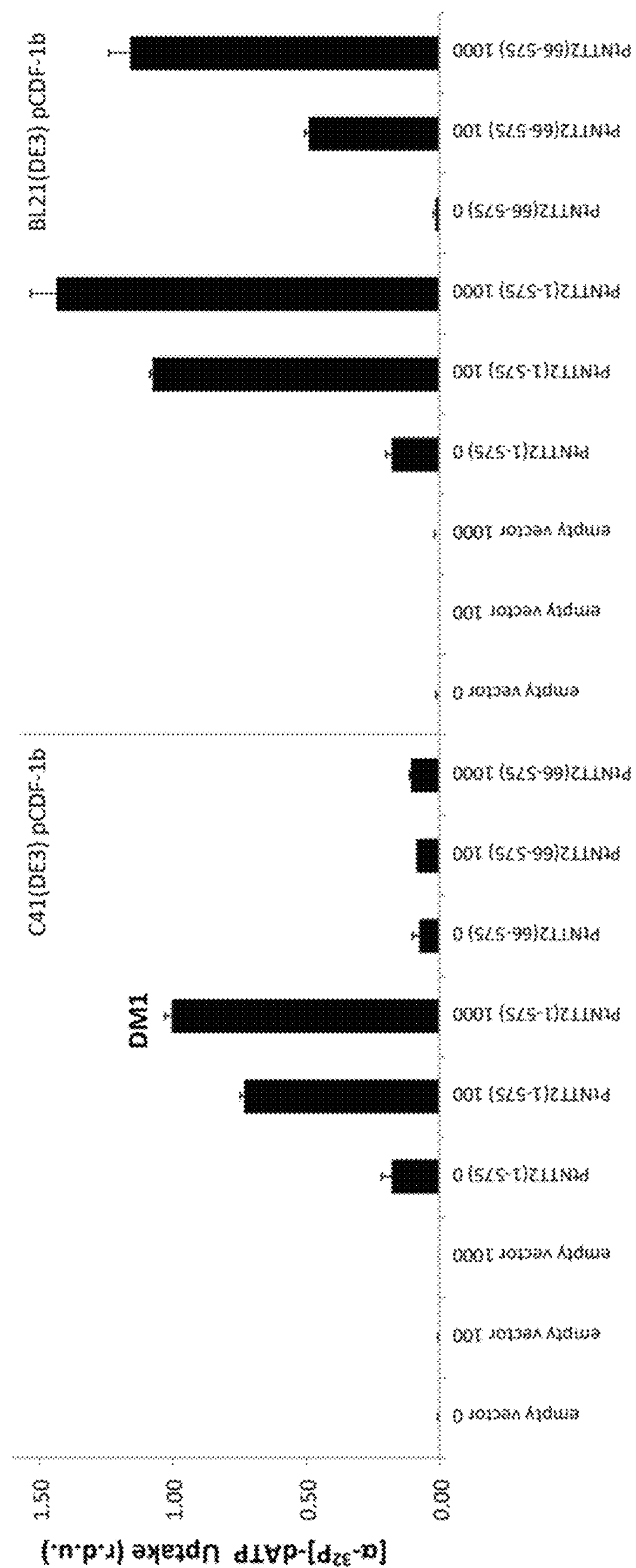
FIG. 5A-FIG. 5F illustrate dATP uptake and growth of cells expressing PtNTT2 as a function of inducer (IPTG) concentration or promoter strength, strain background and presence of N-terminal signal sequences.
Figure 5B:
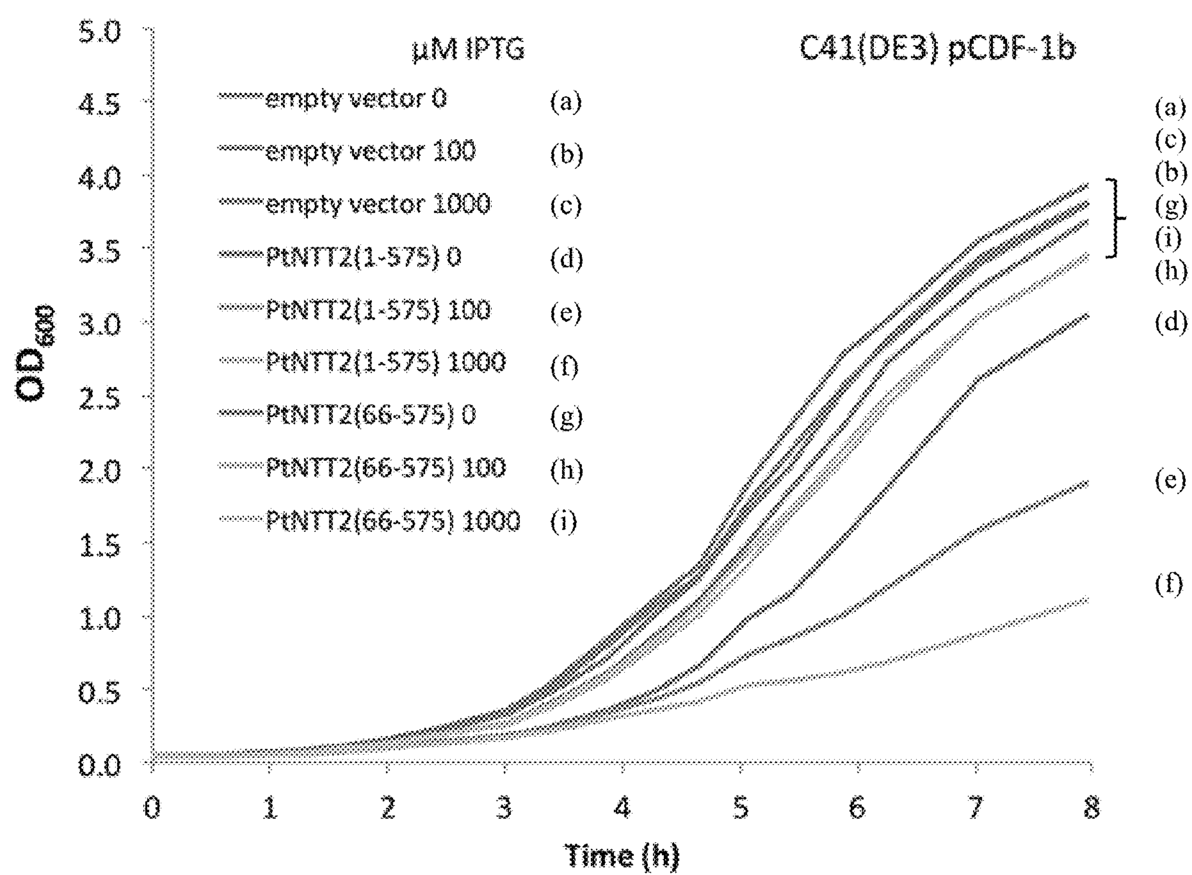
Figure 5C:
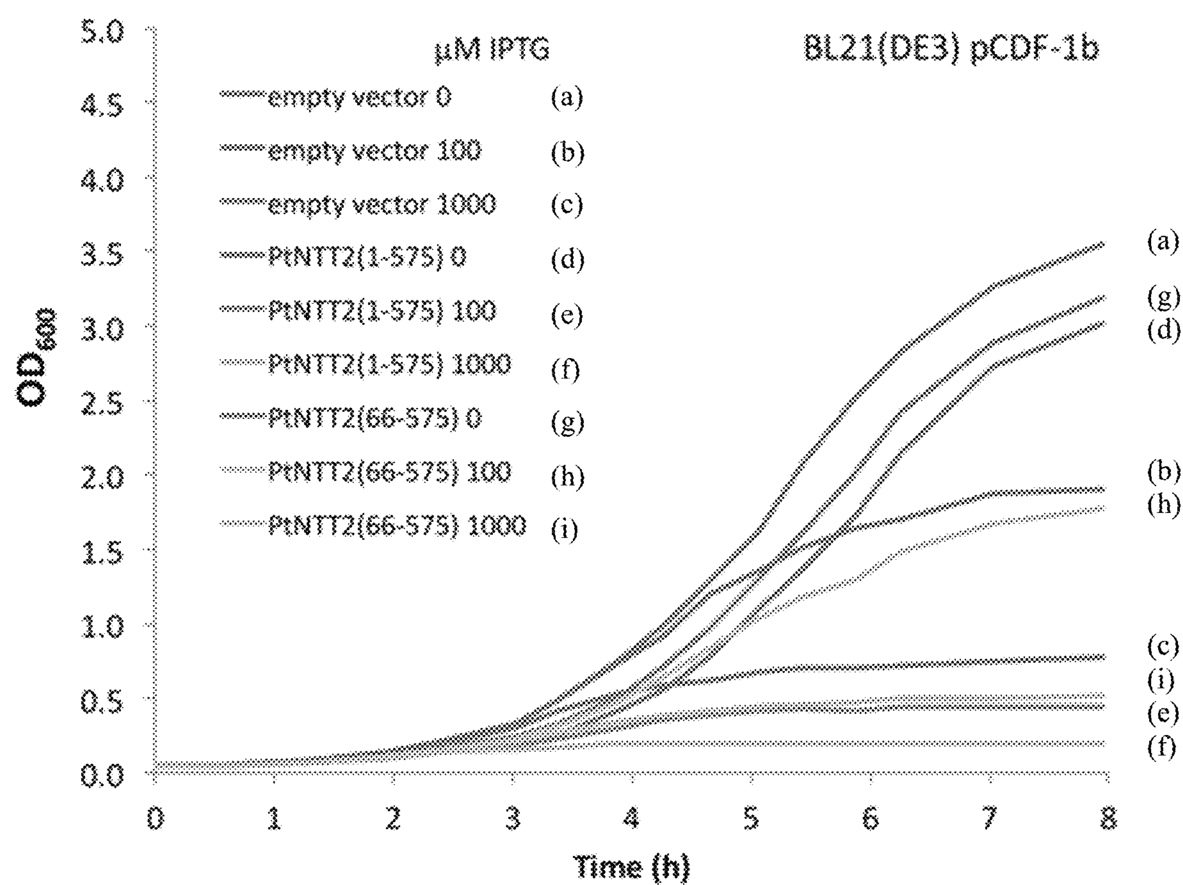

Expression of the nucleoside triphosphate transporter from *Phaeodactylum tricornutum* (PtNTT2) in *E. coli* enabled the import of dNaMTP and d5SICSTP and the subsequent replication of the dNaM-d5SICS UBP (FIG. 1A), but its expression was also toxic (FIG. 1B). In SSO referred to herein as DM1, the transporter was expressed from a T7 promoter on a multicopy plasmid (pCDF-1b) in *E. coli* C41(DE3), and its induction was controlled due to the associated toxicity. In its native algal cell, PtNTT2's N-terminal signal sequences direct its subcellular localization and are removed by proteolysis. In some cases in the *E. coli* system, the N-terminal signal was retained, and contributed to the observed toxicity. Removal of amino acids 1-65 and expression of the resulting N-terminally truncated variant PtNTT2(66-575) in *E. coli* C41(DE3) resulted in lower toxicity relative to the full length PtNTT2, but also reduced uptake of [α-$^{32}$P]-dATP (FIG. 5A and FIG. 5B), possibly due to reduced expression. Expression of PtNTT2(66-575) in *E. coli* BL21(DE3) resulted in increased levels of [α-$^{32}$P]-dATP uptake with little increase in toxicity relative to an empty vector control (FIG. 5A and FIG. 5C), but the higher level of T7 RNAP in this strain was itself toxic (FIG. 5A and FIG. 5C).

Constitutive expression of PtNTT2(66-575) from a low copy plasmid or a chromosomal locus was explored, to eliminate the need to produce toxic levels of T7 RNAP, and to impart the SSO with greater autonomy, more homogeneous transporter expression and triphosphate uptake across a population of cells, and ultimately improve UBP retention. Expression of PtNTT2(66-575) in *E. coli* BL21(DE3) was explored with the *E. coli* promoters $P_{lacI}$, $P_{bla}$, and $P_{lac}$ from a pSC plasmid, and with $P_{bla}$, $P_{lac}$, $P_{lacUV5}$, $P_{H207}$, $P_{\lambda}$, $P_{tac}$, and $P_{N25}$ from the chromosomal lacZYA locus (see Table 2). The use of a codon-optimized variant of the truncated transporter was also explored (see Table 2). Although uptake of [α-$^{32}$P]-dATP was negatively correlated with doubling time, each strain exhibited an improved ratio of uptake to fitness compared to DM1 (FIG. 1B). Strain YZ3, which expressed the codon-optimized, chromosomally integrated PtNTT2(66-575) from the $P_{lacUV5}$ promoter, exhibited both robust growth (<20% increased doubling time relative to the isogenic strain without the transporter), and reasonable levels of [α-$^{32}$P]-dATP uptake, and was selected for further characterization.

Figure 2A:
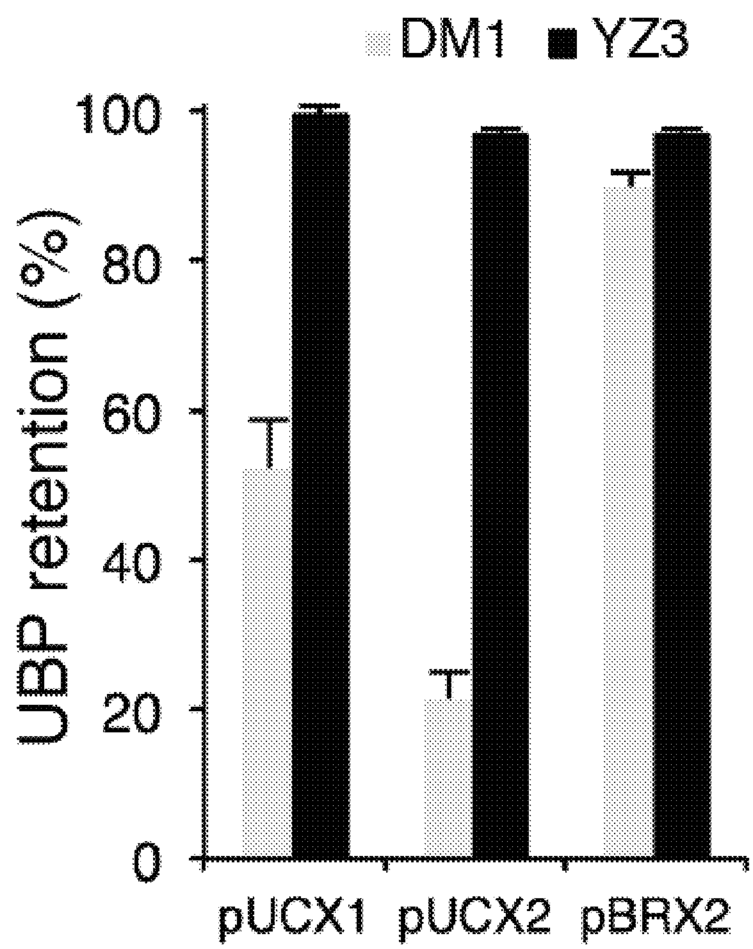
FIG. 2A-FIG. 2B illustrate increased UBP retention resulting from transporter and UBP optimization.
Figure 6:
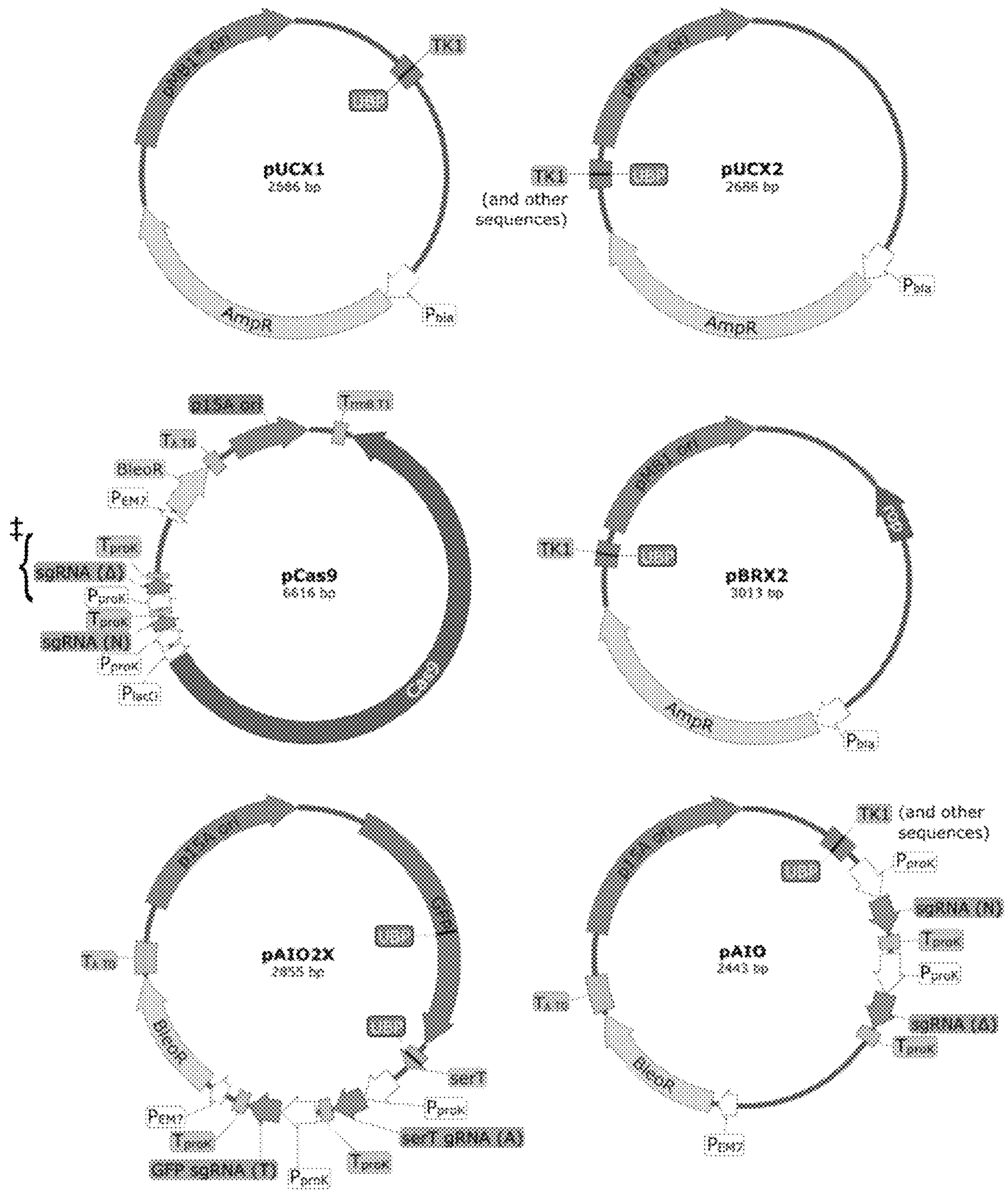
FIG. 6 shows plasmid maps. Promoters and terminators are denoted by white and gray features, respectively. * denotes the derivative of the pMB1 origin from pUC19, which contains a mutation that increases its copy number. Plasmids that contain a UBP are generally indicated with the TK1 sequence (orange), but as described in the text and indicated above, pUCX2 and pAIO variants with other UBP-containing sequences also position the UBP in the approximate locus shown with TK1 above. sgRNA (N) denotes the guide RNA that recognizes a natural substitution mutation of the UBP, with N being the nucleotide present in the guide RNA. sgRNA (Δ) denotes the guide RNA that recognizes a single base pair deletion of the UBP; this and its associated promoter and terminator (indicated by ‡) are only present in certain experiments. The serT and gfp genes do not have promoters.
Figure 8A:
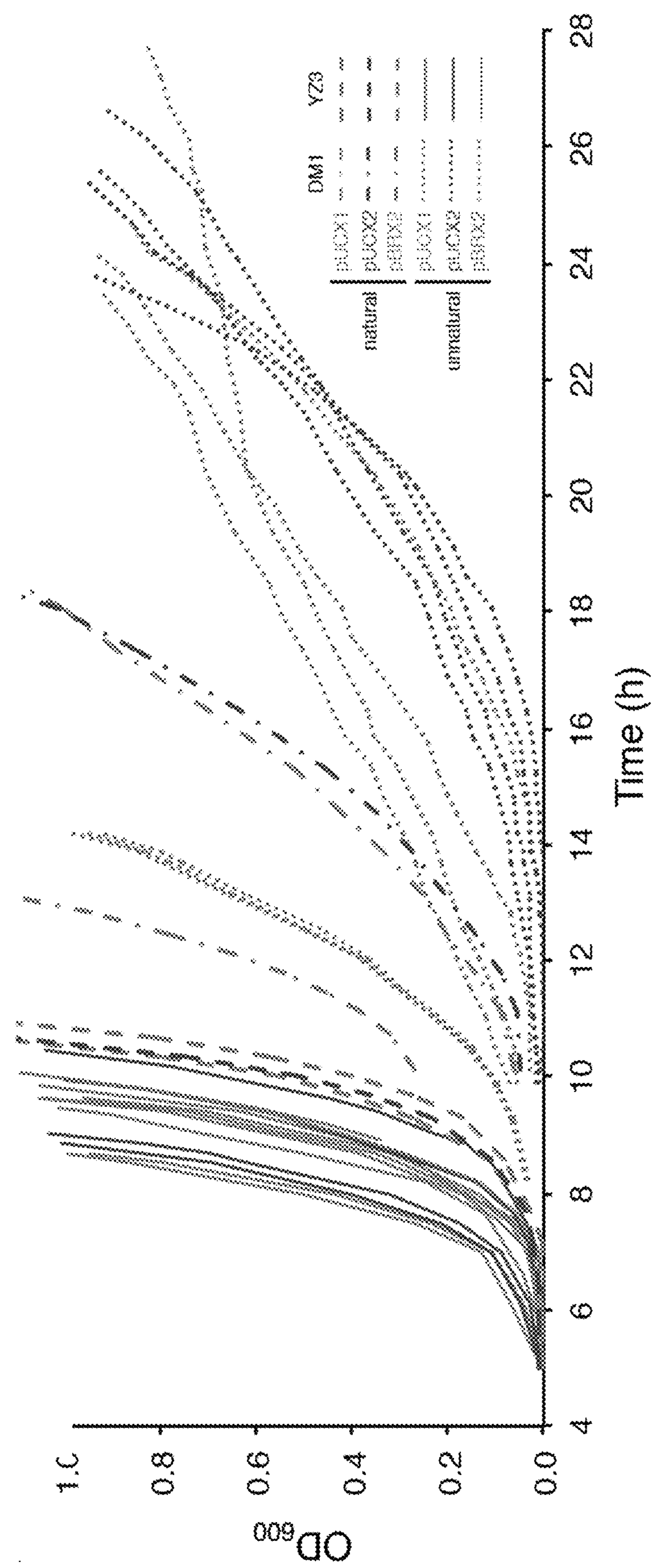

To determine whether the optimized transporter system of YZ3 facilitates high UBP retention, three plasmids that position the UBP within the 75-nt TK1 sequence were constructed (with a local sequence context of d(A-NaM-T)). These include two high copy pUC19-derived plasmids, pUCX1 and pUCX2, as well as one low copy pBR322-derived plasmid, pBRX2 (FIG. 6). In addition to examine the effect of copy number on UBP retention, these plasmids positioned the UBP at proximal (pUCX1) and distal (pUCX2 and pBRX2) positions relative to the origin of replication. *E. coli* YZ3 and DM1 were transformed with pUCX1, pUCX2, or pBRX2 and directly cultured in liquid growth media supplemented with dNaMTP and d5SICSTP (and IPTG for DM1 to induce the transporter), and growth and UBP retention were characterized (at an $OD_{600}$ of ~1) (see Methods and FIG. 7A). While DM1 showed variable levels of retention and reduced growth with the high copy plasmids, YZ3 showed uniformly high levels of UBP retention and robust growth (FIG. 2*a* and FIG. 8A).

Figure 2B:
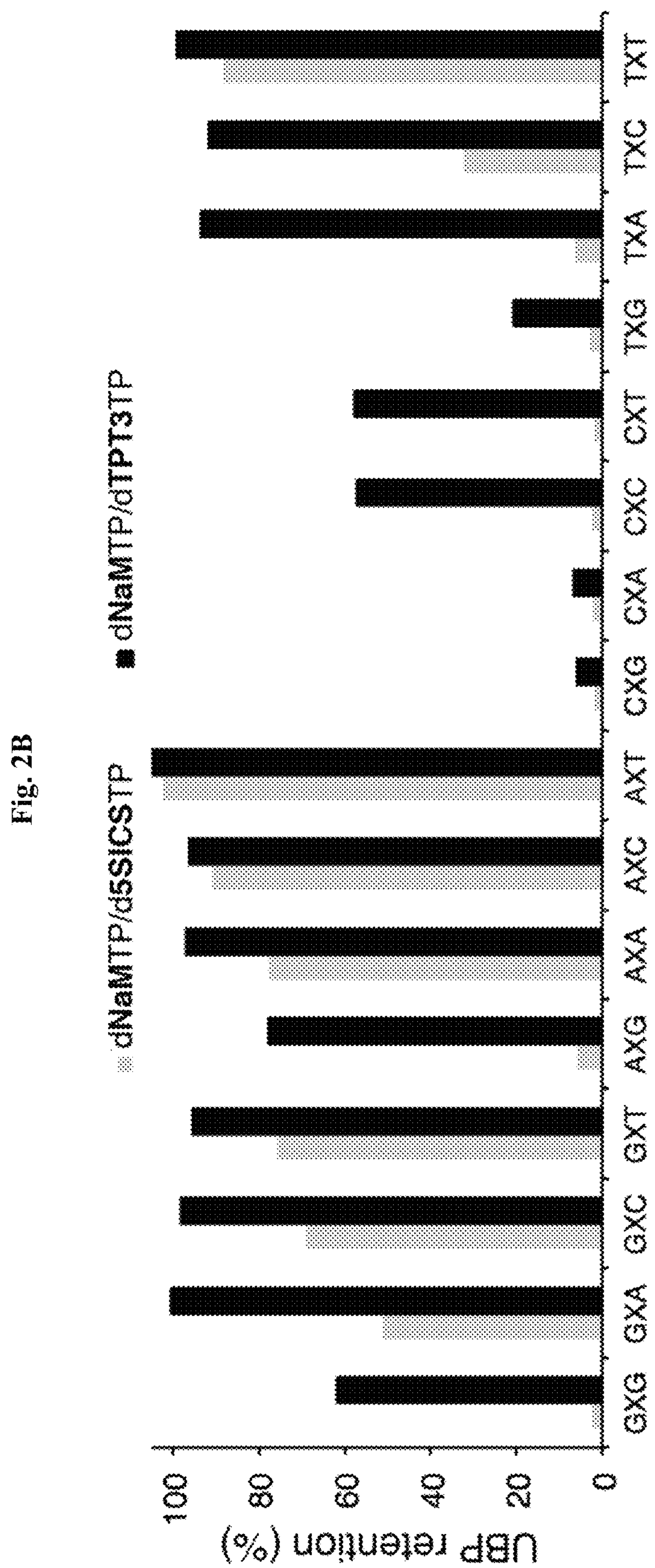

To explore the effect of local sequence context on UBP retention in YZ3, sixteen pUCX2 variants were constructed in which the UBP was flanked by each possible combination of natural base pairs within a fragment of gfp (see Table 2). Under the same growth conditions as above, a wide range of UBP retentions was observed, with some sequence contexts showing complete loss of the UBP (FIG. 2B). However, since the development of DM1 with the dNaM-d5SICS UBP, it was determined that ring contraction and sulfur derivatization of d5SICS, yielding the dNaM-dTPT3 UBP (FIG. 1A), resulted in more efficient replication in vitro. To explore the in vivo use of dNaM-dTPT3, the experiments were repeated with YZ3 and each of the sixteen pUCX2 plasmids but with growth in media supplemented with dNaMTP and dTPT3TP. UBP retentions were clearly higher with dNaM-dTPT3 than with dNaM-d5SICS (FIG. 2B).

Figure 3A:
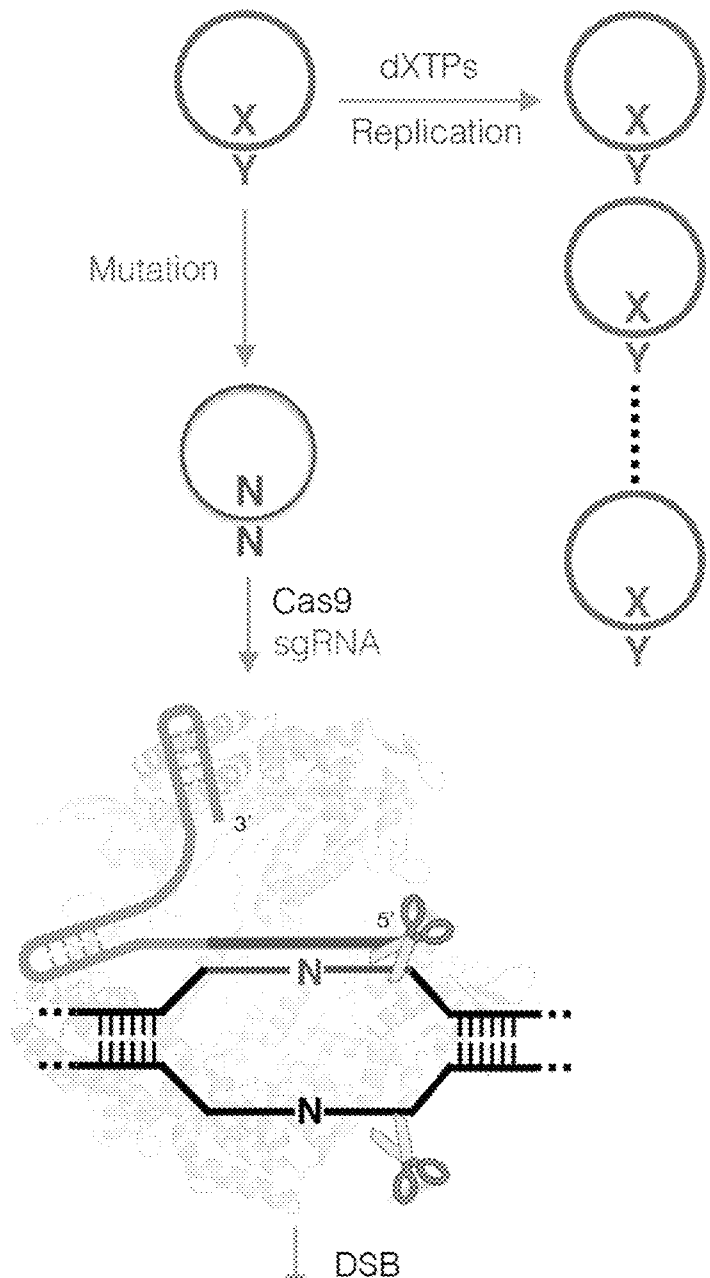
FIG. 3A-FIG. 3C illustrate the Cas9-based editing system.
Figure 5D:
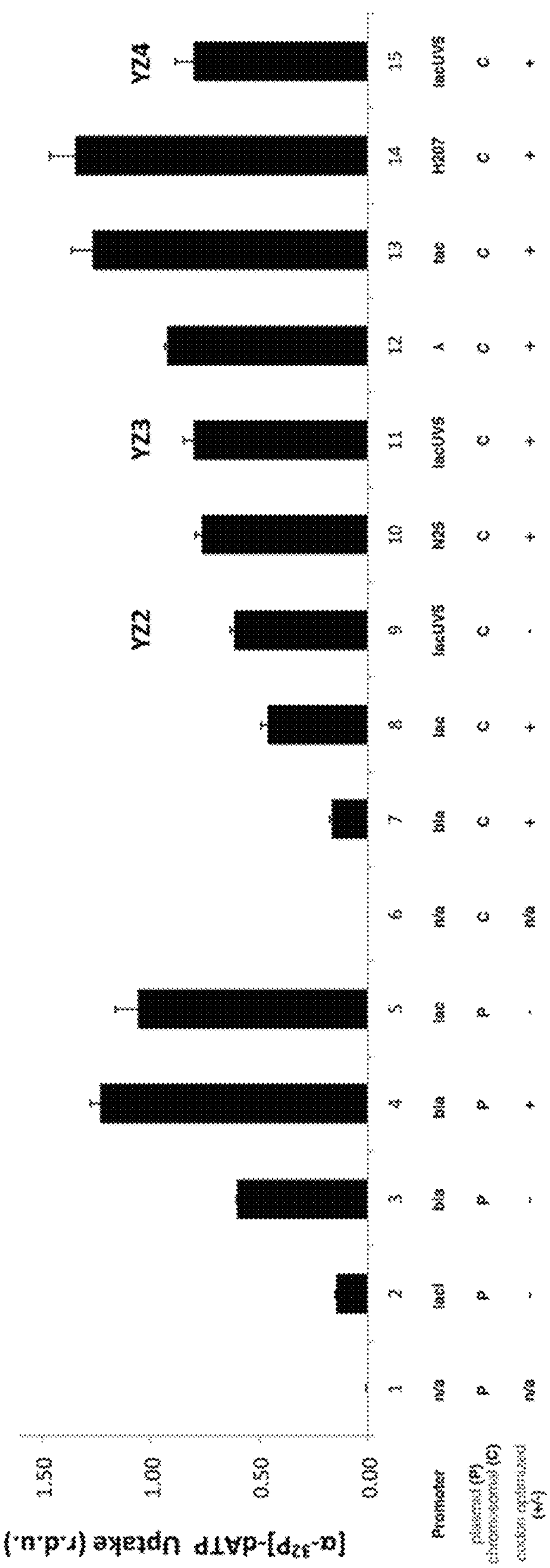
Figure 5E:
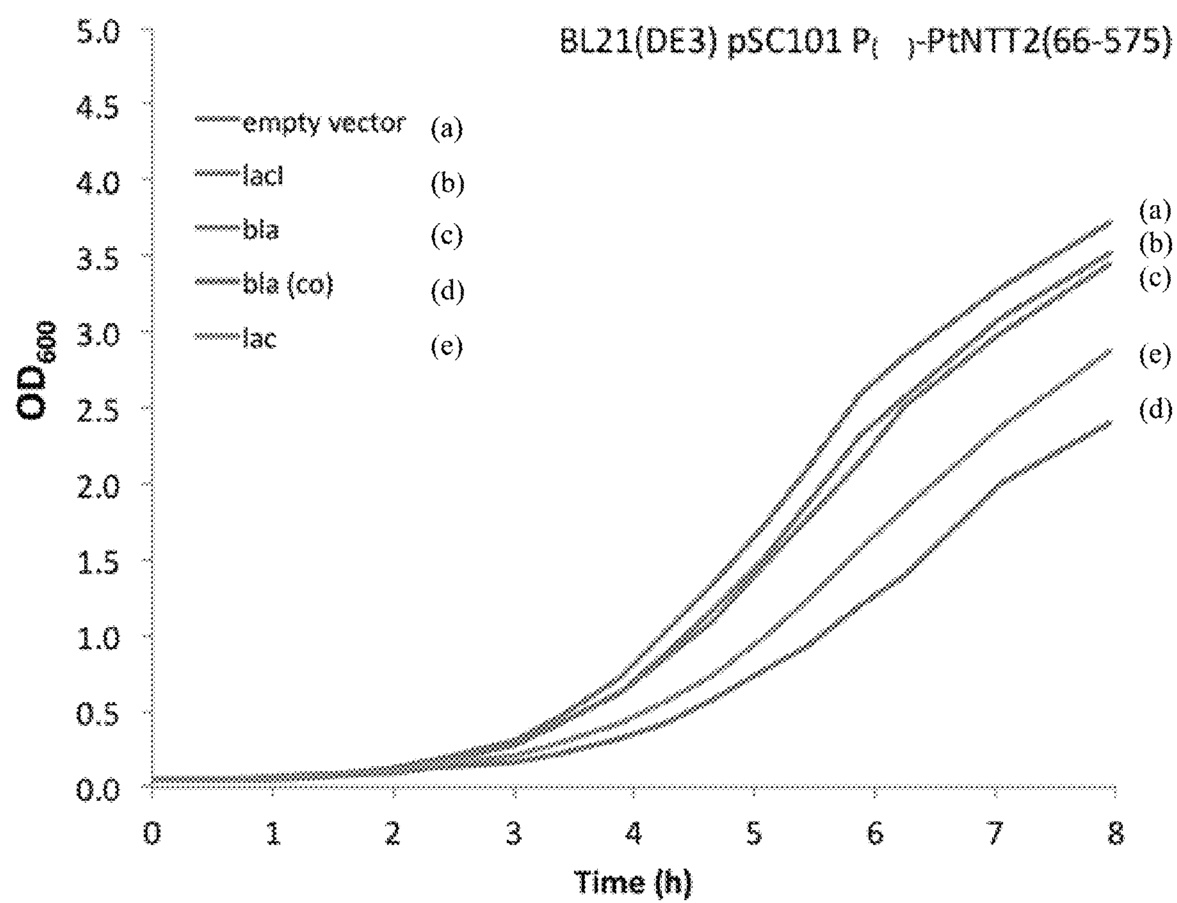
Figure 5F:
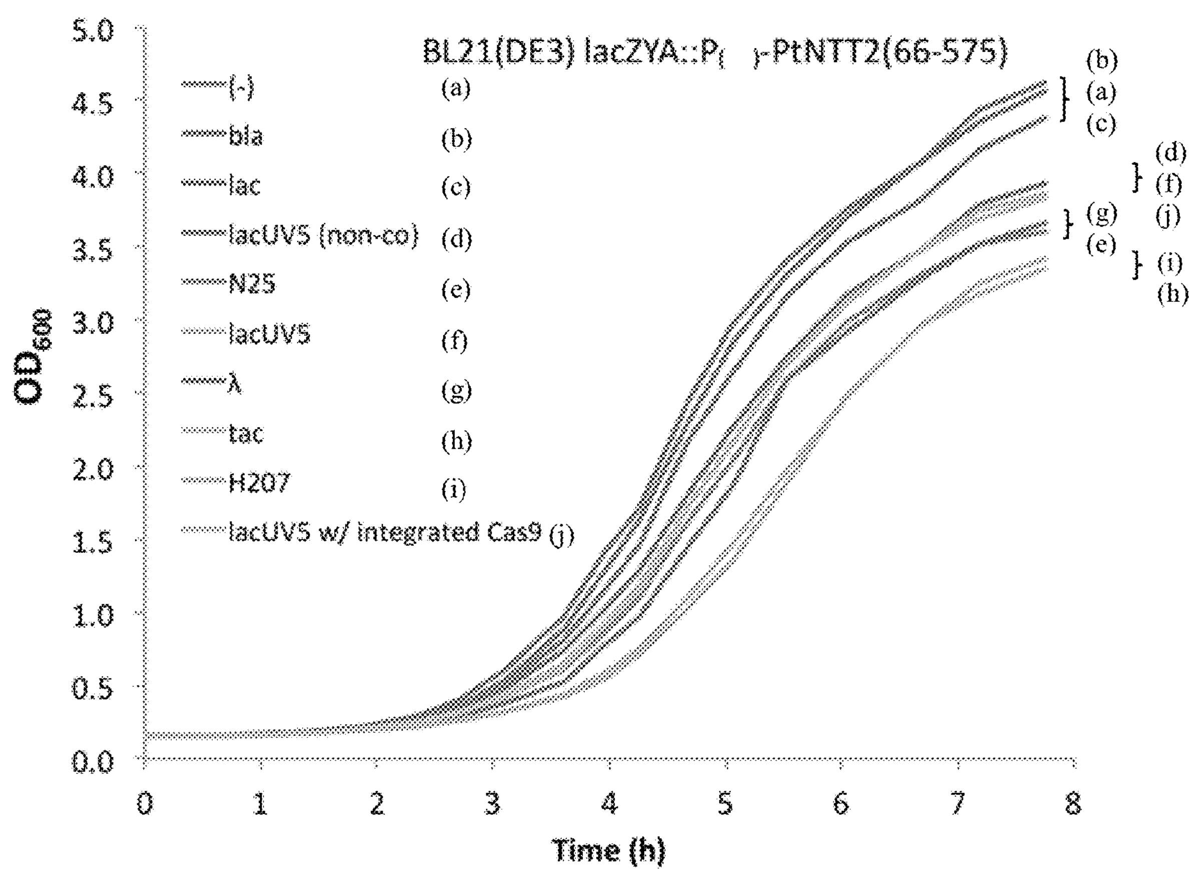
Figure 9A:
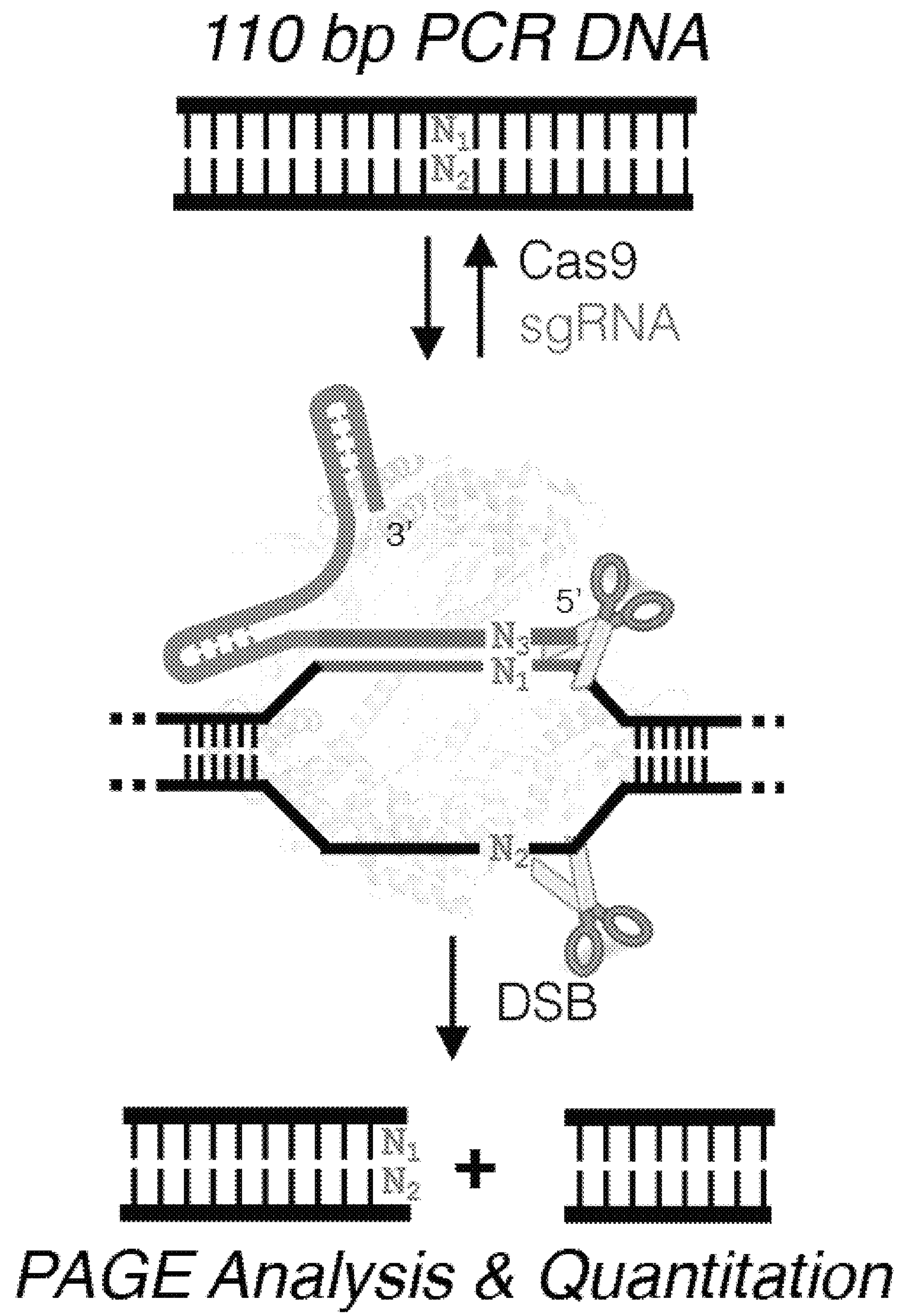
Figures 10A, 10B:
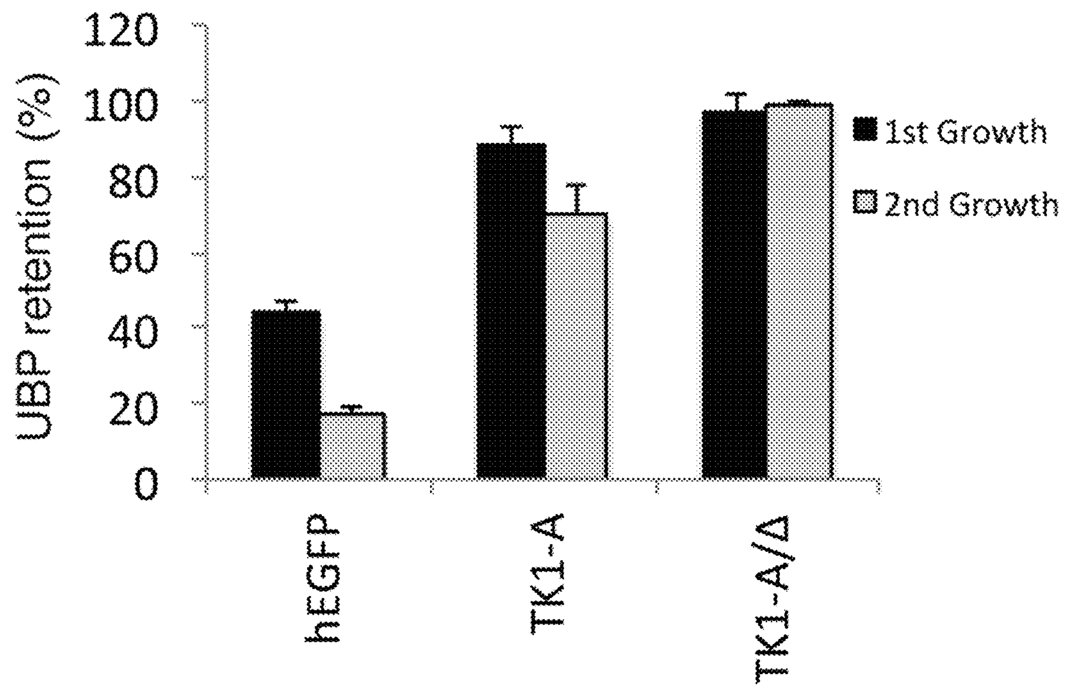
FIG. 10A-FIG. 10D show Cas9-mediated immunity to UBP loss in TK1.
Figure 10C:
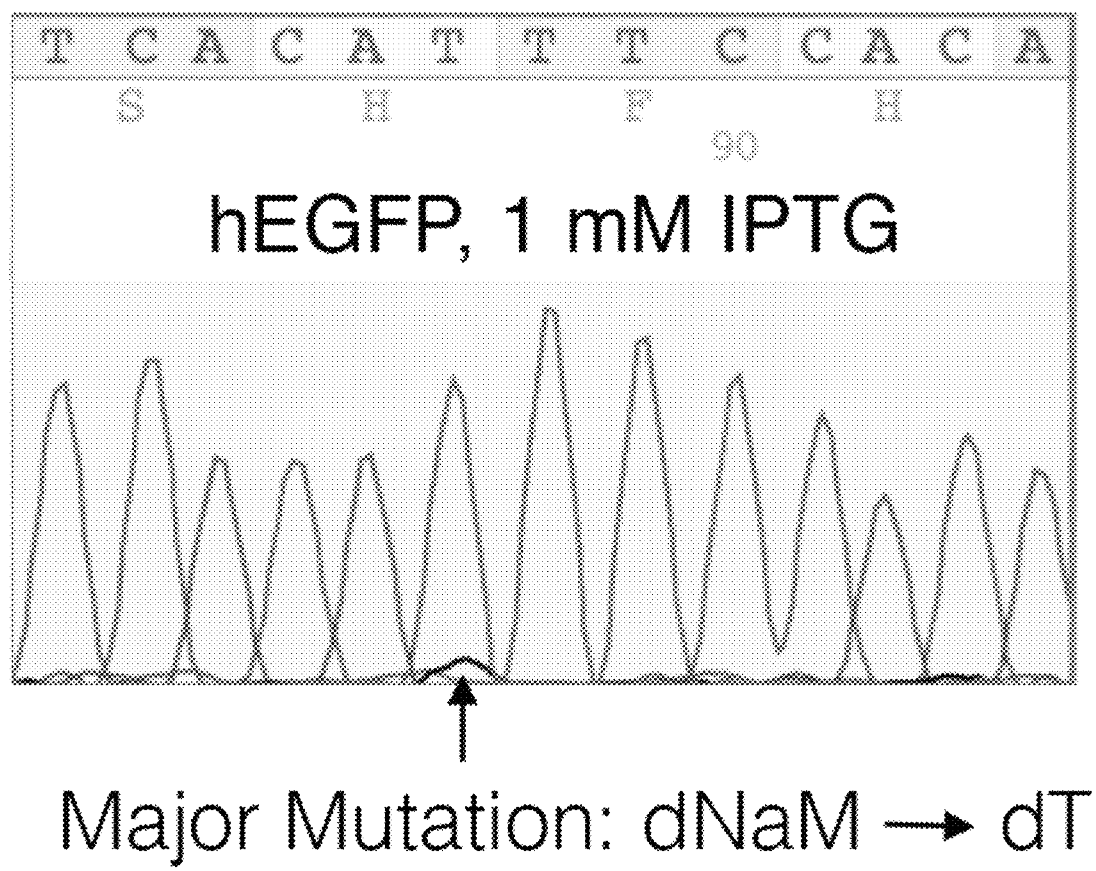
Figure 10D:
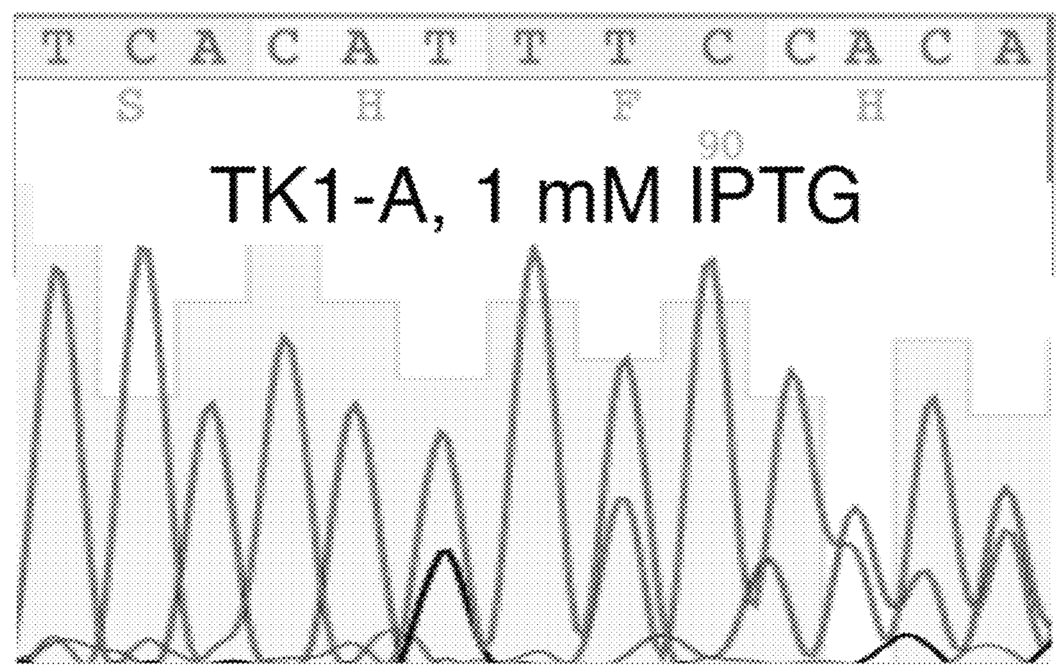

While dNaM-dTPT3 is a more optimal UBP for the SSO than dNaM-d5SICS, its retention is still moderate to poor in some sequences. Moreover, several sequences that show good retention in YZ3 cultured in liquid media show poor retention when growth includes culturing on solid media (FIG. 8B). To further increase UBP retention with even these challenging sequences and/or growth conditions, selective elimination of plasmids was carried out that lose the UBP. In prokaryotes, the clustered regularly interspaced short palindromic repeats (CRISPR)/CRISPR-associated (Cas) system provides adaptive immunity against viruses and plasmids. In type II CRISPR-Cas systems, such as that from *Streptococcus pyogenes*, the endonuclease Cas9 utilizes encoded RNAs (or their artificial mimics known as single-guide RNAs (sgRNAs)) to introduce double-strand breaks into complementary DNA upstream of a 5'-NGG-3' protospacer adjacent motif (PAM) (FIG. 3A), which then results in DNA degradation by exonucleases. In vitro, it was found that the presence of a UBP in the target DNA generally reduces Cas9-mediated cleavage relative to sequences that are fully complementary to the provided sgRNA (FIG. 9). In some instances within a cell, Cas9 programmed with sgRNA(s) complementary to natural sequences that arise from UBP loss would enforce retention in a population of plasmids, which was refer to as immunity to UBP loss. To test this, a p15A plasmid was used to construct pCas9, which expresses Cas9 via an IPTG-inducible LacO promoter, as well as an 18-nt sgRNA that is complementary to the TK1 sequence containing the most common dNaM-dTPT3 mutation (dT-dA) via the constitutive ProK promoter (FIGS. 6 and 10A). Strain YZ2 (a forerunner of YZ3 with slightly less optimal transporter performance; FIG. 1A, FIG. 5D, and FIG. 5F) carrying the pCas9 plasmid was transformed with the corresponding pUCX2 plasmid (i.e. the pUCX2 variant with the UBP embedded within the TK1 sequence such that loss of the UBP produces a sequence targeted by the sgRNA encoded on pCas9), grown to an $OD_{600}$ of ~4, diluted 250-fold, and regrown to the same $OD_{600}$. UBP retention in control experiments with a non-target sgRNA dropped to 17% after the second outgrowth; in contrast UBP retention in the presence of the correct sgRNA was 70% (FIG. 10B). Sequencing revealed that the majority of plasmids lacking a UBP when the correct sgRNA was provided contained a single nucleotide deletion in its place, which was not observed with the non-target sgRNA (FIG. 10C, and FIG. 10D). With a pCas9 plasmid that expresses two sgRNAs, one targeting the most common substitution mutation and one targeting the single nucleotide deletion mutation (FIG. 6), and the same growth and regrowth assay, loss of the UBP was undetectable (FIG. 10B).

Figure 3B:
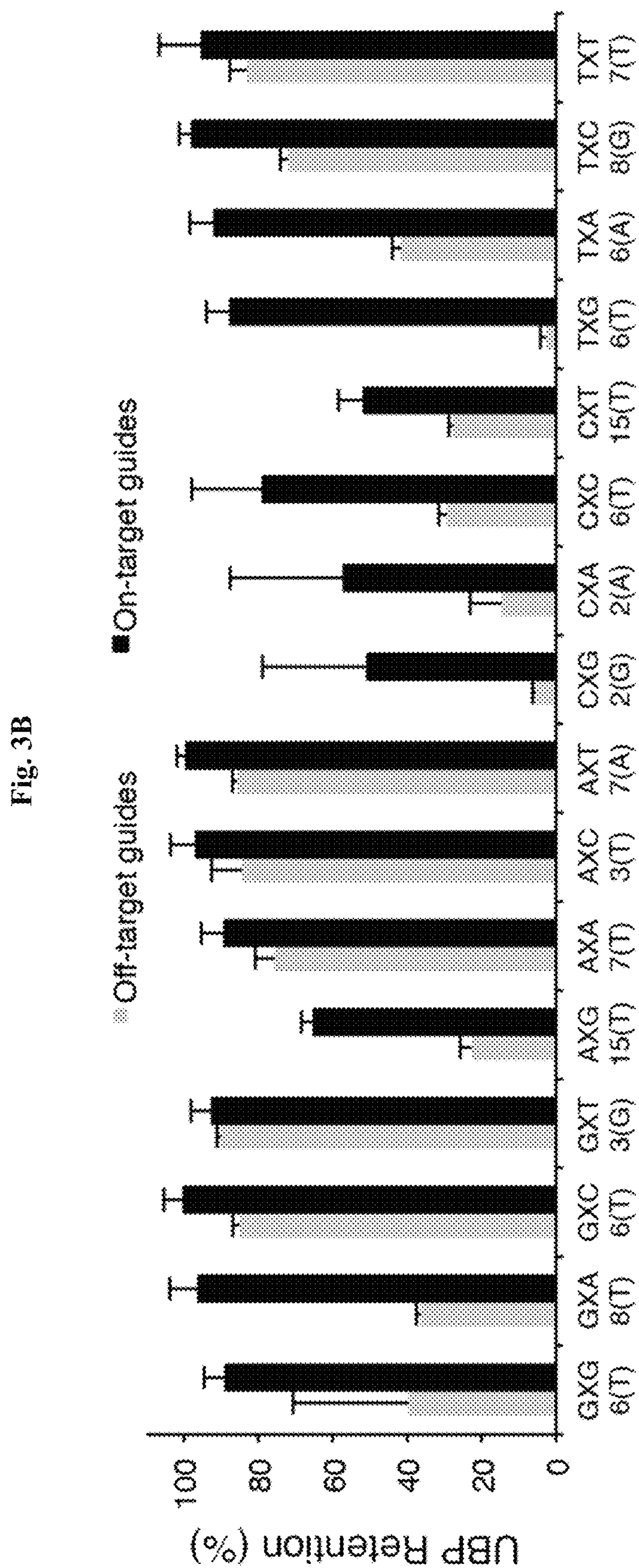

To more broadly explore Cas9-mediated immunity to UBP loss, retention was examined using sixteen pUCX2 variants with sequences that flank the UBP with each possible combination of natural base pairs, but also vary its position relative to the PAM, and vary which unnatural nucleotide is present in the strand recognized by the sgRNAs (FIG. 11). A corresponding set of sixteen pCas9 plasmids was also constructed that express two sgRNAs, one targeting a substitution mutation and one targeting the single nucleotide deletion mutation, for each pUCX2 variant. Strain YZ2 carrying a pCas9 plasmid was transformed with its corresponding pUCX2 variant and grown in the presence of the unnatural triphosphates and IPTG (to induce Cas9), and UBP retention was assessed after cells reached an $OD_{600}$ of ~1. As a control, the sixteen pUCX2 plasmids were also propagated in YZ2 carrying a pCas9 plasmid with a non-target sgRNA. For four of the sixteen sequences explored, UBP loss was already minimal without immunity (non-target sgRNA), but was undetectable with expression of the correct sgRNA (FIG. 3B). The remaining sequences showed moderate to no retention without immunity, and significantly higher retention with it, including at positions up to 15 nts from the PAM.

Figure 3C:
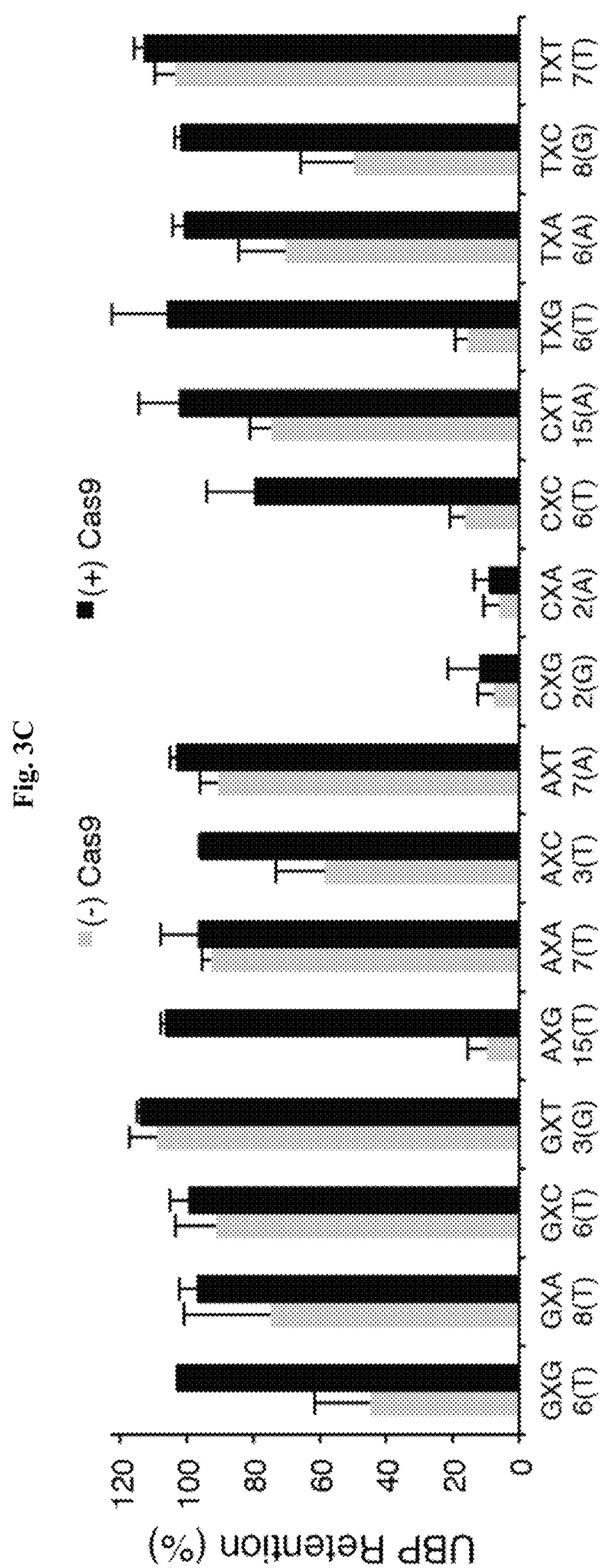

To further simplify and streamline the SSO, strain YZ4 was constructed by integrating an IPTG-inducible Cas9 gene at the arsB locus of the YZ3 chromosome, which allows for the use of a single plasmid that both carries a UBP and expresses the sgRNAs that enforce its retention. Sixteen such "all in one" plasmids (pAIO) were constructed by replacing the Cas9 gene in each of the pCas9 variants with a UBP sequence from the corresponding pUCX2 variant (Extended Data FIG. 2). YZ4 and YZ3 (included as a no Cas9 control due to leaky expression of Cas9 in YZ4) were transformed with a single pAIO plasmid and cultured on solid growth media supplemented with the unnatural triphosphates and with or without IPTG to induce Cas9. Single colonies were used to inoculate liquid media of the same composition, and UBP retention was assessed after cells reached an $OD_{600}$ of ~1-2 (FIG. 3C). Despite variable levels of retention in the absence of Cas9 (YZ3), with induction of Cas9 expression in YZ4, loss was minimal to undetectable in 13 of the 16 the sequences. While retention with the three problematic sequences, d(C-NaM-C) d(C-NaM-A) and d(C-NaM-G), might be optimized, for example, through alterations in Cas9 or sgRNA expression, the undetectable loss of the UBP with the majority of the sequences after a regimen that included growth both on solid and in liquid media, which was not possible with our previous SSO DM1, attests to the vitality of YZ4.

Figure 4:
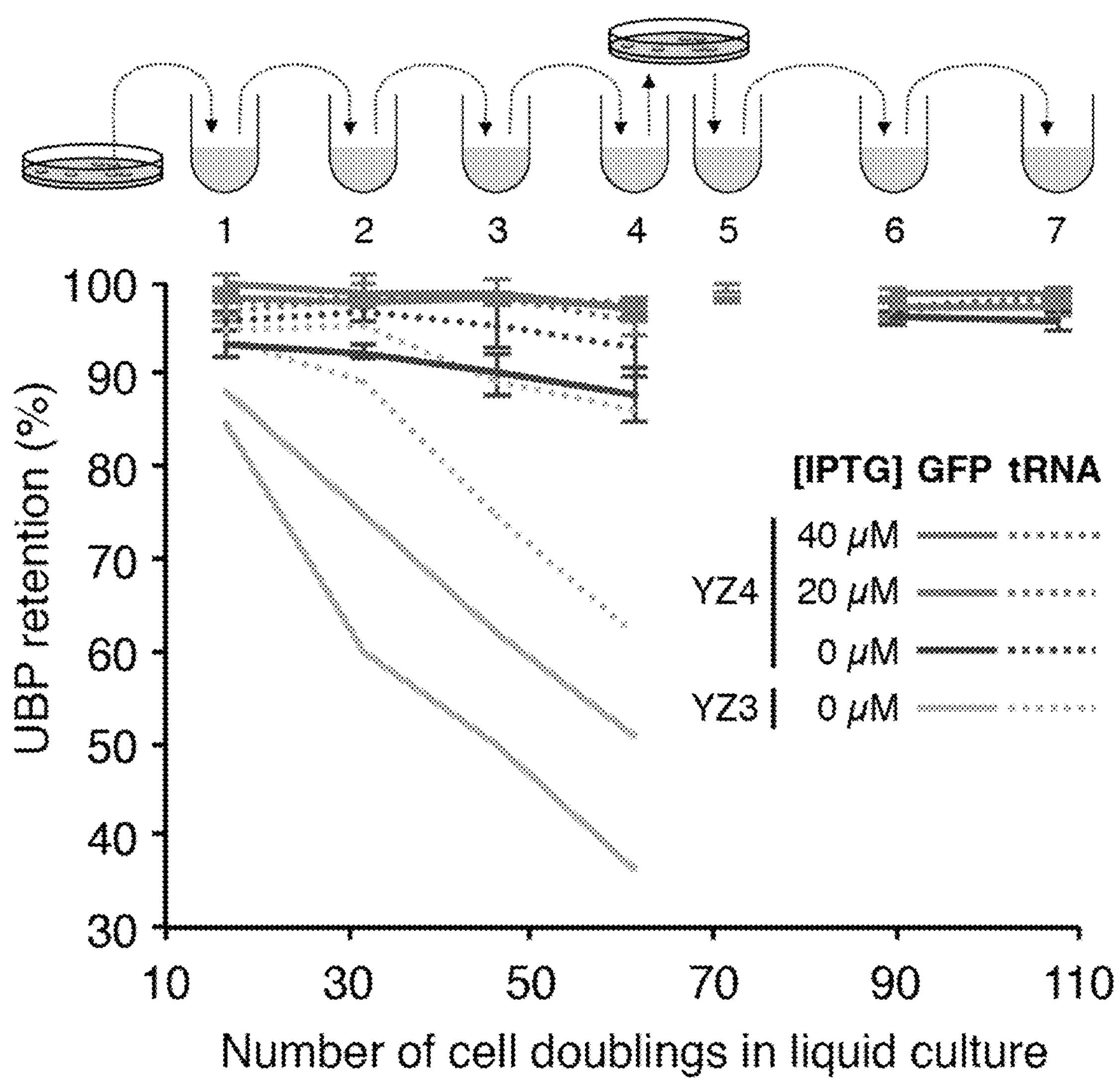
FIG. 4 shows simultaneous retention of two UBPs during extended growth. Strains YZ3 and YZ4 were transformed with pAIO2X and plated on solid media containing dNaMTP and dTPT3TP, with or without IPTG to induce Cas9. Single colonies were inoculated into liquid media of the same composition and cultures were grown to an $OD_{600}$ of ~2 (point 1). Cultures were subsequently diluted 30,000-fold and regrown to an $OD_{600}$ of ~2 (point 2), and this dilution-regrowth process was then repeated two more times (points 3 and 4). As a no immunity control, strain YZ3 was grown in the absence of IPTG and two representative cultures are indicated in gray. Strain YZ4 was grown in the presence of varying amounts of IPTG and averages of cultures are indicated in green (0 μM, n=5), blue (20 μM, n=5), and red (40 μM, n=4). Retentions of the UBP in gfp and serT are indicated with solid or dotted lines, respectively. After the fourth outgrowth, two of the YZ4 cultures grown with 20 μM IPTG were subcultured on solid media of the same composition. Three randomly selected colonies from each plate (n=6 total) were inoculated into liquid media of the same composition, and each of the six cultures was grown to an $OD_{600}$ of ~1 (point 5), diluted 300,000-fold into media containing 0, 20, and 40 μM IPTG, and regrown to an $OD_{600}$ of ~1 (point 6). This dilution-regrowth process was subsequently repeated (point 7). pAIO2X plasmids were isolated at each of the numbered points and analyzed for UBP retention. Cell doublings are estimated from $OD_{600}$ (see Methods) and did not account for growth on solid media (thus making them an underestimate of actual growth). Error bars represent s.d. of the mean.

Finally, a pAIO plasmid, pAIO2X, was constructed containing two UBPs: dNaM paired opposite dTPT3 at position 451 of the sense strand of the gfp gene and dTPT3 paired opposite dNaM at position 35 of the sense strand of the serT tRNA gene, as well as encoding the sgRNAs targeting the most common substitution mutation expected in each sequence (FIG. 6). YZ4 and YZ3 were transformed with pAIO2X and subjected to the challenging growth regime depicted in FIG. 4, which included extensive high-density growth in liquid and on solid growth media. Plasmids were recovered and analyzed for UBP retention (FIG. 7B) when the $OD_{600}$ reached 1-2 during each liquid outgrowth. In YZ3, which does not express Cas9, or in the absence of Cas9 induction (no IPTG) in YZ4, UBP retention steadily declined with extended growth (FIG. 4). With induction of immunity (20 or 40 μM IPTG) a marginal reduction in growth rate (less than 14% increase in doubling time: FIG. 12) was observed, and about 100% UBP retention (no detectable loss) in both genes.

Table 1 illustrates sequences described herein.

| | Sequence | SEQ ID NO: |
|---|---|---|
| PtNTT2<br>(full length) | MRPYPTIALI SVFLSAATRI SATSSHQASA LPVKKGTHVP<br>DSPKLSKLYI MAKTKSVSSSFDPPRGGSTV APTTPLATGG<br>ALRKVRQAVF PIYGNQEVTK FLLIGSIKFF IILALTLTRD<br>TKDTLIVTQC GAEAIAFLKI YGVLPAATAF IALYSKMSNA<br>MGKKMLFYST CIPFFTFFGLFDVFIYPNAE RLHPSLEAVQ<br>AILPGGAASG GMAVLAKIAT HWTSALFYVM AEIYSSVSVG<br>LLFWQFANDV VNVDQAKRFY PLFAQMSGLAPVLAGQYVVR<br>FASKAVNFEA SMHRLTAAVTFAGIMICIFY QLSSSYVERT<br>ESAKPAADNE QSIKPKKKKP KMSMVESGKF LASSQYLRLI<br>AMLVLGYGLS INFTEIMWKS LVKKQYPDPL DYQRFMGNFS<br>SAVGLSTCIV IFFGVHVIRLLGWKVGALAT PGIMAILALP<br>FFACILLGLD SPARLEIAVI FGTIQSLLSK TSKYALFDPT<br>TQMAYIPLDD ESKVKGKAAI DVLGSRIGKS GGSLIQQGLV<br>FVFGNIINAA PVVGVVYYSVLVAWMSAAGR LSGLFQAQTE<br>MDKADKMEAK TNKEK | 1 |
| PtNTT2 (66-575)*<br>DNA (codon<br>optimized)<br>(*66-575 denotes<br>that DNA encoding<br>the first 65 amino<br>acid residues have<br>been deleted<br>relative to the full<br>length PtNTT2) | ATGGGTGGTAGCACCGTTGCACCGACCACACCGCTGGCAA<br>CCGGTGGTGCACTGCGTAAAGTTCGTCAGGCAGTTTTTCC<br>GATTTATGGCAATCAAGAAGTGACCAAATTTCTGCTGATTG<br>GCAGCATCAAATTCTTTATTATCCTGGCACTGACCCTGA<br>CCCGTGATACCAAAGATACCCTGATTGTTACCCAGTGTGGT<br>GCAGAAGCAATTGCATTTCTGAAAATCTATGGTGTTCTG<br>CCTGCAGCAACCGCATTTATTGCACTGTATAGCAAAATGAG<br>CAACGCAATGGGCAAAAAAATGCTGTTTTATAGCACCTG<br>TATCCCGTTCTTTACCTTTTTTGGTCTGTTCGATGTGTTCATT<br>TATCCGAATGCCGAACGTCTGCATCCGAGCCTGGAAG<br>CAGTTCAGGCAATTCTGCCTGGTGGTGCCGCAAGCGGTGGT<br>ATGGCAGTTCTGGCAAAAATTGCAACCCATTGGACCAGC<br>GCACTGTTTTATGTTATGGCAGAAATCTATAGCAGCGTTAG<br>CGTTGGTCTGCTGTTTTGGCAGTTTGCAAATGATGTTGT<br>TAATGTGGATCAGGCCAAACGTTTTTATCCGCTGTTTGCAC<br>AGATGAGCGGTCTGGCACCGGTTCTGGCAGGTCAGTATG<br>TTGTTCGTTTTGCAAGCAAAGCCGTTAATTTTGAAGCAAGC<br>ATGCATCGTCTGACCGCAGCAGTTACCTTTGCAGGTATT<br>ATGATCTGCATCTTTTATCAGCTGAGCAGCTCATATGTTGA<br>ACGTACCGAAAGCGCAAAACCGGCAGCAGATAATGAACA<br>GAGCATTAAACCGAAGAAAAAAAAACCGAAAATGTCGATG<br>GTGGAAAGCGGTAAATTTCTGGCAAGCAGCCAGTATCTGC<br>GTCTGATTGCAATGCTGGTTCTGGGTTATGGTCTGAGCATT<br>AACTTTACCGAAATCATGTGGAAAAGCCTGGTGAAAAAA<br>CAGTATCCGGATCCGCTGGATTATCAGCGTTTTATGGGTAA<br>TTTTAGCAGCGCAGTTGGTCTGAGTACCTGCATTGTTAT<br>CTTTTTTGGCGTGCATGTTATTCGTCTGCTGGGTTGGAAAGT<br>TGGTGCCCTGGCAACACCGGGTATTATGGCCATTCTGG<br>CACTGCCGTTTTTTGCATGTATTCTGCTGGGCCTGGATAGTC<br>CGGCACGTCTGGAAATTGCAGTTATTTTTGGCACCATT<br>CAGAGCCTGCTGAGCAAAACCAGCAAATATGCACTGTTTG<br>ATCCGACCACCCAGATGGCATATATCCCGCTGGATGATGA<br>AAGCAAAGTTAAAGGCAAAGCAGCCATTGATGTTCTGGGT<br>AGCCGTATTGGTAAATCAGGTGGTAGCCTGATTCAGCAGG<br>GTCTGGTTTTTGTTTTTGGCAATATTATCAATGCCGCACCGG<br>TTGTTGGTGTTGTGTATTATAGCGTTCTGGTTGCATGG<br>ATGAGTGCAGCAGGTCGTCTGAGTGGTCTGTTTCAGGCACA<br>GACCGAAATGGATAAAGCAGATAAAATGGAAGCCAAAAC<br>CAACAAAGAAAAATGA | 2 |
| PtNTT2 (66-575)<br>DNA (non codon<br>optimized) | ATGGGAGGCAGTACTGTTGCACCAACTACACCGTTGGCAA<br>CCGGCGGTGCGCTCCGCAAAGTGCGACAAGCCGTCTTTCCC<br>ATCTACGGAAACCAAGAAGTCACCAAATTTCTGCTCATCGG<br>ATCCATTAAATTCTTTATAATCTTGGCACTCACGCTCACGC<br>GTGATACCAAGGACACGTTGATTGTCACGCAATGTGGTGCC<br>GAAGCGATTGCCTTTCTCAAAATATACGGGGTGCTACCCGC<br>AGCGACCGCATTTATCGCGCTCTATTCCAAAATGTCCAACG<br>CCATGGGCAAAAAAATGCTATTTTATTCCACTTGCATTCCT<br>TTCTTTACCTTTTTCGGGCTGTTTGATGTTTTCATTTACCCG<br>AACGCGGAGCGACTGCACCCTAGTTTGGAAGCCGTGCAGG<br>CAATTCTCCCGGGCGGTGCCGCATCTGGCGGCATGGCGGTT<br>CTGGCCAAGATTGCGACACACTGGACATCGGCCTTATTTA<br>CGTCATGGCGGAAATATATTCTTCCGTATCGGTGGGGCTAT<br>TGTTTTGGCAGTTTGCGAACGACGTCGTCAACGTGGATCAG<br>GCCAAGCGCTTTTATCCATTATTTGCTCAAATGAGTGGCCT<br>CGCTCCAGTTTTAGCGGGCCAGTATGTGGTACGGTTTGCCA | 3 |

-continued

| | Sequence | SEQ ID NO: |
|---|---|---|
| | GCAAAGCGGTCAACTTTGAGGCATCCATGCATCGACTCACG GCGGCCGTAACATTTGCTGGTATTATGATTTGCATCTTTTAC CAACTCAGTTCGTCATATGTGGAGCGAACGGAATCAGCAA AGCCAGCGGCAGATAACGAGCAGTCTATCAAACCGAAAAA GAAGAAACCCAAAATGTCCATGGTTGAATCGGGGAAATTT CTCGCGTCAAGTCAGTACCTGCGTCTAATTGCCATGCTGGT GCTGGGATACGGCCTCAGTATTAACTTTACCGAAATCATGT GGAAAAGCTTGGTGAAGAAACAATATCCAGACCCGCTAGA TTATCAACGATTTATGGGTAACTTCTCGTCAGCGGTTGGTTT GAGCACATGCATTGTTATTTTCTTCGGTGTGCACGTGATCC GTTTGTTGGGGTGGAAAGTCGGAGCGTTGGCTACACCTGGG ATCATGGCCATTCTAGCGTTACCCTTTTTTGCTTGCATTTTG TTGGGTTTGGATAGTCCAGCACGATTGGAGATCGCCGTAAT CTTTGGAACAATTCAGAGTTTGCTGAGCAAAACCTCCAAGT ATGCCCTTTTCGACCCTACCACACAAATGGCTTATATTCCTC TGGACGACGAATCAAAGGTCAAAGGAAAAGCGGCAATTGA TGTTTTGGGATCGCGGATTGGCAAGAGTGGAGGCTCACTGA TCCAGCAGGGCTTGGTCTTTGTTTTTGGAAATATCATTAAT GCCGCACCTGTAGTAGGGGTTGTCTACTACAGTGTCCTTGT TGCGTGGATGAGCGCAGCTGGCCGACTAAGTGGGCTTTTTC AAGCACAAACAGAAATGGATAAGGCCGACAAAATGGAGG CAAAGACCAACAAAGAAAAGTAG | |
| PtNTT2 (66-575) protein | MGGSTVAPTTPLATGGALRKVRQAVFPIYGNQEVTKFLLIGSI KFFIILALTLTRDTKDTLIVTQCGAEMAFLKIYGVLPAATAFIA LYSKMSNAMGKKMLFYSTCIPFFTFFGLFDVFIYPNAERLHPS LEAVQAILPGGAASGGMAVLAKIATHWTSALFYVMAEIYSSV SVGLLFWQFANDVVNVDQAKRFYPLFAQMSGLAPVLAGQYV VRFASKAVNFEASMHRLTAAVTFAGIMICIFYQLSSSYVERTE SAKPAADNEQSIKPKKKKPKMSMVESGKFLASSQYLRLIAML VLGYGLSINFTEIMWKSLVKKQYPDPLDYQRFMGNFSSAVGL STCIVIFFGVHVIRLLGWKVGALATPGIMAILALPFFACILLGL DSPARLEIAVIFGTIQSLLSKTSKYALFDPTTQMAYIPLDDESK VKGKAAIDVLGSRIGKSGGSLIQQGLVFVFGNIINAAPVVGVV YYSVLVAWMSAAGRLSGLFQAQTEMDKADKMEAKTNKEK | 4 |
| PtNTT2 (1-22,66-575)* DNA (*1-22, 66-575 denotes that DNA encoding amino acid residues 23-65 have been deleted relative to the full-length PtNTT2) | ATGAGACCATTTCCGACGATTGCCTTGATTTCGGTTTTTCTT TCGGCGGCGACTCGCATTTCGGCAGGAGGCAGTACTGTTGC ACCAACTACACCGTTGGCAACCGGCGGTGCGCTCCGCAAA GTGCGACAAGCCGTCTTTCCCATCTACGGAAACCAAGAAGT CACCAAATTTCTGCTCATCGGATCCATTAAATTCTTTATAAT CTTGGCACTCACGCTCACGCGTGATACCAAGGACACGTTGA TTGTCACGCAATGTGGTGCCGAAGCGATTGCCTTTCTCAAA ATATACGGGGTGCTACCCGCAGCGACCGCATTTATCGCGCT CTATTCCAAAATGTCCAACGCCATGGGCAAAAAAATGCTAT TTTATTCCACTTGCATTCCTTTCTTTACCTTTTTCGGGCTGTT TGATGTTTTCATTTACCCGAACGCGGAGCGACTGCACCCTA GTTTGGAAGCCGTGCAGGCAATTCTCCCGGGCGGTGCCGCA TCTGGCGGCATGGCGGTTCTGGCCAAGATTGCGACACACTG GACATCGGCCTTATTTTACGTCATGGCGGAAATATATTCTT CCGTATCGGTGGGGCTATTGTTTTGGCAGTTTGCGAACGAC GTCGTCAACGTGGATCAGGCCAAGCGCTTTTATCCATTATT TGCTCAAATGAGTGGCCTCGCTCCAGTTTTAGCGGGCCAGT ATGTGGTACGGTTTGCCAGCAAAGCGGTCAACTTTGAGGCA TCCATGCATCGACTCACGGCGGCCGTAACATTTGCTGGTAT TATGATTTGCATCTTTTACCAACTCAGTTCGTCATATGTGGA GCGAACGGAATCAGCAAAGCCAGCGGCAGATAACGAGCA GTCTATCAAACCGAAAAAGAAGAAACCCAAAATGTCCATG GTTGAATCGGGGAAATTTCTCGCGTCAAGTCAGTACCTGCG TCTAATTGCCATGCTGGTGCTGGGATACGGCCTCAGTATTA ACTTTACCGAAATCATGTGGAAAAGCTTGGTGAAGAAACA ATATCCAGACCCGCTAGATTATCAACGATTTATGGGTAACT TCTCGTCAGCGGTTGGTTTGAGCACATGCATTGTTATTTTCT TCGGTGTGCACGTGATCCGTTTGTTGGGGTGGAAAGTCGGA GCGTTGGCTACACCTGGGATCATGGCCATTCTAGCGTTACC CTTTTTTGCTTGCATTTTGTTGGGTTTGGATAGTCCAGCACG ATTGGAGATCGCCGTAATCTTTGGAACAATTCAGAGTTTGC TGAGCAAAACCTCCAAGTATGCCCTTTTCGACCCTACCACA CAAATGGCTTATATTCCTCTGGACGACGAATCAAAGGTCAA AGGAAAAGCGGCAATTGATGTTTTGGGATCGCGGATTGGC AAGAGTGGAGGCTCACTGATCCAGCAGGGCTTGGTCTTTGT TTTTGGAAATATCATTAATGCCGCACCTGTAGTAGGGGTTG TCTACTACAGTGTCCTTGTTGCGTGGATGAGCGCAGCTGGC CGACTAAGTGGGCTTTTTCAAGCACAAACAGAAATGGATA AGGCCGACAAAATGGAGGCAAAGACCAACAAAGAAAAGT AG | 5 |

-continued

| | Sequence | SEQ ID NO: |
|---|---|---|
| PtNTT2(1-22, 66-575) protein | MRPFPTIALISVFLSAATRISAGGSTVAPTTPLATGGALRKVRQ AVFPIYGNQEVTKFLLIGSIKFFIILALTLTRDTKDTLIVTQCGA EATAFLKIYGVLPAATAFIALYSKMSNAMGKKMLFYSTCIPFF TFFGLFDVFIYPNAERLHPSLEAVQAILPGGAASGGMAVLAKI ATHWTSALFYVMAEIYSSVSVGLLFWQFANDVVNVDQAKRF YPLFAQMSGLAPVLAGQYVVRFASKAVNFEASMHRLTAAVT FAGIMICIFYQLSSSYVERTESAKPAADNEQSIKPKKKKPKMS MVESGKFLASSQYLRLIAMLVLGYGLSINFTEIMWKSLVKKQ YPDPLDYQRFMGNFSSAVGLSTCIVIFFGVHVIRLLGWKVGAL ATPGIMAILALPFFACILLGLDSPARLEIAVIFGTIQSLLSKTSKY ALFDPTTQMAYIPLDDESKVKGKAAIDVLGSRIGKSGGSLIQQ GLVFVFGNIINAAPVVGVVYYSVLVAWMSAAGRLSGLFQAQ TEMDKADKMEAKTNKEK | 6 |
| PtNTT2 (23-575)* DNA (*23-575 denotes that DNA encoding amino acid residues 1-22 have been deleted relative to the full-length PtNTT2) | ATGACTTCCTCTCATCAAGCAAGTGCACTTCCTCTCAAAAA GGGAACGCATGTCCCGGACTCTCCGAAGTTGTCAAAGCTAT ATATCATGGCCAAAACCAAGAGTGTATCCTCGTCCTTCGAC CCCCCTCGGGGAGGCAGTACTGTTGCACCAACTACACCGTT GGCAACCGGCGGTGCGCTCCGCAAAGTGCGACAAGCCGTC TTTCCCATCTACGGAAACCAAGAAGTCACCAAATTTCTGCT CATCGGATCCATTAAATTCTTTATAATCTTGGCACTCACGCT CACGCGTGATACCAAGGACACGTTGATTGTCACGCAATGTG GTGCCGAAGCGATTGCCTTTCTCAAAATATACGGGGTGCTA CCCGCAGCGACCGCATTTATCGCGCTCTATTCCAAAATGTC CAACGCCATGGGCAAAAAAATGCTATTTTATTCCACTTGCA TTCCTTTCTTTACCTTTTTCGGGCTGTTTGATGTTTTCATTTA CCCGAACGCGGAGCGACTGCACCCTAGTTTGGAAGCCGTG CAGGCAATTCTCCCGGGCGGTGCCGCATCTGGCGGCATGGC GGTTCTGGCCAAGATTGCGACACACTGGACATCGGCCTTAT TTTACGTCATGGCGGAAATATATTCTTCCGTATCGGTGGGG CTATTGTTTTGGCAGTTTGCGAACGACGTCGTCAACGTGGA TCAGGCCAAGCGCTTTTATCCATTATTTGCTCAAATGAGTG GCCTCGCTCCAGTTTTAGCGGGCCAGTATGTGGTACGGTTT GCCAGCAAAGCGGTCAACTTTGAGGCATCCATGCATCGACT CACGGCGGCCGTAACATTTGCTGGTATTATGATTTGCATCT TTTACCAACTCAGTTCGTCATATGTGGAGCGAACGGAATCA GCAAAGCCAGCGGCAGATAACGAGCAGTCTATCAAACCGA AAAAGAAGAAACCCAAAATGTCCATGGTTGAATCGGGGAA ATTTCTCGCGTCAAGTCAGTACCTGCGTCTAATTGCCATGC TGGTGCTGGGATACGGCCTCAGTATTAACTTTACCGAAATC ATGTGGAAAAGCTTGGTGAAGAAACAATATCCAGACCCGC TAGATTATCAACGATTTATGGGTAACTTCTCGTCAGCGGTT GGTTTGAGCACATGCATTGTTATTTTCTTCGGTGTGCACGTG ATCCGTTTGTTGGGGTGGAAAGTCGGAGCGTTGGCTACACC TGGGATCATGGCCATTCTAGCGTTACCCTTTTTTGCTTGCAT TTTGTTGGGTTTGGATAGTCCAGCACGATTGGAGATCGCCG TAATCTTTGGAACAATTCAGAGTTTGCTGAGCAAAACCTCC AAGTATGCCCTTTTCGACCCTACCACACAAATGGCTTATAT TCCTCTGGACGACGAATCAAAGGTCAAAGGAAAAGCGGCA ATTGATGTTTTGGGATCGCGGATTGGCAAGAGTGGAGGCTC ACTGATCCAGCAGGGCTTGGTCTTTGTTTTTGGAAATATCA TTAATGCCGCACCTGTAGTAGGGGTTGTCTACTACAGTGTC CTTGTTGCGTGGATGAGCGCAGCTGGCCGACTAAGTGGGCT TTTTCAAGCACAAACAGAAATGGATAAGGCCGACAAAATG GAGGCAAAGACCAACAAAGAAAAGTAG | 7 |
| PtNTT2 (23-575) protein | MTSSHQASALPLKKGTHVPDSPKLSKLYIMAKTKSVSSSFDPP RGGSTVAPTTPLATGGALRKVRQAVFPIYGNQEVTKFLLIGSI KFFIILALTLTRDTKDTLIVTQCGAEMAFLKIYGVLPAATAFIA LYSKMSNAMGKKMLFYSTCIPFFTFFGLFDVFIYPNAERLHPS LEAVQAILPGGAASGGMAVLAKIATHWTSALFYVMAEIYSSV SVGLLFWQFANDVVNVDQAKRFYPLFAQMSGLAPVLAGQYV VRFASKAVNFEASMHRLTAAVTFAGIMICIFYQLSSSYVERTE SAKPAADNEQSIKPKKKKPKMSMVESGKFLASSQYLRLIAML VLGYGLSINFTEIMWKSLVKKQYPDPLDYQRFMGNFSSAVGL STCIVIFFGVHVIRLLGWKVGALATPGIMAILALPFFACILLGL DSPARLEIAVIFGTIQSLLSKTSKYALFDPTTQMAYIPLDDESK VKGKAAIDVLGSRIGKSGGSLIQQGLVFVFGNIINAAPVVGVV YYSVLVAWMSAAGRLSGLFQAQTEMDKADKMEAKTNKEK | 8 |

-continued

| | Sequence | SEQ ID NO: |
|---|---|---|
| pBRX2*<br>(*N denotes the position of the UBP) | AACGCCAGCAACGCGGCCTTTTTACGGTTCCTGGCCTTTTG<br>CTGGCCTTTTGCTCACATGTTCTTTCCTGCGTTATCCCC<br>TGATTCTGTGGATAACCGTATTACCGCCTTTGAGTGAGCTG<br>ATACCGCTCGCCGCAGCCGAACGACCGAGCGCAGCGAGT<br>CAGTGAGCGAGGAAGCGGAAGAGCGCCTGATGCGGTATTT<br>TCTCCTTACGCATCTGTGCGGTATTTCACACCGCATATGG<br>TGCACTCTCAGTACAATCTGCTCTGATGCCGCATAGTTAAG<br>CCAGTATACACTCCGCTATCGCTACGTGACTGGGTCATG<br>GCTGCGCCCCGACACCCGCCAACACCCGCTGACGCGCCCTG<br>ACGGGCTTGTCTGCTCCCGGCATCCGCTTACAGACAAGC<br>TGTGACCGTCTCCGGGAGCTGCATGTGTCAGAGGTTTTCAC<br>CGTCATCACCGAAACGCGCGAGGCAGCTGCGGTAAAGCT<br>CATCAGCGTGGTCGTGAAGCGATTCACAGATGTCTGCCTGT<br>TCATCCGCGTCCAGCTCGTTGAGTTTCTCCAGAAGCGTT<br>AATGTCTGGCTTCTGATAAAGCGGGCCATGTTAAGGGCGGT<br>TTTTTCCTGTTTGGTCACTGATGCCTCCGTGTAAGGGGG<br>ATTTCTGTTCATGGGGGTAATGATACCGATGAAACGAGAG<br>AGGATGCTCACGATACGGGTTACTGATGATGAACATGCCC<br>GGTTACTGGAACGTTGTGAGGGTAAACAACTGGCGGTATG<br>GATGCGGCGGGACCAGAGAAAAATCACTCAGGGTCAATGC<br>CAGCGCTTCGTTAATACAGATGTAGGTGTTCCACAGGGTAG<br>CCAGCAGCATCCTGCGATGCAGATCCGGAACATAATGGT<br>GCAGGGCGCTGACTTCCGCGTTTCCAGACTTTACGAAACAC<br>GGAAACCGAAGACCATTCATGTTGTTGCTCAGGTCGCAG<br>ACGTTTTGCAGCAGCAGTCGCTTCACGTTCGCTCGCGTATC<br>GGTGATTCATTCTGCTAACCAGTAAGGCAACCCCGCCAG<br>CCTAGCCGGGTCCTCAACGACAGGAGCACGATCATGCGCA<br>CCCGTGGCCAGGACCCAACGCTGCCCGAAATTCTTGAAGA<br>CGAAAGGGCCTCGTGATACGCCTATTTTTATAGGTTAATGT<br>CATGATAATAATGGTTTCTTAGACGTCAGGTGGCACTTT<br>TCGGGGAAATGTGCGCGGAACCCCTATTTGTTTATTTTTCT<br>AAATACATTCAAATATGTATCCGCTCATGAGACAATAAC<br>CCTGATAAATGCTTCAATAATATTGAAAAAGGAAGAGTAT<br>GAGTATTCAACATTTCCGTGTCGCCCTTATTCCCTTTTTT<br>GCGGCATTTTGCCTTCCTGTTTTTGCTCACCCAGAAACGCTG<br>GTGAAAGTAAAAGATGCTGAAGATCAGTTGGGTGCACG<br>AGTGGGTTACATCGAACTGGATCTCAACAGCGGTAAGATC<br>CTTGAGAGTTTTCGCCCCGAAGAACGTTTTCCAATGATGA<br>GCACTTTTAAAGTTCTGCTATGTGGCGCGGTATTATCCCGT<br>GTTGACGCCGGGCAAGAGCAACTCGGTCGCCGCATACAC<br>TATTCTCAGAATGACTTGGTTGAGTACTCACCAGTCACAGA<br>AAAGCATCTTACGGATGGCATGACAGTAAGAGAATTATG<br>CAGTGCTGCCATAACCATGAGTGATAACACTGCGGCCAACT<br>TACTTCTGACAACGATCGGAGGACCGAAGGAGCTAACCG<br>CTTTTTTGCACAACATGGGGGATCATGTAACTCGCCTTGAT<br>CGTTGGGAACCGGAGCTGAATGAAGCCATACCAAACGAC<br>GAGCGTGACACCACGATGCCTGCAGCAATGGCAACAACGT<br>TGCGCAAACTATTAACTGGCGAACTACTTACTCTAGCTTC<br>CCGGCAACAATTAATAGACTGGATGGAGGCGGATAAAGTT<br>GCAGGACCACTTCTGCGCTCGGCCCTTCCGGCTGGCTGGT<br>TTATTGCTGATAAATCTGGAGCCGGTGAGCGTGGCTCTCGC<br>GGTATCATTGCAGCACTGGGGCCAGATGGTAAGCCCTCC<br>CGTATCGTAGTTATCTACACGACGGGGAGTCAGGCAACTAT<br>GGATGAACGAAATAGACAGATCGCTGAGATAGGTGCCTC<br>ACTGATTAAGCATTGGTAACTGTCAGACCAAGTTTACTCAT<br>ATATACTTTAGATTGATTTAAAACTTCATTTTTAATTTA<br>AAAGGATCTAGGTGAAGATCCTTTTTGATAATCTCATGACC<br>AAAATCCCTTAACGTGAGTTTTCGTTGGCTTTACACTTT<br>ATGCTTCCGGCTCGTATGTTGTGTGGAANTGTGAGCGGATA<br>ACAATTTCACACAGGAAACAGCCACTGAGCGTCAGACCC<br>CGTAGAAAAGATCAAAGGATCTTCTTGAGATCCTTTTTTTC<br>TGCGCGTAATCTGCTGCTTGCAAACAAAAAAACCACCGC<br>TACCAGCGGTGGTTTGTTTGCCGGATCAAGAGCTACCAACT<br>CTTTTTCCGAAGGTAACTGGCTTCAGCAGAGCGCAGATA<br>CCAAATACTGTCCTTCTAGTGTAGCCGTAGTTAGGCCACCA<br>CTTCAAGAACTCTGTAGCACCGCCTACATACCTCGCTCT<br>GCTAATCCTGTTACCAGTGGCTGCTGCCAGTGGCGATAAGT<br>CGTGTCTTACCGGGTTGGACTCAAGACGATAGTTACCGG<br>ATAAGGCGCAGCGGTCGGGCTGAACGGGGGGTTCGTGCAC<br>ACAGCCCAGCTTGGAGCGAACGACCTACACCGAACTGAGA<br>TACCTACAGCGTGAGCTATGAGAAAGCGCCACGCTTCCCG | 9 |

-continued

| Sequence | SEQ ID NO: |
|---|---|
| AAGGGAGAAAGGCGGACAGGTATCCGGTAAGCGGCAGGG TCGGAACAGGAGAGCGCACGAGGGAGCTTCCAGGGGGAA ACGCCTGGTATCTTTATAGTCCTGTCGGGTTTCGCCACCTCT GACTTGAGCGTCGATTTTTGTGATGCTCGTCAGGGGGGCGG AGCCTATGGAAA | |

TABLE 2

| Primer | Application | Sequence | SEQ ID NO: |
|---|---|---|---|
| | Transporter plasmid cloning and chromosomal integration | | |
| YZ552 | Cloning PtNTT2(66-575) | GGGAGGCAGTACTGTTGCAC | 10 |
| pCDF-1b-fwd | Cloning PtNTT2(66-575) | GGTATATCTCCTTATTAAAGTTAAACAAAATTATTTCT ACAGGGG | 11 |
| T7 seq | sequencing pCDF plasmids | TAATACGACTCACTATAGGG | 12 |
| T7 term seq | sequencing pCDF plasmids | GCTAGTTATTGCTCAGCGG | 13 |
| YZ580 | transporter cloning | TTACATTAATTGCGTTGCGCTC | 14 |
| DM002 | transporter cloning | TTTTGGCGGATGGCATTTGAGAAGCACACGG | 15 |
| YZ576 | transporter cloning | ATTCTCACCAATAAAAAACGCCCGG | 16 |
| YZ581 | transporter cloning | CCTGTAGAAATAATTTTGTTTAACTTTAATAAGGAG | 17 |
| DM052 | transporter sequencing | CCCCGCGCGTTGGCCGATTC | 18 |
| DM053 | transporter sequencing | GAAGGGCAATCAGCTGTTG | 19 |
| YZ50 | transporter sequencing | CAGGGCAGGGTCGTTAAATAG | 20 |
| YZ584 | lacI promoter | GACACCATCGAATGGCGCAAAACCTTTCGCGGTATGG CATGATAGCGCCCGG | 21 |
| YZ585 | lacI promoter | CCGGGCGCTATCATGCCATACCGCGAAAGGTTTTGCG CCATTCGATGGTGTC | 22 |
| YZ582 | bla promoter | ATTTTTCTAAATACATTCAAATATGTATCCGCTCATGA GACAATAACCCTG | 23 |
| YZ583 | bla promoter | CAGGGTTATTGTCTCATGAGCGGATACATATTTGAAT GTATTTAGAAAAAT | 24 |
| YZ599 | lac promoter | TTAGGCACCCCAGGCTTTACACTTTATGCTTCCGGCTG GTATGTTGTGTGGA | 25 |
| YZ600 | lac promoter | TCCACACAACATACCAGCCGGAAGCATAAAGTGTAAA GCCTGGGGTGCCTAA | 26 |
| YZ595 | lacUV5 promoter | CTAGGCACCCCAGGCTTTACACTTTATGCTTCCGGCTG GTATAATGTGTGGA | 27 |
| YZ596 | lacUV5 promoter | TCCACACATTATACCAGCCGGAAGCATAAAGTGTAAA GCCTGGGGTGCCTAG | 28 |
| YZ7 | transporter integration cloning | GGGGATAACGCAGGAAAGAACATG | 29 |

TABLE 2-continued

| | | | |
|---|---|---|---|
| YZ12 | transporter integration cloning | GCACTTTTCGGGGAAATGTGCG | 30 |
| YZ612 | transporter integration cloning | AATTGCGGCCTATATGGATGTTGGAACCGTAAGAGAA ATAGACAGGCGGTCCTGTGACGGAAGATCACTTCGCA G | 31 |
| YZ613 | transporter integration cloning | TGCTCACATGTTCTTTCCTGCGTTATCCCCGCGTGGTG AACCAGGC | 32 |
| YZ614 | transporter integration cloning | ACCGCCTGTCTATTTCTCTTACGGTTCC | 33 |
| YZ615 | transporter integration cloning | CGCGCTTAATGCGCCGCTACAGGGCGCGTCGATTGGT GCCAGCGCGCAG | 34 |
| YZ610 | transporter integration cloning | GGTATATCTCCTTATTAAAGTTAAACAAAATTATTTCT ACAGG | 35 |
| YZ616 | lacZYA:: transporter integration | CAGCCACGTTTCTGCGAAAAC | 36 |
| YZ617 | lacZYA:: transporter integration | TACAGCGGTTCCTTACTGGC | 37 |
| YZ618 | transporter integration colony PCR | GGGTGGTGAATGTGAAACCAGTAACG | 38 |
| YZ619 | transporter integration colony PCR | CTGGGTGTTTACTTCGGTCTG | 39 |
| YZ69 | transporter integration colony PCR | GGCCGTAATATCCAGCTGAAC | 40 |
| YZ587 | transporter integration colony PCR | ACTAGGGTGCAGTCGCTCCG | 41 |
| pCDF-1b-rev | integration cloning | TTAACCTAGGCTGCTGCCACCG | 42 |
| YZ703 | tac promoter | GCGCAACGCAATTAATGTAATTCTGAAATGAGCTGTT GACAATTAATCATCGGCTCG | 43 |
| YZ704 | tac promoter | AACAAAATTATTTCTACAGGTCCACACATTATACGAG CCGATGATTAATTGTCAAC | 44 |
| YZ707 | N25 promoter | GCGCAACGCAATTAATGTAATCATAAAAAATTTATTT GCTTTCAGGAAAATTTTTCTG | 45 |
| YZ708 | N25 promoter | AACAAAATTATTTCTACAGGTGAATCTATTATACAGA AAAATTTTCCTGAAAGCAAATA | 46 |
| YZ709 | λ promoter | GCGCAACGCAATTAATGTAATTATCTCTGGCGGTGTT GACATAAATACCACTGGCG | 47 |
| YZ710 | λ promoter | AACAAAATTATTTCTACAGGTGTGCTCAGTATCACCG CCAGTGGTATTTATGTCAAC | 48 |
| YZ711 | H207 promtoer | GCGCAACGCAATTAATGTAATTTTAAAAAATTCATTT GCTAAACGCTTCAAATTCTCG | 49 |
| YZ712 | H207 promtoer | AACAAAATTATTTCTACAGGTGAAGTATATTATACGA GAATTTGAAGCGTTTAGC | 50 |
| pUCX and pBRX Golden Gate destination plasmid cloning | | | |
| pUC19-lin-fwd | TK1 site removal/pBRX1 linearization | TGGGGTGCCTAATGAGTGAGC | 51 |

TABLE 2-continued

| | | | |
|---|---|---|---|
| pUC19-lin-rev | TK1 site removal/pBRX1 linearization | CTATGACCATGATTACGCCAAGCTTG | 52 |
| YZ51 | bla BsaI site mutation | TCTCGCGGTATCATTGCAGCACTG | 53 |
| YZ52 | bla BsaI site mutation | GCCACGCTCACCGGCTCC | 54 |
| YZ95 | pUCX2/pBRX2 linearization | AACGAAAACTCACGTTAAGGG | 55 |
| YZ96 | pUCX2/pBRX2 linearization | CCACTGAGCGTCAGACC | 56 |
| YZ93 | BsaI zeoR stuffer cassette | GAGACCCGTCGTTGACAATTAATCATCGGC | 57 |
| YZ94 | BsaI zeoR stuffer cassette | GAGACCATTCTCACCAATAAAAAACGCCCGG | 58 |
| pCas9 and pAIO cloning, Cas9 chromosomal integration | | | |
| JL126 | pCas9 cloning | CGGGGTACCATGGACAAGAAGTACTCCATT | 59 |
| JL128 | pCas9 cloning | CTAGTCTAGATTACACCTTCCTCTTCTTCTTGGG | 60 |
| BL557 | pCas9 BsmBI site removal | CTCCGGGGAAACCGCCGAAGCCACGCGGCTCAA | 61 |
| BL558 | pCas9 BsmBI site removal | CTTCGGCGGTTTCCCCGGAGTCGAACAGGAGGGCGCC AATGAGG | 62 |
| BL559 | pCas9-Multi cloning | AGGAAGAAGACGTCTCACGCATCTTACTGCGCAGATA CGC | 63 |
| BL560 | pCas9-Multi cloning | AAGATGCGTGAGACGTCTTCTTCCTCGTCTCGGTCGAC AGTTCATAGGTGATTGCTCAGG | 64 |
| YZ720 | arsB::Cas9 integration | GTCCCAAATCGCAGCCAATCACATTG | 65 |
| YZ721 | arsB::Cas9 integration | GTCCTGACCATCGTATTGGTTATCTGGC | 66 |
| TG1 | Cas9 sequencing | ATTTAGAGGGCAGTGCCAGCTCGTTA | 67 |
| TG2 | Cas9 sequencing | CTGCATTCAGGTAGGCATCATGCGCA | 68 |
| TG3 | Cas9 sequencing | CTGGGCTACCTGCAAGATTAGCGATG | 69 |
| TG4 | Cas9 sequencing | TGAAGGACTGGGCAGAGGCCCCCTT | 70 |
| TG5 | Cas9 sequencing | CGTAGGTGTCTTTGCTCAGTTGAAGC | 71 |
| TG6 | Cas9 sequencing | TAGCCATCTCATTACTAAAGATCTCCT | 72 |
| BL731 | pAIO-Multi cloning (ΔCas9, introduce BsaI) | CGATATCGTTGGTCTCAACGACACAATTGTAAAGGTT AGATCT | 73 |
| BL732 | pAIO-Multi cloning (ΔCas9, introduce BsaI) | CAACGATATCGGTCTCACACTGACTGGGCCTTTCGTTT TATCT | 74 |
| BL450 | pAIO guide sequencing | GCAATCACCTATGAACTGTCGAC | 75 |
| Cas9 guide cloning upper case denotes the BsmBI recognition sequence (6 nt), the BsmBI restriction site overhang (4 nt), or variable target (spacer) sequence (18-20 nt) | | | |
| BL691 | 1st sgRNA GG A GXG-T | aggaggaaggaCGTCTCaTGCGccccgcattCACACAATGTAGTG ATCAgttttagagctagaaatagc | 76 |
| BL627 | 1st sgRNA GG A GXA-T | aggaggaaggaCGTCTCaTGCGccccgcattCCAGGATGGGTAC CACCCgttttagagctagaaatagc | 77 |

TABLE 2-continued

| | | | |
|---|---|---|---|
| BL707 | 1st sgRNA GG A GXC-T | aggaggaaggaCGTCTCaTGCGccccgcattCACACAATGTAGTC ATCAgttttagagctagaaatagc | 78 |
| BL642 | 1st sgRNA GG A GXT-G | aggaggaaggaCGTCTCaTGCGccccgcattCCAGGATGGGCAC CAGCCgttttagagctagaaatagc | 79 |
| BL659 | 1st sgRNA GG A AXG-T/CXT-T | aggaggaaggaCGTCTCaTGCGccccgcattCCATGATGGGCACC ACCCgttttagagctagaaatagc | 80 |
| BL623 | 1st sgRNA GG A AXA-T | aggaggaaggaCGTCTCaTGCGccccgcattCACACAATGTATAG ATCAgttttagagctagaaatagc | 81 |
| BL628 | 1st sgRNA GG A AXC-T | aggaggaaggaCGTCTCaTGCGccccgcattCCAGGATGGGCAC CATCCgttttagagctagaaatagc | 82 |
| BL567 | 1st sgRNA GG A AXT-A | aggaggaaggaCGTCTCaTGCGccccgcattGTTGTGTGGAAATG TGAGgttttagagctagaaatagc | 83 |
| BL593 | 1st sgRNA GG A CXG-G | aggaggaaggaCGTCTCaTGCGccccgcattTGTCACTACTCTGA CCAGgttttagagctagaaatagc | 84 |
| BL639 | 1st sgRNA GG A CXA-A | aggaggaaggaCGTCTCaTGCGccccgcattTGTCACTACTCTGA CCAAgttttagagctagaaatagc | 85 |
| BL693 | 1st sgRNA GG A CXC-T | aggaggaaggaCGTCTCaTGCGccccgcattCACACAATGTACTC ATCAgttttagagctagaaatagc | 86 |
| BL660 | 1st sgRNA GG A CXT-A | aggaggaaggaCGTCTCaTGCGccccgcattCCAAGATGGGCAC CACCCgttttagagctagaaatagc | 87 |
| BL695 | 1st sgRNA GG A TXG-T | aggaggaaggaCGTCTCaTGCGccccgcattCACACAATGTATTG ATCAgttttagagctagaaatagc | 88 |
| BL629 | 1st sgRNA GG A TXA-A | aggaggaaggaCGTCTCaTGCGccccgcattCACACAATGTATAA ATCAgttttagagctagaaatagc | 89 |
| BL657 | 1st sgRNA GG A TXC-G | aggaggaaggaCGTCTCaTGCGccccgcattCCAGGATGGGGAC CACCCgttttagagctagaaatagc | 90 |
| BL620 | 1st sgRNA GG A TXT-T | aggaggaaggaCGTCTCaTGCGccccgcattTTCACAATACTTTC TTTAgthtagagctagaaatagc | 91 |
| BL701 | 2nd sgRNA, Fwd GΔG | gcattTCACACAATGTAGGATCAgttttagagctagaaatagc | 92 |
| BL702 | 2nd sgRNA, Rev GΔG | TGATCCTACATTGTGTGAaatgcggggcgcatcttact | 93 |
| BL617 | 2nd sgRNA, Fwd GΔA | gcattACCAGGATGGGACCACCCgttttagagctagaaatagc | 94 |
| BL618 | 2nd sgRNA, Rev GΔA | GGGTGGTCCCATCCTGGTaatgcggggcgcatcttact | 95 |
| BL705 | 2nd sgRNA, Fwd GΔC | gcattTCACACAATGTAGCATCAgttttagagctagaaatagc | 96 |
| BL706 | 2nd sgRNA, Rev GΔC | TGATGCTACATTGTGTGAaatgcggggcgcatcttact | 97 |
| BL614 | 2nd sgRNA, Fwd GΔT | gcattACCAGGATGGGCACCACCgttttagagctagaaatagc | 98 |
| BL615 | 2nd sgRNA, Rev GΔT | GGTGGTGCCCATCCTGGTaatgcggggcgcatcttact | 99 |
| BL682 | 2nd sgRNA, Fwd AΔG | gcattACCAGATGGGCACCACCCgttttagagctagaaatagc | 100 |
| BL683 | 2nd sgRNA, Rev AΔG | GGGTGGTGCCCATCTGGTaatgcggggcgcatcttact | 101 |
| BL575 | 2nd sgRNA, Fwd AΔA | gcattTCACACAATGTAAGATCAgttttagagctagaaatagc | 102 |
| BL576 | 2nd sgRNA, Rev AΔA | TGATCTTACATTGTGTGAaatgcggggcgcatcttact | 103 |

TABLE 2-continued

| | | | |
|---|---|---|---|
| BL564 | 2nd sgRNA, Fwd AΔT | gcattTGTTGTGTGGAATGTGAGgttttagagctagaaatagc | 104 |
| BL565 | 2nd sgRNA, Rev AΔT | CTCACATTCCACACAACAaatgcggggcgcatcttact | 105 |
| BL675 | 2nd sgRNA, Fwd CΔG | gcattTTGTCACTACTCTGACCGgttttagagctagaaatagc | 106 |
| BL676 | 2nd sgRNA, Rev CΔG | CGGTCAGAGTAGTGACAAaatgcggggcgcatcttact | 107 |
| BL673 | 2nd sgRNA, Fwd CΔA | gcattTTGTCACTACTCTGACCAgttttagagctagaaatagc | 108 |
| BL674 | 2nd sgRNA, Rev CΔA | TGGTCAGAGTAGTGACAAaatgcggggcgcatcttact | 109 |
| BL703 | 2nd sgRNA, Fwd CΔC | gcattTCACACAATGTACCATCAgttttagagctagaaatagc | 110 |
| BL704 | 2nd sgRNA, Rev CΔC | TGATGGTACATTGTGTGAaatgcggggcgcatcttact | 111 |
| BL697 | 2nd sgRNA, Fwd TΔG | gcattTCACACAATGTATGATCAgttttagagctagaaatagc | 112 |
| BL698 | 2nd sgRNA, Rev TΔG | TGATCATACATTGTGTGAaatgcggggcgcatcttact | 113 |
| BL679 | 2nd sgRNA, Fwd TΔA | gcattTCACACAATGTATAATCAgttttagagctagaaatagc | 114 |
| BL680 | 2nd sgRNA, Rev TΔA | TGATTATACATTGTGTGAaatgcggggcgcatcttact | 115 |
| BL620 | 2nd sgRNA, Fwd TΔT | gcattATTCACAATACTTCTTTAgttttagagctagaaatagc | 116 |
| BL621 | 2nd sgRNA, Rev TΔT | TAAAGAAGTATTGTGAATaatgcggggcgcatcttact | 117 |
| BL562 | 1st sgRNA construction | agaaggaagaCGTCTCaCTGTcgaccaaaaaagcctgctcgttgagc | 118 |
| BL563 | 2nd sgRNA construction | aagaaggaCGTCTCaACAGtagtggcagcggctaactaag | 119 |
| BL566 | Terminating sgRNA construction | aggagaggaCGTCTCtCGACcaaaaaagcctgctcgttgagcag | 120 |
| BL514 | natural hEGFP guide cloning | agtaagatgcgccccgcattGACCAGGATGGGCACCACCCgttttaga gctagaaatag | 121 |
| BL515 | natural hEGFP guide cloning | ctatttctagctctaaaacGGGTGGTGCCCATCCTGGTCaatgcggggc gcatcttact | 122 |
| BL464 | natural hEGFP guide cloning | GTTTTAGAGCTAGAAATAGCAAGTTAAAATAAGGCTA GT | 123 |
| BL465 | natural hEGFP guide cloning | AATGCGGGGCGCATCTTACT | 124 |
| YZ310 | ESer-69 guide fwd | cattGGCACCGGTCTACTAAAC | 125 |
| YZ316 | ESer-69 guide rev | aaacGTTTAGTAGACCGGTGCC | 126 |
| YZ359 | GFP151-69 guide fwd | cgcattCACACAATGTAAGTATCAgtttt | 127 |
| YZ360 | GFP151-69 guide rev | ctctaaaacTGATACTTACATTGTGTGaa | 128 |

TABLE 2-continued

| In vitro cleavage (IVC) DNA templates and sgRNAs | | | |
|---|---|---|---|
| BL487 | IVC DNA Template | GTTTACGTCGCCGTCCAGCTCGACCAGGATGGGCACC AACCCGGTGAACAGCTCCTCGCC | 129 |
| BL488 | IVC DNA Template | GTTTACGTCGCCGTCCAGCTCGACCAGGATGGGCACC AGCCCGGTGAACAGCTCCTCGCC | 130 |
| BL489 | IVC DNA Template | GTTTACGTCGCCGTCCAGCTCGACCAGGATGGGCACC ATCCCGGTGAACAGCTCCTCGCC | 131 |
| BL408 | IVC DNA Template | GTTTACGTCGCCGTCCAGCTCGACCAGGATGGGCACC ACCCCGGTGAACAGCTCCTCGCC | 132 |
| BL415 | IVC Template Extension | GCATCGCCCTCGCCCTCGCCGGACACGCTGAACTTGT GGCCGTTTACGTCGCCGTCCAGC | 133 |
| BL416 | IVC Template Extension | TGCAGTTTCATTTGATGCTCGATGAGTTATGGTGAGCA AGGGCGAGGAGCTGTTCACCGG | 134 |
| BL484 | IVC crRNA | TTAATACGACTCACTATAGGGACCAGGATGGGCACCA ACCGTTTTAGAGCTAGAAATAGCAAGTTAAAATAAGG CTAGT | 135 |
| BL485 | IVC crRNA | TTAATACGACTCACTATAGGGACCAGGATGGGCACCA GCCGTTTTAGAGCTAGAAATAGCAAGTTAAAATAAGG CTAGT | 136 |
| BL486 | IVC crRNA | TTAATACGACTCACTATAGGGACCAGGATGGGCACCA TCCGTTTTAGAGCTAGAAATAGCAAGTTAAAATAAGG CTAGT | 137 |
| BL318 | IVC crRNA | TTAATACGACTCACTATAGGGACCAGGATGGGCACCA CCCGTTTTAGAGCTATGCTGTTTTG | 138 |
| BL439 | IVC Conversion crRNA to sgRNA | AAAAGCACCGACTCGGTGCCACTTTTTCAAGTTGATA ACGGACTAGCCTTATTTTAACTTGCTATTTCTAGCTCT AAAACGG | 139 |
| BL472 | PCR sgRNA | AAGAGGAAGAGGTTAATACGACTCACTATAGGGAC | 140 |
| BL440 | PCR sgRNA | AAAAGCACCGACTCGGTGCC | 141 |
| BL473 | PCR sgRNA | ACTAGCCTTATTTTAACTTGCTATTTCTAGCTCTAAAA CGG | 142 |

| Primers for UBP-containing Golden Gate inserts<br>italics denote the BsaI recognition sequence, underline denotes the BsaI restriction site overhang sequence<br>insert primers for pUCX2 are also compatible with pBRX2 and pAIO GG plasmids<br># denotes primers that were also used for biotin shift (the corresponding dedicated biotin shift primers are identical in annealing sequence)<br>YZ401 and YZ403 are highly sensitive to annealing temperature. The optimal annealing temperature is 54° C. | | | |
|---|---|---|---|
| BL528 | hEGFP insert for pUCX2 GG fwd | AAGAAGGAGAA*GGTCTC*TAGTGGAGCAAGGGCGAGG AGCTGTTCACCG | 143 |
| BL529 | hEGFP insert for pUCX2 GG rev | AAGAGAAGAGA*GGTCTC*ATCGTGTTTACGTCGCCGTC CAGCTC | 144 |
| YZ148 | GFP66 insert for pUCX2 GG fwd | ATG*GGTCTC*CAGTGGGGCCAACACTTGTCACTAC | 145 |
| YZ149 | GFP66 insert for pUCX2 GG rev | ATG*GGTCTC*TTCGTTTCCGGATAACGGGAAAAGC | 146 |
| YZ150 | GFP151 insert for pUCX2 GG fwd | ATG*GGTCTC*CAGTGGCTCGAGTACAACTTTAACTCACA C | 147 |
| YZ151 | GFP151 insert for pUCX2 GG rev | ATG*GGTCTC*TTCGTTGATTCCATTCTTTGTTTGTCTGC | 148 |
| YZ97 | TK1 insert for pUCX1 GG fwd | ATG*GGTCTC*TCATAGCTGTTTCCTGTGTGAAATTGTTA TCC | 149 |

TABLE 2-continued

| | | | |
|---|---|---|---|
| YZ98 | TK1 insert for pUCX1 GG rev | ATG*GGTCTCA*CCCCAGGCTTTACACTTTATGCTTCCG | 150 |
| YZ99[#] | TK1 insert for pUCX2 GG fwd | ATG*GGTCTCC*AGTGGCTGTTTCCTGTGTGAAATTGTTA TCC | 151 |
| YZ100[#] | TK1 insert for pUCX2 GG rev | ATG*GGTCTCT*TCGTTGGCTTTACACTTTATGCTTCCG | 152 |
| YZ118 | D8 insert for pUCX2 GG fwd | ATG*GGTCTCC*AGTGGCACACAGGAAACAGCTATGAC | 153 |
| YZ119 | D8 insert for pUCX2 GG rev | ATG*GGTCTCT*TCGTTGGGTTAAGCTTAACTTTAAGAAG GAG | 154 |
| YZ73[#] | GFP151 insert for pAIO2X GG fwd | ATG*GGTCTCA*CACAAACTCGAGTACAACTTTAACTCA CAC | 155 |
| YZ74[#] | GFP151 insert for pAIO2X GG rev | ATG*GGTCTCG*ATTCCATTCTTTTGTTTGTCTGC | 156 |
| YZ401[#] | ESer insert for pAIO2X GG fwd | ATT*GGTCTCG*GCCGAGCGGTTGAAGGCAC | 157 |
| YZ403[#] | ESer insert for pAIO2X GG rev | ATT*GGTCTCT*CTGGAACCCTTTCGGGTCG | 158 |
| Biotin shift primers annealing temperature (° C.) denoted in parentheses | | | |
| BL745 | hEGFP fwd (48 x 3 cycles, 54 x 20 cycles) | GGCGAGGAGCTGTTCACCG | 159 |
| BL744 | hEGFP rev (48 x 3 cycles, 54 x 20 cycles) | GTTTACGTCGCCGTCCAGCTC | 160 |
| BL750 | GFP66 fwd (50) | GGCCAACACTTGTCACTACT | 161 |
| BL751 | GFP66 rev (50) | TCCGGATAACGGGAAAAGC | 162 |
| YZ351 | GFP151 fwd (50) | CTCGAGTACAACTTTAACTCACAC | 163 |
| YZ352 | GFP151 rev (50) | GATTCCATTCTTTTGTTTGTCTGC | 164 |
| BL748 | TK1 fwd (50) | CTGTTTCCTGTGTGAAATTGTTATCC | 165 |
| BL749 | TK1 rev (50) | GGCTTTACACTTTATGCTTCCG | 166 |
| BL774 | D8 fwd (50) | CCCGGGTTATTACATGCGCTAGCACT | 167 |
| BL775 | D8 rev (50) | GAAATTAATACGACTCACTATAGGGTTAAGCTTAACT TTAAGAAGGAG | 168 |
| YZ17 | pUCX2 fwd (60) | TGCAAGCAGCAGATTACGCGC | 169 |
| YZ18 | pUCX2 rev (60) | GTAACTGTCAGACCAAGTTTACTC | 170 |

UBP template oligonucleotides
*denotes sequences used in Cas9 experiments X denotes dNaM

| Name | Sequence Type | Sequence | |
|---|---|---|---|
| BL410* | hEGFP | GGCGAGGAGCTGTTCACCGGGXTGGTGCCCATCCTGG TCGAGCTGGACGGCGACGTAAAC | 171 |
| BL413* | hEGFP | GTTTACGTCGCCGTCCAGCTCGACCAGGATGGGXACC ACCCCGGTGAACAGCTCCTCGCC | 172 |
| BL411* | hEGFP | GTTTACGTCGCCGTCCAGCTCGACCAXGATGGGCACC ACCCCGGTGAACAGCTCCTCGCC | 173 |
| BL409* | hEGFP | GTTTACGTCGCCGTCCAGCTCGACCAGGATGGGCACC AXCCCGGTGAACAGCTCCTCGCC | 174 |

TABLE 2-continued

| | | | |
|---|---|---|---|
| TK1* | TK1 | CTGTTTCCTGTGTGAAATTGTTATCCGCTCACAXTTCC ACACAACATACGAGCCGGAAGCATAAAGTGTAAAGC C | 175 |
| DM510-16* | GFP151 | CTCGAGTACAACTTTAACTCACACAATGTAXAGATCA CGGCAGACAAACAAAAGAATGGAATC | 176 |
| DM510-13* | GFP66 | CCGGATAACGGGAAAAGCATTGAACACCGCXGGTCA GAGTAGTGACAAGTGTTGGCCA | 177 |
| DM510-11* | GFP66 | GGCCAACACTTGTCACTACTCTGACCXAGGGTGTTCA ATGCTTTTCCCGTTATCCGGA | 178 |
| BL412* | hEGFP | GGCGAGGAGCTGTTCACCGGGGTGGTGCCCATCXTGG TCGAGCTGGACGGCGACGTAAAC | 179 |
| BL414* | hEGFP | GGCGAGGAGCTGTTCACCGGGGTGGTXCCCATCCTGG TCGAGCTGGACGGCGACGTAAAC | 180 |
| DM510-20* | GFP151 | GATTCCATTCTTTTGTTTGTCTGCCGTGATTXATACATT GTGTGAGTTAAAGTTGTACTCGAGT | 181 |
| D8* | D8 | CACACAGGAAACAGCTATGACCCGGGTTATTACATGC GCTAGCACTTGGAATTCACAATACTXTCTTTAAGGAA ACCATAGTAAATCTCCTTCTTAAAGTTAAGCTTAACCC TATAGTGAGTCGTATTAATTTC | 182 |
| GFP151-33 | GFP151 | CTCGAGTACAACTTTAACTCACACAATGTAAXAATCA CGGCAGACAAACAAAAGAATGGAATC | 183 |
| GFP151-35 | GFP151 | CTCGAGTACAACTTTAACTCACACAATGTAAXCATCA CGGCAGACAAACAAAAGAATGGAATC | 184 |
| GFP151-37 | GFP151 | CTCGAGTACAACTTTAACTCACACAATGTAAXGATCA CGGCAGACAAACAAAAGAATGGAATC | 185 |
| GFP151-39 | GFP151 | CTCGAGTACAACTTTAACTCACACAATGTCAXTGTCA CGGCAGACAAACAAAAGAATGGAATC | 186 |
| GFP151-41 | GFP151 | CTCGAGTACAACTTTAACTCACACAATGTACXAATCA CGGCAGACAAACAAAAGAATGGAATC | 187 |
| GFP151 43* | GFP151 | CTCGAGTACAACTTTAACTCACACAATGTACXCATCA CGGCAGACAAACAAAAGAATGGAATC | 188 |
| DM510-19 | GFP151 | CTCGAGTACAACTTTAACTCACACAATGTACXGATCA CGGCAGACAAACAAAAGAATGGAATC | 89 1 |
| GFP151-47 | GFP151 | CTCGAGTACAACTTTAACTCACACAATGTACXTATCA CGGCAGACAAACAAAAGAATGGAATC | 190 |
| GFP151-49 | GFP151 | CTCGAGTACAACTTTAACTCACACAATGTAGXAATCA CGGCAGACAAACAAAAGAATGGAATC | 191 |
| GFP151-51* | GFP151 | CTCGAGTACAACTTTAACTCACACAATGTAGXCATCA CGGCAGACAAACAAAAGAATGGAATC | 192 |
| GFP151-53* | GFP151 | CTCGAGTACAACTTTAACTCACACAATGTAGXGATCA CGGCAGACAAACAAAAGAATGGAATC | 193 |
| GFP151-55 | GFP151 | CTCGAGTACAACTTTAACTCACACAATGTAGXTATCA CGGCAGACAAACAAAAGAATGGAATC | 194 |
| GFP151-57 | GFP151 | CTCGAGTACAACTTTAACTCACACAATGTATXAATCA CGGCAGACAAACAAAAGAATGGAATC | 195 |
| GFP151-59 | GFP151 | CTCGAGTACAACTTTAACTCACACAATGTATXCATCA CGGCAGACAAACAAAAGAATGGAATC | 196 |
| GFP151-61* | GFP151 | CTCGAGTACAACTTTAACTCACACAATGTATXGATCA CGGCAGACAAACAAAAGAATGGAATC | 197 |
| GFP151-63 | GFP151 | CTCGAGTACAACTTTAACTCACACAATGTATXTATCAC GGCAGACAAACAAAAGAATGGAATC | 198 |

TABLE 2-continued

| | | | |
|---|---|---|---|
| GFP151-69* | GFP151 | CTCGAGTACAACTTTAACTCACACAATGTAAGXATCA CGGCAGACAAACAAAAGAATGGAATC | 199 |
| ESer-69* | ESer | CTCTGGAACCCTTTCGGGTCGCCGGTTTAGXAGACCG GTGCCTTCAACCGCTCGGC | 200 |

Table 3 illustrate signal peptide sequences described herein.

| Signal Peptide ID | Sequences | SEQ ID NO: |
|---|---|---|
| pelB-SP1 | MKYLLPTAEAGLLLLAAQPAIA | 225 |
| malE_SP2 | MKIKTGARILALSELTTMMFSASALA | 226 |
| phoA_SP3 | MKQSTIALALLPLLFTPVTKA | 227 |
| treA_SP4 | MKSPAPSRPQKMALIPACIFLCFAALSVQA | 228 |
| pcoE_SP5 | MKKILVSFVAIMAVASSAMA | 229 |
| Chitosanase (Csn)-SP6 | MKISMQKADFWKKAAISLLVFTMFFTLMMSETVFAAGL NK | 230 |
| OmpA_SP7 | MKKTAIAIAVALAGFATVAQASAGLNKD | 231 |
| DsbAss | Protein:<br>MKKIWLALAGLVLAFSASA | 232 |
| | DNA:<br>ATGAAAAAGATTTGGCTGGCGCTGGCTGGTTTAGTTTT AGCGTTTAGCGCATCGGCG | 233 |
| PelBss | Protein:<br>MKYLLPTAAAGLLLLAAQPAMA | 234 |
| | DNA:<br>ATGAAATACCTGCTGCCGACCGCTGCTGCTGGTCTGCT GCTCCTCGCTGCCCAGCCGGCGATGGCG | 235 |
| PhoAss | Protein:<br>MKQSTIALALLPLLFTPVTKA | 227 |
| | DNA:<br>ATGAAACAAAGCACTATTGCACTGGCACTCTTACCGT TACTGTTTACCCCTGTGACAAAAGCG | 236 |
| NTss | Protein:<br>MKTHIVSSVTTTLLLGSILMNPVANA | 237 |
| | DNA:<br>ATGAAAACACATATAGTCAGCTCAGTAACAACAACAC TATTGCTAGGTTCCATATTAATGAATCCTGTCGCTAAT GCC | 238 |
| NSP1 | Protein:<br>MKYLLPWLALAGLVLAFSASA | 239 |
| | DNA:<br>ATGAAATACCTGCTGCCGTGGCTGGCGCTGGCTGGTT TAGTTTTAGCGTTTAGCGCATCGGCG | 240 |
| NSP2 | Protein:<br>MKKITAAAGLLLLAAFSASA | 241 |
| | DNA:<br>ATGAAAAAGATTACCGCTGCTGCTGGTCTGCTGCTCCT CGCTGCGTTTAGCGCATCGGCG | 242 |
| NSP3 | Protein:<br>MKKIWLALAGLVLAQPAMA | 243 |
| | DNA:<br>ATGAAAAAGATTTGGCTGGCGCTGGCTGGTTTAGTTTT AGCCCAGCCGGCGATGGCG | 244 |
| NSP3a | Protein:<br>MKKILVLGALALWAQPAMA | 245 |
| | DNA:<br>ATGAAAAAGATTTTAGTTTTAGGTGCTCTGGCGCTGTG GGCCCAGCCGGCGATGGCG | 246 |

-continued

| Signal Peptide ID | Sequences | SEQ ID NO: |
|---|---|---|
| NSP3b | Protein:<br>MKKIWLALVLLAGAQPAMA | 247 |
| | DNA:<br>ATGAAAAAGATTTGGCTGGCGTTAGTTTTACTGGCTG<br>GTGCCCAGCCGGCGATGGCG | 248 |
| NSP3c | Protein:<br>MKKILAGWLALVLAQPAMA | 249 |
| | DNA:<br>ATGAAAAAGATTCTGGCTGGTTGGCTGGCGTTAGTTTT<br>AGCCCAGCCGGCGATGGCG | 250 |
| NSP3d | Protein:<br>MKKILVLLAGWLAAQPAMA | 251 |
| | DNA:<br>ATGAAAAAGATTTTAGTTTTACTGGCTGGTTGGCTGGC<br>GGCCCAGCCGGCGATGGCG | 252 |
| NSP4 | Protein:<br>MKKITAAAGLLLLAAQPAMA | 253 |
| | DNA:<br>ATGAAAAAGATTACCGCTGCTGCTGGTCTGCTGCTCCT<br>CGCTGCCCAGCCGGCGATGGCG | 254 |
| NSP4a | Protein:<br>MKKILLLLGTAAAAAQPAMA | 255 |
| | DNA:<br>ATGAAAAAGATTCTGCTGCTCCTCGGTACCGCTGCTG<br>CTGCTGCCCAGCCGGCGATGGCG | 256 |
| NSP4b | Protein:<br>MKKILLLLLLLLLAQPAMA | 257 |
| | DNA:<br>ATGAAAAAGATTCTGCTGCTCCTCCTGCTGCTCCTCCT<br>GCTCGCCCAGCCGGCGATGGCG | 258 |
| NSP4c | Protein:<br>MKKIAAAAAAAAAAAQPAMA | 259 |
| | DNA:<br>ATGAAAAAGATTGCTGCTGCTGCTGCGGCGGCGGCGG<br>CTGCGGCCCAGCCGGCGATGGCG | 260 |
| NSP5 | Protein:<br>MKYLLPWLALAGLVLAQPAMA | 261 |
| | DNA:<br>ATGAAATACCTGCTGCCGTGGCTGGCGCTGGCTGGTT<br>TAGTTTTAGCCCAGCCGGCGATGGCG | 262 |
| NSP6 | Protein:<br>MKYLLPTAAAGLLLLAAFSASA | 263 |
| | DNA:<br>ATGAAATACCTGCTGCCGACCGCTGCTGCTGGTCTGCT<br>GCTCCTCGCTGCGTTTAGCGCATCGGCG | 264 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of incorporating one or more unnatural nucleoside triphosphates into a nucleic acid molecule in an *Escherichia coli* cell, comprising:

expressing in the *Escherichia coli* cell a nucleoside triphosphate transporter; and incubating the *Escherichia coli* cell with the one or more unnatural nucleoside triphosphates, wherein the one or more unnatural nucleoside triphosphates are thereby transported into the *Escherichia coli* cell by the nucleoside triphosphate transporter and incorporated into the nucleic acid molecule by a polymerase, and wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO: 8; or the amino acid sequence of the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

2. The method of claim 1, wherein the one or more unnatural nucleoside triphosphates comprise a base selected from:

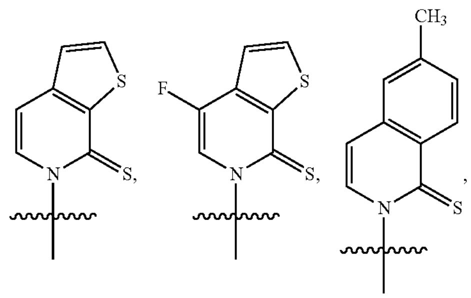

-continued

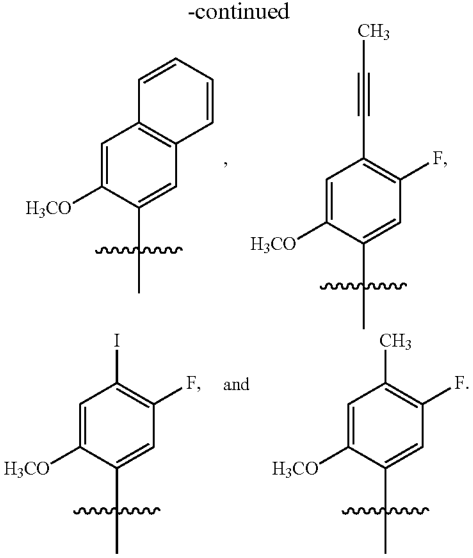

3. A method of transporting one or more unnatural nucleoside triphosphates into an *Escherichia coli* cell comprising:

expressing in the *Escherichia coli* cell a nucleoside triphosphate transporter; and incubating the *Escherichia coli* cell with the one or more unnatural nucleoside triphosphates, wherein the one or more unnatural nucleoside triphosphates are transported into the *Escherichia coli* cell, and wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO: 8; or the amino acid sequence of the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

4. The method of claim 3, wherein the one or more unnatural nucleoside triphosphates comprise a base selected from:

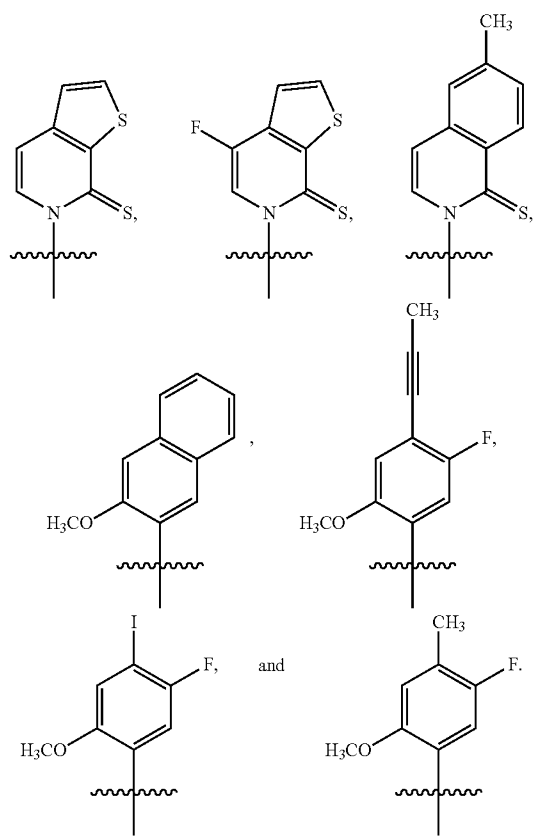

5. A method of increasing production of a nucleic acid molecule containing one or more unnatural nucleotides in an *Escherichia coli* cell, comprising:

incubating with the *Escherichia coli* cell an isolated and purified plasmid comprising a nucleic acid molecule encoding a nucleoside triphosphate transporter and a promoter region selected from a pSC plasmid and a lacZYA locus, wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO: 8; or the amino acid sequence of the nucleoside triphosphate transporter consists of an amino acid sequence in which 5 to 66 amino acids of the amino acid sequence of a PtNTT2 nucleoside triphosphate transporter are deleted from the N-terminus and is at least 90% identical to any one of SEQ ID NOs: 4, 6, and 8;

expressing in the *Escherichia coli* cell the nucleoside triphosphate transporter; and incubating the *Escherichia coli* cell with one or more unnatural nucleoside triphosphates, wherein the one or more unnatural nucleoside triphosphates are transported into the *Escherichia coli* cell by the nucleotide triphosphate transporter and the *Escherichia coli* cell incorporates the one or more unnatural nucleoside triphosphates into the nucleic acid molecule.

6. The method of claim 5, wherein the one or more unnatural nucleoside triphosphates comprises a base selected from:

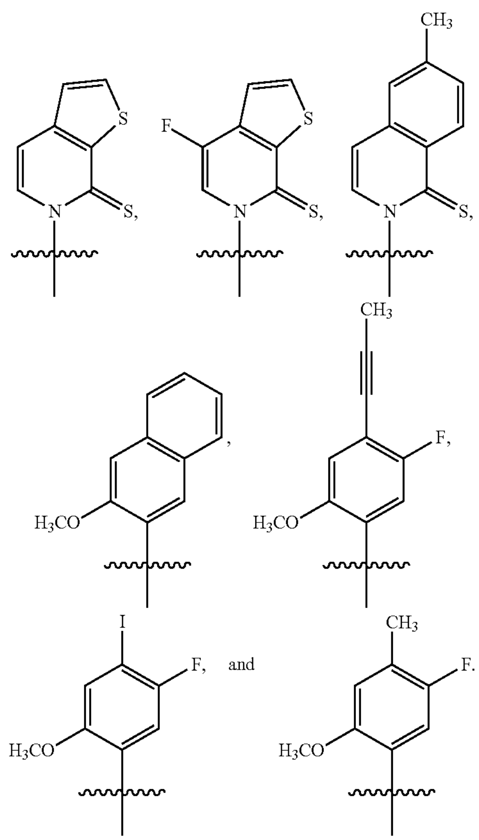

7. A method of increasing production of a nucleic acid molecule containing one or more unnatural nucleotides in an *Escherichia coli* cell, comprising:

expressing in the *Escherichia coli* cell a nucleoside triphosphate transporter; and incubating the *Escherichia coli* cell with one or more unnatural nucleoside triphosphates, wherein the one or more unnatural nucleoside triphosphates are transported into the *Escherichia coli* cell by the nucleoside triphosphate transporter and the *Escherichia coli* cell incorporates the one or more unnatural nucleoside triphosphates into the nucleic acid molecule, and wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO: 8; or the amino acid sequence of the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

8. The method of claim 7, wherein the one or more unnatural nucleoside triphosphates comprise a base selected from:

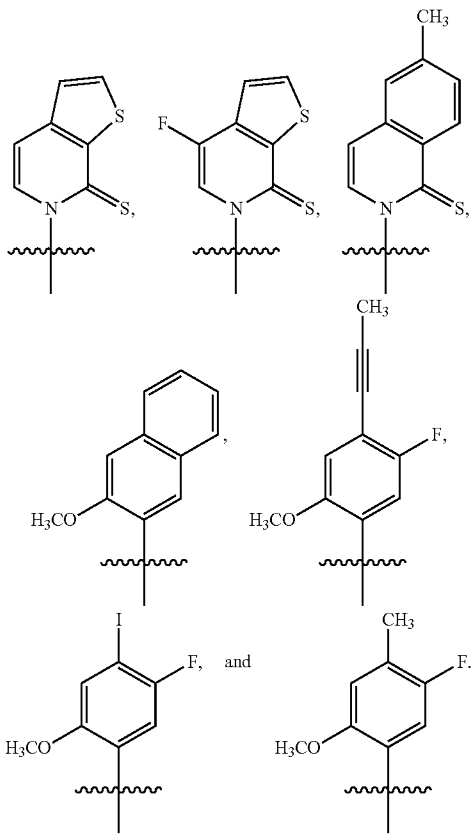

9. A method of increasing retention of one or more unnatural base pairs in an *Escherichia coli* cell, comprising: expressing in the *Escherichia coli* cell a nucleoside triphosphate transporter in the presence of one or more unnatural nucleoside triphosphates, wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO: 8; or the amino acid sequence of the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

10. The method of claim 9, wherein the nucleoside triphosphate transporter enables unnatural base pair retention of about 50%, 60%, 70%, 80%, 90%, 95%, 99% or more.

11. A method of decreasing doubling time of an *Escherichia coli* cell containing one or more unnatural nucleic acid molecules, comprising expressing in the *Escherichia coli* cell a nucleoside triphosphate transporter in the presence of one or more unnatural nucleoside triphosphates, wherein:

the amino acid sequence of the nucleoside triphosphate transporter consists of an amino acid sequence with at least 90% identity to SEQ ID NO: 4, at least 95% identity to SEQ ID NO: 6, or at least 97% identity to SEQ ID NO:8; or the amino acid sequence of the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

12. The method of claim 1, wherein the nucleoside triphosphate transporter consists of an amino acid sequence with 90% identity to SEQ ID NO: 4.

13. The method of claim 1, wherein the nucleoside triphosphate transporter consists of an amino acid sequence with 95% identity to SEQ ID NO: 4.

14. The method of claim 1, wherein the nucleoside triphosphate transporter consists of an amino acid sequence with 97% identity to SEQ ID NO: 4.

15. The method of claim 1, wherein the nucleoside triphosphate transporter consists of an amino acid sequence with 99% identity to SEQ ID NO: 4.

16. The method of claim 1, wherein the nucleoside triphosphate transporter consists of an amino acid sequence with 95% identity to SEQ ID NO: 6.

17. The method of claim 1, wherein the nucleoside triphosphate transporter consists of an amino acid sequence with 97% identity to SEQ ID NO: 6.

18. The method of claim 1, wherein the nucleoside triphosphate transporter consists of an amino acid sequence with 99% identity to SEQ ID NO: 6.

19. The method of claim 1, wherein the nucleoside triphosphate transporter consists of an amino acid sequence with 97% identity to SEQ ID NO: 8.

20. The method of claim 1, wherein the nucleoside triphosphate transporter consists of an amino acid sequence with 99% identity to SEQ ID NO: 8.

21. The method of claim 1, wherein the nucleoside triphosphate transporter consists of an amino acid sequence in which 5 to 66 amino acids are deleted from the N-terminus of the amino acid sequence of a PtNTT2 nucleoside triphosphate transporter and is at least 90% identical to any one of SEQ ID NOs: 4, 6, and 8.

22. The method of claim 1, wherein the nucleoside triphosphate transporter consists of an amino acid sequence in which the first 65 amino acids are deleted from the N-terminus of the amino acid sequence of a PtNTT2 nucleoside triphosphate transporter and is at least 90% identical to any one of SEQ ID NOs: 4, 6, and 8.

23. The method of claim 1, wherein the nucleoside triphosphate transporter consists of an amino acid sequence in which amino acids 23 through 65 are deleted from the amino acid sequence of a PtNTT2 nucleoside triphosphate transporter and is at least 90% identical to any one of SEQ ID NOs: 4, 6, and 8.

24. The method of claim 1, wherein the nucleoside triphosphate transporter consists of an amino acid sequence in which the first 22 amino acids are deleted from the N-terminus of the amino acid sequence of a PtNTT2 nucleoside triphosphate transporter and is at least 90% identical to any one of SEQ ID NOs: 4, 6, and 8.

25. The method of claim 1, wherein the nucleoside triphosphate transporter consists of the sequence of SEQ ID NO: 1 wherein 5 to 66 amino acids are deleted from the N-terminus.

* * * * *

SEQUENCE LISTING

<160> NUMBER OF SEQ ID NOS: 264

<210> SEQ ID NO 1
<211> LENGTH: 575
<212> TYPE: PRT
<213> ORGANISM: Phaeodactylum tricornutum

<400> SEQUENCE: 1

```
Met Arg Pro Tyr Pro Thr Ile Ala Leu Ile Ser Val Phe Leu Ser Ala
1               5                   10                  15

Ala Thr Arg Ile Ser Ala Thr Ser Ser His Gln Ala Ser Ala Leu Pro
            20                  25                  30

Val Lys Lys Gly Thr His Val Pro Asp Ser Pro Lys Leu Ser Lys Leu
        35                  40                  45

Tyr Ile Met Ala Lys Thr Lys Ser Val Ser Ser Ser Phe Asp Pro Pro
    50                  55                  60

Arg Gly Gly Ser Thr Val Ala Pro Thr Thr Pro Leu Ala Thr Gly Gly
65                  70                  75                  80

Ala Leu Arg Lys Val Arg Gln Ala Val Phe Pro Ile Tyr Gly Asn Gln
                85                  90                  95

Glu Val Thr Lys Phe Leu Leu Ile Gly Ser Ile Lys Phe Phe Ile Ile
            100                 105                 110

Leu Ala Leu Thr Leu Thr Arg Asp Thr Lys Asp Thr Leu Ile Val Thr
        115                 120                 125

Gln Cys Gly Ala Glu Ala Ile Ala Phe Leu Lys Ile Tyr Gly Val Leu
    130                 135                 140

Pro Ala Ala Thr Ala Phe Ile Ala Leu Tyr Ser Lys Met Ser Asn Ala
145                 150                 155                 160

Met Gly Lys Lys Met Leu Phe Tyr Ser Thr Cys Ile Pro Phe Phe Thr
                165                 170                 175

Phe Phe Gly Leu Phe Asp Val Phe Ile Tyr Pro Asn Ala Glu Arg Leu
            180                 185                 190

His Pro Ser Leu Glu Ala Val Gln Ala Ile Leu Pro Gly Gly Ala Ala
        195                 200                 205

Ser Gly Gly Met Ala Val Leu Ala Lys Ile Ala Thr His Trp Thr Ser
    210                 215                 220

Ala Leu Phe Tyr Val Met Ala Glu Ile Tyr Ser Ser Val Ser Val Gly
225                 230                 235                 240

Leu Leu Phe Trp Gln Phe Ala Asn Asp Val Val Asn Val Asp Gln Ala
                245                 250                 255

Lys Arg Phe Tyr Pro Leu Phe Ala Gln Met Ser Gly Leu Ala Pro Val
            260                 265                 270

Leu Ala Gly Gln Tyr Val Val Arg Phe Ala Ser Lys Ala Val Asn Phe
        275                 280                 285

Glu Ala Ser Met His Arg Leu Thr Ala Ala Val Thr Phe Ala Gly Ile
    290                 295                 300

Met Ile Cys Ile Phe Tyr Gln Leu Ser Ser Ser Tyr Val Glu Arg Thr
305                 310                 315                 320

Glu Ser Ala Lys Pro Ala Ala Asp Asn Glu Gln Ser Ile Lys Pro Lys
                325                 330                 335

Lys Lys Lys Pro Lys Met Ser Met Val Glu Ser Gly Lys Phe Leu Ala
            340                 345                 350

Ser Ser Gln Tyr Leu Arg Leu Ile Ala Met Leu Val Leu Gly Tyr Gly
        355                 360                 365

Leu Ser Ile Asn Phe Thr Glu Ile Met Trp Lys Ser Leu Val Lys Lys
    370                 375                 380

Gln Tyr Pro Asp Pro Leu Asp Tyr Gln Arg Phe Met Gly Asn Phe Ser
385                 390                 395                 400

Ser Ala Val Gly Leu Ser Thr Cys Ile Val Ile Phe Phe Gly Val His
                405                 410                 415

Val Ile Arg Leu Leu Gly Trp Lys Val Gly Ala Leu Ala Thr Pro Gly
```

```
            420                 425                 430

Ile Met Ala Ile Leu Ala Leu Pro Phe Phe Ala Cys Ile Leu Leu Gly
        435                 440                 445

Leu Asp Ser Pro Ala Arg Leu Glu Ile Ala Val Ile Phe Gly Thr Ile
    450                 455                 460

Gln Ser Leu Leu Ser Lys Thr Ser Lys Tyr Ala Leu Phe Asp Pro Thr
465                 470                 475                 480

Thr Gln Met Ala Tyr Ile Pro Leu Asp Asp Glu Ser Lys Val Lys Gly
                485                 490                 495

Lys Ala Ala Ile Asp Val Leu Gly Ser Arg Ile Gly Lys Ser Gly Gly
            500                 505                 510

Ser Leu Ile Gln Gln Gly Leu Val Phe Val Phe Gly Asn Ile Ile Asn
        515                 520                 525

Ala Ala Pro Val Val Gly Val Val Tyr Tyr Ser Val Leu Val Ala Trp
    530                 535                 540

Met Ser Ala Ala Gly Arg Leu Ser Gly Leu Phe Gln Ala Gln Thr Glu
545                 550                 555                 560

Met Asp Lys Ala Asp Lys Met Glu Ala Lys Thr Asn Lys Glu Lys
                565                 570                 575
```

<210> SEQ ID NO 2
<211> LENGTH: 1536
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atgggtggta gcaccgttgc accgaccaca ccgctggcaa ccggtggtgc actgcgtaaa     60

gttcgtcagg cagtttttcc gatttatggc aatcaagaag tgaccaaatt tctgctgatt    120

ggcagcatca aattctttat tatcctggca ctgaccctga cccgtgatac caaagatacc    180

ctgattgtta cccagtgtgg tgcagaagca attgcatttc tgaaaatcta tggtgttctg    240

cctgcagcaa ccgcatttat tgcactgtat agcaaaatga gcaacgcaat gggcaaaaaa    300

atgctgtttt atagcacctg tatcccgttc tttacctttt ttggtctgtt cgatgtgttc    360

atttatccga atgccgaacg tctgcatccg agcctggaag cagttcaggc aattctgcct    420

ggtggtgccg caagcggtgg tatggcagtt ctggcaaaaa ttgcaaccca ttggaccagc    480

gcactgtttt atgttatggc agaaatctat agcagcgtta gcgttggtct gctgttttgg    540

cagtttgcaa atgatgttgt taatgtggat caggccaaac gtttttatcc gctgtttgca    600

cagatgagcg gtctggcacc ggttctggca ggtcagtatg ttgttcgttt tgcaagcaaa    660

gccgttaatt ttgaagcaag catgcatcgt ctgaccgcag cagttacctt tgcaggtatt    720

atgatctgca tcttttatca gctgagcagc tcatatgttg aacgtaccga aagcgcaaaa    780

ccggcagcag ataatgaaca gagcattaaa ccgaagaaaa aaaaaccgaa aatgtcgatg    840

gtggaaagcg gtaaatttct ggcaagcagc cagtatctgc gtctgattgc aatgctggtt    900

ctgggttatg gtctgagcat taactttacc gaaatcatgt ggaaaagcct ggtgaaaaaa    960

cagtatccgg atccgctgga ttatcagcgt tttatgggta attttagcag cgcagttggt   1020

ctgagtacct gcattgttat ctttttttggc gtgcatgtta ttcgtctgct gggttggaaa   1080

gttggtgccc tggcaacacc gggtattatg gccattctgg cactgccgtt ttttgcatgt   1140

attctgctgg gcctggatag tccggcacgt ctggaaattg cagttatttt tggcaccatt   1200
```

```
cagagcctgc tgagcaaaac cagcaaatat gcactgtttg atccgaccac ccagatggca   1260

tatatcccgc tggatgatga aagcaaagtt aaaggcaaag cagccattga tgttctgggt   1320

agccgtattg gtaaatcagg tggtagcctg attcagcagg gtctggtttt tgtttttggc   1380

aatattatca atgccgcacc ggttgttggt gttgtgtatt atagcgttct ggttgcatgg   1440

atgagtgcag caggtcgtct gagtggtctg tttcaggcac agaccgaaat ggataaagca   1500

gataaaatgg aagccaaaac caacaaagaa aaatga                             1536
```

<210> SEQ ID NO 3
<211> LENGTH: 1536
<212> TYPE: DNA
<213> ORGANISM: Phaeodactylum tricornutum

<400> SEQUENCE: 3

```
atgggaggca gtactgttgc accaactaca ccgttggcaa ccggcggtgc gctccgcaaa     60

gtgcgacaag ccgtctttcc catctacgga aaccaagaag tcaccaaatt tctgctcatc    120

ggatccatta aattctttat aatcttggca ctcacgctca cgcgtgatac caaggacacg    180

ttgattgtca cgcaatgtgg tgccgaagcg attgcctttc tcaaaatata cggggtgcta    240

cccgcagcga ccgcatttat cgcgctctat tccaaaatgt ccaacgccat gggcaaaaaa    300

atgctatttt attccacttg cattcctttc tttacctttt tcgggctgtt tgatgttttc    360

atttacccga acgcggagcg actgcaccct agtttggaag ccgtgcaggc aattctcccg    420

ggcggtgccg catctggcgg catggcggtt ctggccaaga ttgcgacaca ctggacatcg    480

gccttatttt acgtcatggc ggaaatatat tcttccgtat cggtggggct attgttttgg    540

cagtttgcga acgacgtcgt caacgtggat caggccaagc gcttttatcc attatttgct    600

caaatgagtg gcctcgctcc agttttagcg ggccagtatg tggtacggtt tgccagcaaa    660

gcggtcaact ttgaggcatc catgcatcga ctcacggcgg ccgtaacatt tgctggtatt    720

atgatttgca tcttttacca actcagttcg tcatatgtgg agcgaacgga atcagcaaag    780

ccagcggcag ataacgagca gtctatcaaa ccgaaaaaga agaaacccaa aatgtccatg    840

gttgaatcgg ggaaatttct cgcgtcaagt cagtacctgc gtctaattgc catgctggtg    900

ctgggatacg gcctcagtat taactttacc gaaatcatgt ggaaaagctt ggtgaagaaa    960

caatatccag acccgctaga ttatcaacga tttatgggta acttctcgtc agcggttggt   1020

ttgagcacat gcattgttat tttcttcggt gtgcacgtga tccgtttgtt ggggtggaaa   1080

gtcggagcgt tggctacacc tgggatcatg gccattctag cgttaccctt ttttgcttgc   1140

attttgttgg gtttggatag tccagcacga ttggagatcg ccgtaatctt tggaacaatt   1200

cagagtttgc tgagcaaaac ctccaagtat gccctttttcg accctaccac acaaatggct   1260

tatattcctc tggacgacga atcaaaggtc aaaggaaaag cggcaattga tgttttggga   1320

tcgcggattg gcaagagtgg aggctcactg atccagcagg gcttggtctt tgtttttgga   1380

aatatcatta atgccgcacc tgtagtaggg gttgtctact acagtgtcct tgttgcgtgg   1440

atgagcgcag ctggccgact aagtgggctt tttcaagcac aaacagaaat ggataaggcc   1500

gacaaaatgg aggcaaagac caacaaagaa aagtag                             1536
```

<210> SEQ ID NO 4
<211> LENGTH: 511
<212> TYPE: PRT
<213> ORGANISM: Phaeodactylum tricornutum

<400> SEQUENCE: 4

```
Met Gly Gly Ser Thr Val Ala Pro Thr Thr Pro Leu Ala Thr Gly Gly
1               5                   10                  15

Ala Leu Arg Lys Val Arg Gln Ala Val Phe Pro Ile Tyr Gly Asn Gln
            20                  25                  30

Glu Val Thr Lys Phe Leu Leu Ile Gly Ser Ile Lys Phe Phe Ile Ile
        35                  40                  45

Leu Ala Leu Thr Leu Thr Arg Asp Thr Lys Asp Thr Leu Ile Val Thr
    50                  55                  60

Gln Cys Gly Ala Glu Ala Ile Ala Phe Leu Lys Ile Tyr Gly Val Leu
65                  70                  75                  80

Pro Ala Ala Thr Ala Phe Ile Ala Leu Tyr Ser Lys Met Ser Asn Ala
                85                  90                  95

Met Gly Lys Lys Met Leu Phe Tyr Ser Thr Cys Ile Pro Phe Phe Thr
            100                 105                 110

Phe Phe Gly Leu Phe Asp Val Phe Ile Tyr Pro Asn Ala Glu Arg Leu
        115                 120                 125

His Pro Ser Leu Glu Ala Val Gln Ala Ile Leu Pro Gly Gly Ala Ala
    130                 135                 140

Ser Gly Gly Met Ala Val Leu Ala Lys Ile Ala Thr His Trp Thr Ser
145                 150                 155                 160

Ala Leu Phe Tyr Val Met Ala Glu Ile Tyr Ser Ser Val Ser Val Gly
                165                 170                 175

Leu Leu Phe Trp Gln Phe Ala Asn Asp Val Val Asn Val Asp Gln Ala
            180                 185                 190

Lys Arg Phe Tyr Pro Leu Phe Ala Gln Met Ser Gly Leu Ala Pro Val
        195                 200                 205

Leu Ala Gly Gln Tyr Val Val Arg Phe Ala Ser Lys Ala Val Asn Phe
    210                 215                 220

Glu Ala Ser Met His Arg Leu Thr Ala Ala Val Thr Phe Ala Gly Ile
225                 230                 235                 240

Met Ile Cys Ile Phe Tyr Gln Leu Ser Ser Ser Tyr Val Glu Arg Thr
                245                 250                 255

Glu Ser Ala Lys Pro Ala Ala Asp Asn Glu Gln Ser Ile Lys Pro Lys
            260                 265                 270

Lys Lys Lys Pro Lys Met Ser Met Val Glu Ser Gly Lys Phe Leu Ala
        275                 280                 285

Ser Ser Gln Tyr Leu Arg Leu Ile Ala Met Leu Val Leu Gly Tyr Gly
    290                 295                 300

Leu Ser Ile Asn Phe Thr Glu Ile Met Trp Lys Ser Leu Val Lys Lys
305                 310                 315                 320

Gln Tyr Pro Asp Pro Leu Asp Tyr Gln Arg Phe Met Gly Asn Phe Ser
                325                 330                 335

Ser Ala Val Gly Leu Ser Thr Cys Ile Val Ile Phe Phe Gly Val His
            340                 345                 350

Val Ile Arg Leu Leu Gly Trp Lys Val Gly Ala Leu Ala Thr Pro Gly
        355                 360                 365

Ile Met Ala Ile Leu Ala Leu Pro Phe Phe Ala Cys Ile Leu Leu Gly
    370                 375                 380

Leu Asp Ser Pro Ala Arg Leu Glu Ile Ala Val Ile Phe Gly Thr Ile
385                 390                 395                 400

Gln Ser Leu Leu Ser Lys Thr Ser Lys Tyr Ala Leu Phe Asp Pro Thr
                405                 410                 415
```

```
Thr Gln Met Ala Tyr Ile Pro Leu Asp Asp Glu Ser Lys Val Lys Gly
            420                 425                 430

Lys Ala Ala Ile Asp Val Leu Gly Ser Arg Ile Gly Lys Ser Gly Gly
        435                 440                 445

Ser Leu Ile Gln Gln Gly Leu Val Phe Val Phe Gly Asn Ile Ile Asn
    450                 455                 460

Ala Ala Pro Val Val Gly Val Val Tyr Tyr Ser Val Leu Val Ala Trp
465                 470                 475                 480

Met Ser Ala Ala Gly Arg Leu Ser Gly Leu Phe Gln Ala Gln Thr Glu
                485                 490                 495

Met Asp Lys Ala Asp Lys Met Glu Ala Lys Thr Asn Lys Glu Lys
            500                 505                 510
```

<210> SEQ ID NO 5
<211> LENGTH: 1599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atgagaccat ttccgacgat tgccttgatt tcggtttttc tttcggcggc gactcgcatt     60

tcggcaggag gcagtactgt tgcaccaact acaccgttgg caaccggcgg tgcgctccgc    120

aaagtgcgac aagccgtctt tcccatctac ggaaaccaag aagtcaccaa atttctgctc    180

atcggatcca ttaaattctt tataatcttg gcactcacgc tcacgcgtga taccaaggac    240

acgttgattg tcacgcaatg tggtgccgaa gcgattgcct ttctcaaaat atacggggtg    300

ctacccgcag cgaccgcatt tatcgcgctc tattccaaaa tgtccaacgc catgggcaaa    360

aaaatgctat tttattccac ttgcattcct ttctttacct ttttcgggct gtttgatgtt    420

ttcatttacc cgaacgcgga gcgactgcac cctagtttgg aagccgtgca ggcaattctc    480

ccgggcggtg ccgcatctgg cggcatggcg gttctggcca agattgcgac acactggaca    540

tcggccttat tttacgtcat ggcggaaata tattcttccg tatcggtggg gctattgttt    600

tggcagtttg cgaacgacgt cgtcaacgtg gatcaggcca agcgctttta tccattattt    660

gctcaaatga gtggcctcgc tccagtttta gcgggccagt atgtggtacg gtttgccagc    720

aaagcggtca actttgaggc atccatgcat cgactcacgg cggccgtaac atttgctggt    780

attatgattt gcatctttta ccaactcagt tcgtcatatg tggagcgaac ggaatcagca    840

aagccagcgg cagataacga gcagtctatc aaaccgaaaa agaagaaacc caaaatgtcc    900

atggttgaat cggggaaatt tctcgcgtca agtcagtacc tgcgtctaat tgccatgctg    960

gtgctgggat acggcctcag tattaacttt accgaaatca tgtggaaaag cttggtgaag   1020

aaacaatatc cagacccgct agattatcaa cgatttatgg gtaacttctc gtcagcggtt   1080

ggtttgagca catgcattgt tattttcttc ggtgtgcacg tgatccgttt gttggggtgg   1140

aaagtcggag cgttggctac acctgggatc atggccattc tagcgttacc ctttttttgct  1200

tgcattttgt tgggtttgga tagtccagca cgattggaga tcgccgtaat ctttggaaca   1260

attcagagtt tgctgagcaa aacctccaag tatgcccttt tcgaccctac cacacaaatg   1320

gcttatattc ctctggacga cgaatcaaag gtcaaaggaa aagcggcaat tgatgttttg   1380

ggatcgcgga ttggcaagag tggaggctca ctgatccagc agggcttggt ctttgttttt   1440

ggaaatatca ttaatgccgc acctgtagta ggggttgtct actacagtgt ccttgttgcg   1500
```

```
tggatgagcg cagctggccg actaagtggg ctttttcaag cacaaacaga aatggataag   1560

gccgacaaaa tggaggcaaa gaccaacaaa gaaaagtag                          1599


<210> SEQ ID NO 6
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Pro Phe Pro Thr Ile Ala Leu Ile Ser Val Phe Leu Ser Ala
1               5                   10                  15

Ala Thr Arg Ile Ser Ala Gly Gly Ser Thr Val Ala Pro Thr Thr Pro
            20                  25                  30

Leu Ala Thr Gly Gly Ala Leu Arg Lys Val Arg Gln Ala Val Phe Pro
        35                  40                  45

Ile Tyr Gly Asn Gln Glu Val Thr Lys Phe Leu Leu Ile Gly Ser Ile
    50                  55                  60

Lys Phe Phe Ile Ile Leu Ala Leu Thr Leu Thr Arg Asp Thr Lys Asp
65                  70                  75                  80

Thr Leu Ile Val Thr Gln Cys Gly Ala Glu Ala Ile Ala Phe Leu Lys
                85                  90                  95

Ile Tyr Gly Val Leu Pro Ala Ala Thr Ala Phe Ile Ala Leu Tyr Ser
            100                 105                 110

Lys Met Ser Asn Ala Met Gly Lys Lys Met Leu Phe Tyr Ser Thr Cys
        115                 120                 125

Ile Pro Phe Phe Thr Phe Phe Gly Leu Phe Asp Val Phe Ile Tyr Pro
    130                 135                 140

Asn Ala Glu Arg Leu His Pro Ser Leu Glu Ala Val Gln Ala Ile Leu
145                 150                 155                 160

Pro Gly Gly Ala Ala Ser Gly Gly Met Ala Val Leu Ala Lys Ile Ala
                165                 170                 175

Thr His Trp Thr Ser Ala Leu Phe Tyr Val Met Ala Glu Ile Tyr Ser
            180                 185                 190

Ser Val Ser Val Gly Leu Leu Phe Trp Gln Phe Ala Asn Asp Val Val
        195                 200                 205

Asn Val Asp Gln Ala Lys Arg Phe Tyr Pro Leu Phe Ala Gln Met Ser
    210                 215                 220

Gly Leu Ala Pro Val Leu Ala Gly Gln Tyr Val Val Arg Phe Ala Ser
225                 230                 235                 240

Lys Ala Val Asn Phe Glu Ala Ser Met His Arg Leu Thr Ala Ala Val
                245                 250                 255

Thr Phe Ala Gly Ile Met Ile Cys Ile Phe Tyr Gln Leu Ser Ser Ser
            260                 265                 270

Tyr Val Glu Arg Thr Glu Ser Ala Lys Pro Ala Ala Asp Asn Glu Gln
        275                 280                 285

Ser Ile Lys Pro Lys Lys Lys Lys Pro Lys Met Ser Met Val Glu Ser
    290                 295                 300

Gly Lys Phe Leu Ala Ser Ser Gln Tyr Leu Arg Leu Ile Ala Met Leu
305                 310                 315                 320

Val Leu Gly Tyr Gly Leu Ser Ile Asn Phe Thr Glu Ile Met Trp Lys
                325                 330                 335
```

```
Ser Leu Val Lys Lys Gln Tyr Pro Asp Pro Leu Asp Tyr Gln Arg Phe
            340                 345                 350

Met Gly Asn Phe Ser Ser Ala Val Gly Leu Ser Thr Cys Ile Val Ile
        355                 360                 365

Phe Phe Gly Val His Val Ile Arg Leu Leu Gly Trp Lys Val Gly Ala
    370                 375                 380

Leu Ala Thr Pro Gly Ile Met Ala Ile Leu Ala Leu Pro Phe Phe Ala
385                 390                 395                 400

Cys Ile Leu Leu Gly Leu Asp Ser Pro Ala Arg Leu Glu Ile Ala Val
                405                 410                 415

Ile Phe Gly Thr Ile Gln Ser Leu Leu Ser Lys Thr Ser Lys Tyr Ala
            420                 425                 430

Leu Phe Asp Pro Thr Thr Gln Met Ala Tyr Ile Pro Leu Asp Asp Glu
        435                 440                 445

Ser Lys Val Lys Gly Lys Ala Ala Ile Asp Val Leu Gly Ser Arg Ile
    450                 455                 460

Gly Lys Ser Gly Gly Ser Leu Ile Gln Gln Gly Leu Val Phe Val Phe
465                 470                 475                 480

Gly Asn Ile Ile Asn Ala Ala Pro Val Val Gly Val Val Tyr Tyr Ser
                485                 490                 495

Val Leu Val Ala Trp Met Ser Ala Ala Gly Arg Leu Ser Gly Leu Phe
            500                 505                 510

Gln Ala Gln Thr Glu Met Asp Lys Ala Asp Lys Met Glu Ala Lys Thr
        515                 520                 525

Asn Lys Glu Lys
    530
```

<210> SEQ ID NO 7
<211> LENGTH: 1665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atgacttcct ctcatcaagc aagtgcactt cctctcaaaa agggaacgca tgtcccggac     60

tctccgaagt tgtcaaagct atatatcatg gccaaaacca agagtgtatc ctcgtccttc    120

gacccccctc ggggaggcag tactgttgca ccaactacac cgttggcaac cggcggtgcg    180

ctccgcaaag tgcgacaagc cgtctttccc atctacggaa accaagaagt caccaaattt    240

ctgctcatcg gatccattaa attctttata atcttggcac tcacgctcac gcgtgatacc    300

aaggacacgt tgattgtcac gcaatgtggt gccgaagcga ttgcctttct caaaatatac    360

ggggtgctac ccgcagcgac cgcatttatc gcgctctatt ccaaaatgtc caacgccatg    420

ggcaaaaaaa tgctatttta ttccacttgc attcctttct ttaccttttt cgggctgttt    480

gatgttttca tttacccgaa cgcggagcga ctgcacccta gtttggaagc cgtgcaggca    540

attctcccgg gcggtgccgc atctggcggc atggcggttc tggccaagat tgcgacacac    600

tggacatcgg ccttatttta cgtcatggcg gaaatatatt cttccgtatc ggtggggcta    660

ttgttttggc agtttgcgaa cgacgtcgtc aacgtggatc aggccaagcg cttttatcca    720

ttatttgctc aaatgagtgg cctcgctcca gttttagcgg gccagtatgt ggtacggttt    780

gccagcaaag cggtcaactt tgaggcatcc atgcatcgac tcacggcggc cgtaacattt    840

gctggtatta tgatttgcat cttttaccaa ctcagttcgt catatgtgga gcgaacggaa    900
```

```
tcagcaaagc cagcggcaga taacgagcag tctatcaaac cgaaaaagaa gaaacccaaa    960

atgtccatgg ttgaatcggg gaaatttctc gcgtcaagtc agtacctgcg tctaattgcc   1020

atgctggtgc tgggatacgg cctcagtatt aactttaccg aaatcatgtg gaaaagcttg   1080

gtgaagaaac aatatccaga cccgctagat tatcaacgat ttatgggtaa cttctcgtca   1140

gcggttggtt tgagcacatg cattgttatt ttcttcggtg tgcacgtgat ccgtttgttg   1200

gggtggaaag tcggagcgtt ggctacacct gggatcatgg ccattctagc gttacccttt   1260

tttgcttgca ttttgttggg tttggatagt ccagcacgat tggagatcgc cgtaatcttt   1320

ggaacaattc agagtttgct gagcaaaacc tccaagtatg cccttttcga ccctaccaca   1380

caaatggctt atattcctct ggacgacgaa tcaaaggtca aaggaaaagc ggcaattgat   1440

gttttgggat cgcggattgg caagagtgga ggctcactga tccagcaggg cttggtcttt   1500

gtttttggaa atatcattaa tgccgcacct gtagtagggg ttgtctacta cagtgtcctt   1560

gttgcgtgga tgagcgcagc tggccgacta agtgggcttt ttcaagcaca aacagaaatg   1620

gataaggccg acaaaatgga ggcaaagacc aacaaagaaa agtag                   1665
```

<210> SEQ ID NO 8
<211> LENGTH: 554
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Thr Ser Ser His Gln Ala Ser Ala Leu Pro Leu Lys Lys Gly Thr
1               5                   10                  15

His Val Pro Asp Ser Pro Lys Leu Ser Lys Leu Tyr Ile Met Ala Lys
            20                  25                  30

Thr Lys Ser Val Ser Ser Ser Phe Asp Pro Pro Arg Gly Gly Ser Thr
        35                  40                  45

Val Ala Pro Thr Thr Pro Leu Ala Thr Gly Gly Ala Leu Arg Lys Val
    50                  55                  60

Arg Gln Ala Val Phe Pro Ile Tyr Gly Asn Gln Glu Val Thr Lys Phe
65                  70                  75                  80

Leu Leu Ile Gly Ser Ile Lys Phe Phe Ile Ile Leu Ala Leu Thr Leu
                85                  90                  95

Thr Arg Asp Thr Lys Asp Thr Leu Ile Val Thr Gln Cys Gly Ala Glu
            100                 105                 110

Ala Ile Ala Phe Leu Lys Ile Tyr Gly Val Leu Pro Ala Ala Thr Ala
        115                 120                 125

Phe Ile Ala Leu Tyr Ser Lys Met Ser Asn Ala Met Gly Lys Lys Met
    130                 135                 140

Leu Phe Tyr Ser Thr Cys Ile Pro Phe Phe Thr Phe Phe Gly Leu Phe
145                 150                 155                 160

Asp Val Phe Ile Tyr Pro Asn Ala Glu Arg Leu His Pro Ser Leu Glu
                165                 170                 175

Ala Val Gln Ala Ile Leu Pro Gly Gly Ala Ala Ser Gly Gly Met Ala
            180                 185                 190

Val Leu Ala Lys Ile Ala Thr His Trp Thr Ser Ala Leu Phe Tyr Val
        195                 200                 205

Met Ala Glu Ile Tyr Ser Ser Val Ser Val Gly Leu Leu Phe Trp Gln
    210                 215                 220
```

```
Phe Ala Asn Asp Val Val Asn Val Asp Gln Ala Lys Arg Phe Tyr Pro
225                 230                 235                 240

Leu Phe Ala Gln Met Ser Gly Leu Ala Pro Val Leu Ala Gly Gln Tyr
                245                 250                 255

Val Val Arg Phe Ala Ser Lys Ala Val Asn Phe Glu Ala Ser Met His
            260                 265                 270

Arg Leu Thr Ala Ala Val Thr Phe Ala Gly Ile Met Ile Cys Ile Phe
        275                 280                 285

Tyr Gln Leu Ser Ser Ser Tyr Val Glu Arg Thr Glu Ser Ala Lys Pro
    290                 295                 300

Ala Ala Asp Asn Glu Gln Ser Ile Lys Pro Lys Lys Lys Lys Pro Lys
305                 310                 315                 320

Met Ser Met Val Glu Ser Gly Lys Phe Leu Ala Ser Ser Gln Tyr Leu
                325                 330                 335

Arg Leu Ile Ala Met Leu Val Leu Gly Tyr Gly Leu Ser Ile Asn Phe
            340                 345                 350

Thr Glu Ile Met Trp Lys Ser Leu Val Lys Lys Gln Tyr Pro Asp Pro
        355                 360                 365

Leu Asp Tyr Gln Arg Phe Met Gly Asn Phe Ser Ser Ala Val Gly Leu
    370                 375                 380

Ser Thr Cys Ile Val Ile Phe Phe Gly Val His Val Ile Arg Leu Leu
385                 390                 395                 400

Gly Trp Lys Val Gly Ala Leu Ala Thr Pro Gly Ile Met Ala Ile Leu
                405                 410                 415

Ala Leu Pro Phe Phe Ala Cys Ile Leu Leu Gly Leu Asp Ser Pro Ala
            420                 425                 430

Arg Leu Glu Ile Ala Val Ile Phe Gly Thr Ile Gln Ser Leu Leu Ser
        435                 440                 445

Lys Thr Ser Lys Tyr Ala Leu Phe Asp Pro Thr Thr Gln Met Ala Tyr
    450                 455                 460

Ile Pro Leu Asp Asp Glu Ser Lys Val Lys Gly Lys Ala Ala Ile Asp
465                 470                 475                 480

Val Leu Gly Ser Arg Ile Gly Lys Ser Gly Gly Ser Leu Ile Gln Gln
                485                 490                 495

Gly Leu Val Phe Val Phe Gly Asn Ile Ile Asn Ala Ala Pro Val Val
            500                 505                 510

Gly Val Val Tyr Tyr Ser Val Leu Val Ala Trp Met Ser Ala Ala Gly
        515                 520                 525

Arg Leu Ser Gly Leu Phe Gln Ala Gln Thr Glu Met Asp Lys Ala Asp
    530                 535                 540

Lys Met Glu Ala Lys Thr Asn Lys Glu Lys
545                 550
```

<210> SEQ ID NO 9
<211> LENGTH: 3013
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2349)..(2349)
<223> OTHER INFORMATION: Any unnatural nucleotide

<400> SEQUENCE: 9

```
aacgccagca acgcggcctt tttacggttc ctggcctttt gctggccttt tgctcacatg     60
ttctttcctg cgttatcccc tgattctgtg gataaccgta ttaccgcctt tgagtgagct    120
gataccgctc gccgcagccg aacgaccgag cgcagcgagt cagtgagcga ggaagcggaa    180
gagcgcctga tgcggtattt tctccttacg catctgtgcg gtatttcaca ccgcatatgg    240
tgcactctca gtacaatctg ctctgatgcc gcatagttaa gccagtatac actccgctat    300
cgctacgtga ctgggtcatg gctgcgcccc gacacccgcc aacacccgct gacgcgccct    360
gacgggcttg tctgctcccg gcatccgctt acagacaagc tgtgaccgtc tccgggagct    420
gcatgtgtca gaggttttca ccgtcatcac cgaaacgcgc gaggcagctg cggtaaagct    480
catcagcgtg gtcgtgaagc gattcacaga tgtctgcctg ttcatccgcg tccagctcgt    540
tgagtttctc cagaagcgtt aatgtctggc ttctgataaa gcgggccatg ttaagggcgg    600
tttttcctg tttggtcact gatgcctccg tgtaaggggg atttctgttc atgggggtaa    660
tgataccgat gaaacgagag aggatgctca cgatacgggt tactgatgat gaacatgccc    720
ggttactgga acgttgtgag ggtaaacaac tggcggtatg gatgcggcgg gaccagagaa    780
aaatcactca gggtcaatgc cagcgcttcg ttaatacaga tgtaggtgtt ccacagggta    840
gccagcagca tcctgcgatg cagatccgga acataatggt gcagggcgct gacttccgcg    900
tttccagact ttacgaaaca cggaaaccga agaccattca tgttgttgct caggtcgcag    960
acgttttgca gcagcagtcg cttcacgttc gctcgcgtat cggtgattca ttctgctaac   1020
cagtaaggca accccgccag cctagccggg tcctcaacga caggagcacg atcatgcgca   1080
cccgtggcca ggacccaacg ctgcccgaaa ttcttgaaga cgaaagggcc tcgtgatacg   1140
cctattttta taggttaatg tcatgataat aatggtttct tagacgtcag gtggcacttt   1200
tcggggaaat gtgcgcggaa cccctatttg tttatttttc taaatacatt caaatatgta   1260
tccgctcatg agacaataac cctgataaat gcttcaataa tattgaaaaa ggaagagtat   1320
gagtattcaa catttccgtg tcgcccttat tccctttttt gcggcatttt gccttcctgt   1380
ttttgctcac ccagaaacgc tggtgaaagt aaaagatgct gaagatcagt tgggtgcacg   1440
agtgggttac atcgaactgg atctcaacag cggtaagatc cttgagagtt ttcgccccga   1500
agaacgtttt ccaatgatga gcacttttaa agttctgcta tgtggcgcgg tattatcccg   1560
tgttgacgcc gggcaagagc aactcggtcg ccgcatacac tattctcaga atgacttggt   1620
tgagtactca ccagtcacag aaaagcatct tacggatggc atgacagtaa gagaattatg   1680
cagtgctgcc ataaccatga gtgataacac tgcggccaac ttacttctga caacgatcgg   1740
aggaccgaag gagctaaccg cttttttgca caacatgggg gatcatgtaa ctcgccttga   1800
tcgttgggaa ccggagctga atgaagccat accaaacgac gagcgtgaca ccacgatgcc   1860
tgcagcaatg gcaacaacgt tgcgcaaact attaactggc gaactactta ctctagcttc   1920
ccggcaacaa ttaatagact ggatggaggc ggataaagtt gcaggaccac ttctgcgctc   1980
ggcccttccg gctggctggt ttattgctga taaatctgga gccggtgagc gtggctctcg   2040
cggtatcatt gcagcactgg ggccagatgg taagccctcc cgtatcgtag ttatctacac   2100
gacggggagt caggcaacta tggatgaacg aaatagacag atcgctgaga taggtgcctc   2160
actgattaag cattggtaac tgtcagacca agtttactca tatatacttt agattgattt   2220
aaaacttcat ttttaattta aaaggatcta ggtgaagatc ctttttgata atctcatgac   2280
caaaatccct taacgtgagt tttcgttggc tttacacttt atgcttccgg ctcgtatgtt   2340
gtgtggaant gtgagcggat aacaatttca cacaggaaac agccactgag cgtcagaccc   2400
```

cgtagaaaag atcaaaggat cttcttgaga tcctttttt ctgcgcgtaa tctgctgctt 2460
gcaaacaaaa aaaccaccgc taccagcggt ggtttgtttg ccggatcaag agctaccaac 2520
tctttttccg aaggtaactg gcttcagcag agcgcagata ccaaatactg tccttctagt 2580
gtagccgtag ttaggccacc acttcaagaa ctctgtagca ccgcctacat acctcgctct 2640
gctaatcctg ttaccagtgg ctgctgccag tggcgataag tcgtgtctta ccgggttgga 2700
ctcaagacga tagttaccgg ataaggcgca gcggtcgggc tgaacggggg gttcgtgcac 2760
acagcccagc ttggagcgaa cgacctacac cgaactgaga tacctacagc gtgagctatg 2820
agaaagcgcc acgcttcccg aagggagaaa ggcggacagg tatccggtaa gcggcagggt 2880
cggaacagga gagcgcacga gggagcttcc agggggaaac gcctggtatc tttatagtcc 2940
tgtcgggttt cgccacctct gacttgagcg tcgatttttg tgatgctcgt caggggggcg 3000
gagcctatgg aaa 3013

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gggaggcagt actgttgcac 20

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ggtatatctc cttattaaag ttaaacaaaa ttatttctac agggg 45

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
taatacgact cactataggg 20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gctagttatt gctcagcgg 19

<210> SEQ ID NO 14
<211> LENGTH: 22
<212> TYPE: DNA

<213> ORGANISM: Artificial Sequence
<220> FEATURE:
<223> OTHER INFORMATION: Description of Artificial Sequence: Synthetic primer

<400> SEQUENCE: 14
ttacattaat tgcgttgcgc tc 22

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ttttggcgga tggcatttga gaagcacacg g 31

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
attctcacca ataaaaaacg cccgg 25

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
cctgtagaaa taattttgtt taactttaat aaggag 36

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ccccgcgcgt tggccgattc 20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gaagggcaat cagctgttg 19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cagggcaggg tcgttaaata g 21

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gacaccatcg aatggcgcaa aacctttcgc ggtatggcat gatagcgccc gg 52

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ccgggcgcta tcatgccata ccgcgaaagg ttttgcgcca ttcgatggtg tc 52

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
atttttctaa atacattcaa atatgtatcc gctcatgaga caataaccct g 51

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cagggttatt gtctcatgag cggatacata tttgaatgta tttagaaaaa t 51

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ttaggcaccc caggctttac actttatgct tccggctggt atgttgtgtg ga 52

<210> SEQ ID NO 26
<211> LENGTH: 52
<212> TYPE: DNA
<213> ORGANISM: Artificial Sequence
<220> FEATURE:

<223> OTHER INFORMATION: Description of Artificial Sequence: Synthetic primer

<400> SEQUENCE: 26
tccacacaac ataccagccg gaagcataaa gtgtaaagcc tggggtgcct aa 52

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctaggcaccc caggctttac actttatgct tccggctggt ataatgtgtg ga 52

<210> SEQ ID NO 28
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tccacacatt ataccagccg gaagcataaa gtgtaaagcc tggggtgcct ag 52

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ggggataacg caggaaagaa catg 24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gcacttttcg gggaaatgtg cg 22

<210> SEQ ID NO 31
<211> LENGTH: 75
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aattgcggcc tatatggatg ttggaaccgt aagagaaata gacaggcggt cctgtgacgg 60
aagatcactt cgcag 75

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tgctcacatg ttctttcctg cgttatcccc gcgtggtgaa ccaggc 46

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
accgcctgtc tatttctctt acggttcc 28

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cgcgcttaat gcgccgctac agggcgcgtc gattggtgcc agcgcgcag 49

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ggtatatctc cttattaaag ttaaacaaaa ttatttctac agg 43

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
cagccacgtt tctgcgaaaa c 21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
tacagcggtt ccttactggc 20

<210> SEQ ID NO 38
<211> LENGTH: 26
<212> TYPE: DNA
<213> ORGANISM: Artificial Sequence
<220> FEATURE:

<223> OTHER INFORMATION: Description of Artificial Sequence: Synthetic primer

<400> SEQUENCE: 38
gggtggtgaa tgtgaaacca gtaacg 26

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ctgggtgttt acttcggtct g 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ggccgtaata tccagctgaa c 21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
actagggtgc agtcgctccg 20

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ttaacctagg ctgctgccac cg 22

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gcgcaacgca attaatgtaa ttctgaaatg agctgttgac aattaatcat cggctcg 57

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aacaaaatta tttctacagg tccacacatt atacgagccg atgattaatt gtcaac 56

<210> SEQ ID NO 45
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gcgcaacgca attaatgtaa tcataaaaaa tttatttgct ttcaggaaaa tttttctg 58

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
aacaaaatta tttctacagg tgaatctatt atacagaaaa attttcctga aagcaaata 59

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gcgcaacgca attaatgtaa ttatctctgg cggtgttgac ataaatacca ctggcg 56

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
aacaaaatta tttctacagg tgtgctcagt atcaccgcca gtggtattta tgtcaac 57

<210> SEQ ID NO 49
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gcgcaacgca attaatgtaa ttttaaaaaa ttcatttgct aaacgcttca aattctcg 58

<210> SEQ ID NO 50
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
aacaaaatta tttctacagg tgaagtatat tatacgagaa tttgaagcgt ttagc 55

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tggggtgcct aatgagtgag c 21

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ctatgaccat gattacgcca agcttg 26

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tctcgcggta tcattgcagc actg 24

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
gccacgctca ccggctcc 18

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
aacgaaaact cacgttaagg g 21

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccactgagcg tcagacc 17

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gagacccgtc gttgacaatt aatcatcggc 30

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
gagaccattc tcaccaataa aaaacgcccg g 31

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
cggggtacca tggacaagaa gtactccatt 30

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ctagtctaga ttacaccttc ctcttcttct tggg 34

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ctccggggaa accgccgaag ccacgcggct caa 33

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
cttcggcggt ttccccggag tcgaacagga gggcgccaat gagg 44

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
aggaagaaga cgtctcacgc atcttactgc gcagatacgc 40

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
aagatgcgtg agacgtcttc ttcctcgtct cggtcgacag ttcataggtg attgctcagg 60

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gtcccaaatc gcagccaatc acattg 26

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gtcctgacca tcgtattggt tatctggc 28

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
atttagaggg cagtgccagc tcgtta 26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ctgcattcag gtaggcatca tgcgca 26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ctgggctacc tgcaagatta gcgatg 26

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
tgaaggactg ggcagaggcc ccctt 25

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
cgtaggtgtc tttgctcagt tgaagc 26

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tagccatctc attactaaag atctcct 27

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
cgatatcgtt ggtctcaacg acacaattgt aaaggttaga tct 43

<210> SEQ ID NO 74
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
caacgatatc ggtctcacac tgactgggcc tttcgtttta tct 43

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gcaatcacct atgaactgtc gac 23

<210> SEQ ID NO 76
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
aggaggaagg acgtctcatg cgccccgcat tcacacaatg tagtgatcag ttttagagct 60
agaaatagc 69

<210> SEQ ID NO 77
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
aggaggaagg acgtctcatg cgccccgcat tccaggatgg gtaccacccg ttttagagct 60
agaaatagc 69

<210> SEQ ID NO 78
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
aggaggaagg acgtctcatg cgccccgcat tcacacaatg tagtcatcag ttttagagct 60
agaaatagc 69

<210> SEQ ID NO 79
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
aggaggaagg acgtctcatg cgccccgcat tccaggatgg gcaccagccg ttttagagct 60
agaaatagc 69

<210> SEQ ID NO 80
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
aggaggaagg acgtctcatg cgccccgcat tccatgatgg gcaccacccg ttttagagct 60
agaaatagc 69

<210> SEQ ID NO 81
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
aggaggaagg acgtctcatg cgccccgcat tcacacaatg tatagatcag ttttagagct 60
agaaatagc 69

<210> SEQ ID NO 82
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
aggaggaagg acgtctcatg cgccccgcat tccaggatgg gcaccatccg ttttagagct 60
agaaatagc 69

<210> SEQ ID NO 83
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
aggaggaagg acgtctcatg cgccccgcat tgttgtgtgg aaatgtgagg ttttagagct 60
agaaatagc 69

<210> SEQ ID NO 84
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
aggaggaagg acgtctcatg cgccccgcat ttgtcactac tctgaccagg ttttagagct 60
agaaatagc 69

<210> SEQ ID NO 85
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
aggaggaagg acgtctcatg cgccccgcat ttgtcactac tctgaccaag ttttagagct 60
agaaatagc 69

<210> SEQ ID NO 86
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
aggaggaagg acgtctcatg cgccccgcat tcacacaatg tactcatcag ttttagagct 60
agaaatagc 69

<210> SEQ ID NO 87
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
aggaggaagg acgtctcatg cgccccgcat tccaagatgg gcaccacccg ttttagagct 60
agaaatagc 69

<210> SEQ ID NO 88
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
aggaggaagg acgtctcatg cgccccgcat tcacacaatg tattgatcag ttttagagct 60
agaaatagc 69

<210> SEQ ID NO 89
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
aggaggaagg acgtctcatg cgccccgcat tcacacaatg tataaatcag ttttagagct 60
agaaatagc 69

<210> SEQ ID NO 90
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
aggaggaagg acgtctcatg cgccccgcat tccaggatgg ggaccacccg ttttagagct 60
agaaatagc 69

<210> SEQ ID NO 91
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
aggaggaagg acgtctcatg cgccccgcat tttcacaata ctttctttag ttttagagct 60
agaaatagc 69

<210> SEQ ID NO 92
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gcatttcaca caatgtagga tcagttttag agctagaaat agc 43

<210> SEQ ID NO 93
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tgatcctaca ttgtgtgaaa tgcggggcgc atcttact 38

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
gcattaccag gatgggacca cccgttttag agctagaaat agc 43

<210> SEQ ID NO 95
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
gggtggtccc atcctggtaa tgcggggcgc atcttact 38

<210> SEQ ID NO 96
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 96

```
gcatttcaca caatgtagca tcagttttag agctagaaat agc                    43


<210> SEQ ID NO 97
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

tgatgctaca ttgtgtgaaa tgcggggcgc atcttact                          38


<210> SEQ ID NO 98
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

gcattaccag gatgggcacc accgttttag agctagaaat agc                    43


<210> SEQ ID NO 99
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

ggtggtgccc atcctggtaa tgcggggcgc atcttact                          38


<210> SEQ ID NO 100
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

gcattaccag atgggcacca cccgttttag agctagaaat agc                    43


<210> SEQ ID NO 101
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

gggtggtgcc catctggtaa tgcggggcgc atcttact                          38


<210> SEQ ID NO 102
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
```

gcatttcaca caatgtaaga tcagttttag agctagaaat agc 43

<210> SEQ ID NO 103
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
tgatcttaca ttgtgtgaaa tgcggggcgc atcttact 38

<210> SEQ ID NO 104
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
gcatttgttg tgtggaatgt gaggttttag agctagaaat agc 43

<210> SEQ ID NO 105
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
ctcacattcc acacaacaaa tgcggggcgc atcttact 38

<210> SEQ ID NO 106
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
gcattttgtc actactctga ccggttttag agctagaaat agc 43

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
cggtcagagt agtgacaaaa tgcggggcgc atcttact 38

<210> SEQ ID NO 108
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
gcattttgtc actactctga ccagttttag agctagaaat agc 43

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
tggtcagagt agtgacaaaa tgcggggcgc atcttact 38

<210> SEQ ID NO 110
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
gcatttcaca caatgtacca tcagttttag agctagaaat agc 43

<210> SEQ ID NO 111
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
tgatggtaca ttgtgtgaaa tgcggggcgc atcttact 38

<210> SEQ ID NO 112
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
gcatttcaca caatgtatga tcagttttag agctagaaat agc 43

<210> SEQ ID NO 113
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
tgatcataca ttgtgtgaaa tgcggggcgc atcttact 38

<210> SEQ ID NO 114
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
gcatttcaca caatgtataa tcagttttag agctagaaat agc 43

<210> SEQ ID NO 115
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
tgattataca ttgtgtgaaa tgcggggcgc atcttact 38

<210> SEQ ID NO 116
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
gcattattca caatacttct ttagttttag agctagaaat agc 43

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
taaagaagta ttgtgaataa tgcggggcgc atcttact 38

<210> SEQ ID NO 118
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
agaaggaaga cgtctcactg tcgaccaaaa aagcctgctc gttgagc 47

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
aagaaggacg tctcaacagt agtggcagcg gctaactaag 40

<210> SEQ ID NO 120
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
aggagaggac gtctctcgac caaaaaagcc tgctcgttga gcag 44

<210> SEQ ID NO 121
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
agtaagatgc gccccgcatt gaccaggatg ggcaccaccc gttttagagc tagaaatag 59

<210> SEQ ID NO 122
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ctatttctag ctctaaaacg ggtggtgccc atcctggtca atgcggggcg catcttact 59

<210> SEQ ID NO 123
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
gttttagagc tagaaatagc aagttaaaat aaggctagt 39

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
aatgcggggc gcatcttact 20

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
cattggcacc ggtctactaa ac 22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
aaacgtttag tagaccggtg cc 22

<210> SEQ ID NO 127

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127

cgcattcaca caatgtaagt atcagtttt                                    29


<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

ctctaaaact gatacttaca ttgtgtgaa                                    29


<210> SEQ ID NO 129
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129

gtttacgtcg ccgtccagct cgaccaggat gggcaccaac ccggtgaaca gctcctcgcc     60


<210> SEQ ID NO 130
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130

gtttacgtcg ccgtccagct cgaccaggat gggcaccagc ccggtgaaca gctcctcgcc     60


<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131

gtttacgtcg ccgtccagct cgaccaggat gggcaccatc ccggtgaaca gctcctcgcc     60


<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132

gtttacgtcg ccgtccagct cgaccaggat gggcaccacc ccggtgaaca gctcctcgcc     60


<210> SEQ ID NO 133
<211> LENGTH: 60
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 133
gcatcgccct cgccctcgcc ggacacgctg aacttgtggc cgtttacgtc gccgtccagc 60

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
tgcagtttca tttgatgctc gatgagttat ggtgagcaag ggcgaggagc tgttcaccgg 60

<210> SEQ ID NO 135
<211> LENGTH: 79
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
ttaatacgac tcactatagg gaccaggatg ggcaccaacc gttttagagc tagaaatagc 60
aagttaaaat aaggctagt 79

<210> SEQ ID NO 136
<211> LENGTH: 79
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
ttaatacgac tcactatagg gaccaggatg ggcaccagcc gttttagagc tagaaatagc 60
aagttaaaat aaggctagt 79

<210> SEQ ID NO 137
<211> LENGTH: 79
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
ttaatacgac tcactatagg gaccaggatg ggcaccatcc gttttagagc tagaaatagc 60
aagttaaaat aaggctagt 79

<210> SEQ ID NO 138
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
ttaatacgac tcactatagg gaccaggatg ggcaccaccc gttttagagc tatgctgttt 60
tg 62

<210> SEQ ID NO 139
<211> LENGTH: 82
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
aaaagcaccg actcggtgcc actttttcaa gttgataacg gactagcctt attttaactt 60
gctatttcta gctctaaaac gg 82

<210> SEQ ID NO 140
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
aagaggaaga ggttaatacg actcactata gggac 35

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
aaaagcaccg actcggtgcc 20

<210> SEQ ID NO 142
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
actagcctta ttttaacttg ctatttctag ctctaaaacg g 41

<210> SEQ ID NO 143
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
aagaaggaga aggtctctag tggagcaagg gcgaggagct gttcaccg 48

<210> SEQ ID NO 144
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
aagagaagag aggtctcatc gtgtttacgt cgccgtccag ctc 43

<210> SEQ ID NO 145
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
atgggtctcc agtggggcca acacttgtca ctac 34

<210> SEQ ID NO 146
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
atgggtctct tcgtttccgg ataacgggaa aagc 34

<210> SEQ ID NO 147
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
atgggtctcc agtggctcga gtacaacttt aactcacac 39

<210> SEQ ID NO 148
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
atgggtctct tcgttgattc cattcttttg tttgtctgc 39

<210> SEQ ID NO 149
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
atgggtctct catagctgtt tcctgtgtga aattgttatc c 41

<210> SEQ ID NO 150
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
atgggtctca ccccaggctt tacactttat gcttccg 37

<210> SEQ ID NO 151
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
atgggtctcc agtggctgtt tcctgtgtga aattgttatc c 41

<210> SEQ ID NO 152
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
atgggtctct tcgttggctt tacactttat gcttccg 37

<210> SEQ ID NO 153
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
atgggtctcc agtggcacac aggaaacagc tatgac 36

<210> SEQ ID NO 154
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
atgggtctct tcgttgggtt aagcttaact ttaagaagga g 41

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
atgggtctca cacaaactcg agtacaactt taactcacac 40

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
atgggtctcg attccattct tttgtttgtc tgc 33

<210> SEQ ID NO 157
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
attggtctcg gccgagcggt tgaaggcac 29

<210> SEQ ID NO 158
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
attggtctct ctggaaccct ttcgggtcg 29

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ggcgaggagc tgttcaccg 19

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
gtttacgtcg ccgtccagct c 21

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
ggccaacact tgtcactact 20

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
tccggataac gggaaaagc 19

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
ctcgagtaca actttaactc acac 24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
gattccattc ttttgtttgt ctgc 24

<210> SEQ ID NO 165
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
ctgtttcctg tgtgaaattg ttatcc 26

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
ggctttacac tttatgcttc cg 22

<210> SEQ ID NO 167
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
cccgggttat tacatgcgct agcact 26

<210> SEQ ID NO 168
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
gaaattaata cgactcacta tagggttaag cttaacttta agaaggag 48

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tgcaagcagc agattacgcg c 21

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gtaactgtca gaccaagttt actc 24

<210> SEQ ID NO 171
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: dNaM

<400> SEQUENCE: 171
ggcgaggagc tgttcaccgg gntggtgccc atcctggtcg agctggacgg cgacgtaaac 60

<210> SEQ ID NO 172
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: dNaM

<400> SEQUENCE: 172
gtttacgtcg ccgtccagct cgaccaggat gggnaccacc ccggtgaaca gctcctcgcc 60

<210> SEQ ID NO 173
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: dNaM

<400> SEQUENCE: 173
gtttacgtcg ccgtccagct cgaccangat gggcaccacc ccggtgaaca gctcctcgcc 60

```
<210> SEQ ID NO 174
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: dNaM

<400> SEQUENCE: 174

gtttacgtcg ccgtccagct cgaccaggat gggcaccanc ccggtgaaca gctcctcgcc     60


<210> SEQ ID NO 175
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: dNaM

<400> SEQUENCE: 175

ctgtttcctg tgtgaaattg ttatccgctc acanttccac acaacatacg agccggaagc     60

ataaagtgta aagcc                                                      75


<210> SEQ ID NO 176
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: dNaM

<400> SEQUENCE: 176

ctcgagtaca actttaactc acacaatgta nagatcacgg cagacaaaca aaagaatgga     60

atc                                                                   63


<210> SEQ ID NO 177
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: dNaM

<400> SEQUENCE: 177

ccggataacg ggaaaagcat tgaacaccgc nggtcagagt agtgacaagt gttggcca       58


<210> SEQ ID NO 178
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<221> NAME/KEY: modified_base
<222> LOCATION: (27)..(27)
<223> OTHER INFORMATION: dNaM

<400> SEQUENCE: 178
ggccaacact tgtcactact ctgaccnagg gtgttcaatg cttttcccgt tatccgga 58

<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (34)..(34)
<223> OTHER INFORMATION: dNaM

<400> SEQUENCE: 179
ggcgaggagc tgttcaccgg ggtggtgccc atcntggtcg agctggacgg cgacgtaaac 60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (27)..(27)
<223> OTHER INFORMATION: dNaM

<400> SEQUENCE: 180
ggcgaggagc tgttcaccgg ggtggtnccc atcctggtcg agctggacgg cgacgtaaac 60

<210> SEQ ID NO 181
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 181
gattccattc ttttgtttgt ctgccgtgat tnatacattg tgtgagttaa agttgtactc 60
gagt 64

<210> SEQ ID NO 182
<211> LENGTH: 134
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (63)..(63)
<223> OTHER INFORMATION: dNaM

<400> SEQUENCE: 182
cacacaggaa acagctatga cccgggttat tacatgcgct agcacttgga attcacaata 60

```
ctntctttaa ggaaaccata gtaaatctcc ttcttaaagt taagcttaac cctatagtga    120

gtcgtattaa tttc                                                      134


<210> SEQ ID NO 183
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 183

ctcgagtaca actttaactc acacaatgta anaatcacgg cagacaaaca aaagaatgga     60

atc                                                                   63


<210> SEQ ID NO 184
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 184

ctcgagtaca actttaactc acacaatgta ancatcacgg cagacaaaca aaagaatgga     60

atc                                                                   63


<210> SEQ ID NO 185
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 185

ctcgagtaca actttaactc acacaatgta angatcacgg cagacaaaca aaagaatgga     60

atc                                                                   63


<210> SEQ ID NO 186
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 186

ctcgagtaca actttaactc acacaatgtc antgtcacgg cagacaaaca aaagaatgga     60

atc                                                                   63
```

<210> SEQ ID NO 187
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 187
ctcgagtaca actttaactc acacaatgta cnaatcacgg cagacaaaca aaagaatgga 60
atc 63

<210> SEQ ID NO 188
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 188
ctcgagtaca actttaactc acacaatgta cncatcacgg cagacaaaca aaagaatgga 60
atc 63

<210> SEQ ID NO 189
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 189
ctcgagtaca actttaactc acacaatgta cngatcacgg cagacaaaca aaagaatgga 60
atc 63

<210> SEQ ID NO 190
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 190
ctcgagtaca actttaactc acacaatgta cntatcacgg cagacaaaca aaagaatgga 60
atc 63

<210> SEQ ID NO 191

<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 191
ctcgagtaca actttaactc acacaatgta gnaatcacgg cagacaaaca aaagaatgga 60
atc 63

<210> SEQ ID NO 192
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 192
ctcgagtaca actttaactc acacaatgta gncatcacgg cagacaaaca aaagaatgga 60
atc 63

<210> SEQ ID NO 193
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 193
ctcgagtaca actttaactc acacaatgta gngatcacgg cagacaaaca aaagaatgga 60
atc 63

<210> SEQ ID NO 194
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: dNaM

<400> SEQUENCE: 194
ctcgagtaca actttaactc acacaatgta gntatcacgg cagacaaaca aaagaatgga 60
atc 63

<210> SEQ ID NO 195
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 195
ctcgagtaca actttaactc acacaatgta tnaatcacgg cagacaaaca aaagaatgga     60
atc                                                                   63

<210> SEQ ID NO 196
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 196
ctcgagtaca actttaactc acacaatgta tncatcacgg cagacaaaca aaagaatgga     60
atc                                                                   63

<210> SEQ ID NO 197
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 197
ctcgagtaca actttaactc acacaatgta tngatcacgg cagacaaaca aaagaatgga     60
atc                                                                   63

<210> SEQ ID NO 198
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dNaM

<400> SEQUENCE: 198
ctcgagtaca actttaactc acacaatgta tntatcacgg cagacaaaca aaagaatgga     60
atc                                                                   63

<210> SEQ ID NO 199
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<221> NAME/KEY: modified_base
<222> LOCATION: (33)..(33)
<223> OTHER INFORMATION: dNaM

<400> SEQUENCE: 199
ctcgagtaca actttaactc acacaatgta agnatcacgg cagacaaaca aaagaatgga 60
atc 63

<210> SEQ ID NO 200
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (31)..(31)
<223> OTHER INFORMATION: dNaM

<400> SEQUENCE: 200
ctctggaacc ctttcgggtc gccggtttag nagaccggtg ccttcaaccg ctcggc 56

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (18)..(18)
<223> OTHER INFORMATION: dC, dT, dA, dG, dTPT3 or dNaM
<220> FEATURE:
<223> OTHER INFORMATION: See specification as filed for detailed description of substitutions and preferred embodiments

<400> SEQUENCE: 201
ctggtcctac ccgtggtngg tcc 23

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (18)..(18)
<223> OTHER INFORMATION: g, a, u or c
<220> FEATURE:
<223> OTHER INFORMATION: See specification as filed for detailed description of substitutions and preferred embodiments

<400> SEQUENCE: 202
gaccaggatg ggcaccancc 20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 203
gaccaggaug ggcaccaccc 20

<210> SEQ ID NO 204
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 204
guugugugga aaugugag 18

<210> SEQ ID NO 205
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 205
uguugugugg aaugugag 18

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (16)..(16)
<223> OTHER INFORMATION: dTPT3

<400> SEQUENCE: 206
guatgttgtg tggaantgtg ag 22

<210> SEQ ID NO 207
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(12)

<400> SEQUENCE: 207 tca cat ttc cac a 13
Ser His Phe His
1

<210> SEQ ID NO 208
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Ser His Phe His
1

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (14)..(14)
<223> OTHER INFORMATION: dNaM

<400> SEQUENCE: 209
tcacacaatg tagngatcac gg 22

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (12)..(12)
<223> OTHER INFORMATION: dNaM

<400> SEQUENCE: 210
accaggatgg gnaccacccc gg 22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (14)..(14)
<223> OTHER INFORMATION: dNaM

<400> SEQUENCE: 211
tcacacaatg tagncatcac gg 22

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (17)..(17)
<223> OTHER INFORMATION: dTPT3

<400> SEQUENCE: 212
accaggatgg gcaccanccc gg 22

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(5)
<223> OTHER INFORMATION: dNaM

<400> SEQUENCE: 213
accangatgg gcaccacccc gg 22

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)
<223> OTHER INFORMATION: dNaM

<400> SEQUENCE: 214
tcacacaatg tanagatcac gg 22

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (17)..(17)
<223> OTHER INFORMATION: dNaM

<400> SEQUENCE: 215
accaggatgg gcaccanccc gg 22

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)
<223> OTHER INFORMATION: dTPT3

<400> SEQUENCE: 216
tgttgtgtgg aantgtgagc gg 22

<210> SEQ ID NO 217
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (18)..(18)
<223> OTHER INFORMATION: dTPT3

<400> SEQUENCE: 217
ttgtcactac tctgaccngc gg 22

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (18)..(18)
<223> OTHER INFORMATION: dNaM

<400> SEQUENCE: 218
ttgtcactac tctgaccnag gg 22

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (14)..(14)
<223> OTHER INFORMATION: dNaM

<400> SEQUENCE: 219
tcacacaatg tacncatcac gg 22

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(5)
<223> OTHER INFORMATION: dTPT3

<400> SEQUENCE: 220
accangatgg gcaccacccc gg 22

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (14)..(14)
<223> OTHER INFORMATION: dNaM

<400> SEQUENCE: 221
tcacacaatg tatngatcac gg 22

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (14)..(14)
<223> OTHER INFORMATION: dTPT3

<400> SEQUENCE: 222
tcacacaatg tatnaatcac gg 22

<210> SEQ ID NO 223
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (12)..(12)
<223> OTHER INFORMATION: dTPT3

<400> SEQUENCE: 223
accaggatgg gnaccacccc gg 22

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(13)
<223> OTHER INFORMATION: dNaM

<400> SEQUENCE: 224
attcacaata ctntctttaa gg 22

<210> SEQ ID NO 225
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Met Lys Tyr Leu Leu Pro Thr Ala Glu Ala Gly Leu Leu Leu Leu Ala
1 5 10 15

Ala Gln Pro Ala Ile Ala
20

<210> SEQ ID NO 226
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Met Lys Ile Lys Thr Gly Ala Arg Ile Leu Ala Leu Ser Glu Leu Thr
1 5 10 15

Thr Met Met Phe Ser Ala Ser Ala Leu Ala
20 25

<210> SEQ ID NO 227
<211> LENGTH: 21
<212> TYPE: PRT
<213> ORGANISM: Artificial Sequence
<220> FEATURE:

<223> OTHER INFORMATION: Description of Artificial Sequence: Synthetic peptide

<400> SEQUENCE: 227

```
Met Lys Gln Ser Thr Ile Ala Leu Ala Leu Leu Pro Leu Leu Phe Thr
1               5                   10                  15

Pro Val Thr Lys Ala
            20
```

<210> SEQ ID NO 228
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

```
Met Lys Ser Pro Ala Pro Ser Arg Pro Gln Lys Met Ala Leu Ile Pro
1               5                   10                  15

Ala Cys Ile Phe Leu Cys Phe Ala Ala Leu Ser Val Gln Ala
            20                  25                  30
```

<210> SEQ ID NO 229
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

```
Met Lys Lys Ile Leu Val Ser Phe Val Ala Ile Met Ala Val Ala Ser
1               5                   10                  15

Ser Ala Met Ala
            20
```

<210> SEQ ID NO 230
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

```
Met Lys Ile Ser Met Gln Lys Ala Asp Phe Trp Lys Lys Ala Ala Ile
1               5                   10                  15

Ser Leu Leu Val Phe Thr Met Phe Phe Thr Leu Met Met Ser Glu Thr
            20                  25                  30

Val Phe Ala Ala Gly Leu Asn Lys
        35                  40
```

<210> SEQ ID NO 231
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

```
Met Lys Lys Thr Ala Ile Ala Ile Ala Val Ala Leu Ala Gly Phe Ala
1               5                   10                  15
```

```
Thr Val Ala Gln Ala Ser Ala Gly Leu Asn Lys Asp
            20                  25


<210> SEQ ID NO 232
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Met Lys Lys Ile Trp Leu Ala Leu Ala Gly Leu Val Leu Ala Phe Ser
1               5                   10                  15

Ala Ser Ala


<210> SEQ ID NO 233
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233

atgaaaaaga tttggctggc gctggctggt ttagttttag cgtttagcgc atcggcg        57


<210> SEQ ID NO 234
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 235
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235

atgaaatacc tgctgccgac cgctgctgct ggtctgctgc tcctcgctgc ccagccggcg     60

atggcg                                                                66


<210> SEQ ID NO 236
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236

atgaaacaaa gcactattgc actggcactc ttaccgttac tgtttacccc tgtgacaaaa     60

gcg                                                                   63
```

<210> SEQ ID NO 237
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

```
Met Lys Thr His Ile Val Ser Ser Val Thr Thr Thr Leu Leu Leu Gly
1               5                   10                  15

Ser Ile Leu Met Asn Pro Val Ala Asn Ala
            20                  25
```

<210> SEQ ID NO 238
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238

```
atgaaaacac atatagtcag ctcagtaaca acaacactat tgctaggttc catattaatg     60

aatcctgtcg ctaatgcc                                                    78
```

<210> SEQ ID NO 239
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

```
Met Lys Tyr Leu Leu Pro Trp Leu Ala Leu Ala Gly Leu Val Leu Ala
1               5                   10                  15

Phe Ser Ala Ser Ala
            20
```

<210> SEQ ID NO 240
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 240

```
atgaaatacc tgctgccgtg gctggcgctg gctggtttag ttttagcgtt tagcgcatcg     60

gcg                                                                    63
```

<210> SEQ ID NO 241
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

```
Met Lys Lys Ile Thr Ala Ala Ala Gly Leu Leu Leu Leu Ala Ala Phe
1               5                   10                  15

Ser Ala Ser Ala
```

20

<210> SEQ ID NO 242
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 242
atgaaaaaga ttaccgctgc tgctggtctg ctgctcctcg ctgcgtttag cgcatcggcg 60

<210> SEQ ID NO 243
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Met Lys Lys Ile Trp Leu Ala Leu Ala Gly Leu Val Leu Ala Gln Pro
1 5 10 15

Ala Met Ala

<210> SEQ ID NO 244
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
atgaaaaaga tttggctggc gctggctggt ttagttttag cccagccggc gatggcg 57

<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Met Lys Lys Ile Leu Val Leu Gly Ala Leu Ala Leu Trp Ala Gln Pro
1 5 10 15

Ala Met Ala

<210> SEQ ID NO 246
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 246
atgaaaaaga ttttagtttt aggtgctctg gcgctgtggg cccagccggc gatggcg 57

<210> SEQ ID NO 247
<211> LENGTH: 19
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 247

Met Lys Lys Ile Trp Leu Ala Leu Val Leu Leu Ala Gly Ala Gln Pro
1               5                   10                  15

Ala Met Ala

<210> SEQ ID NO 248
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
atgaaaaaga tttggctggc gttagtttta ctggctggtg cccagccggc gatggcg        57

<210> SEQ ID NO 249
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Met Lys Lys Ile Leu Ala Gly Trp Leu Ala Leu Val Leu Ala Gln Pro
1               5                   10                  15

Ala Met Ala

<210> SEQ ID NO 250
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
atgaaaaaga ttctggctgg ttggctggcg ttagttttag cccagccggc gatggcg        57

<210> SEQ ID NO 251
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Met Lys Lys Ile Leu Val Leu Leu Ala Gly Trp Leu Ala Ala Gln Pro
1               5                   10                  15

Ala Met Ala

<210> SEQ ID NO 252
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
atgaaaaaga ttttagtttt actggctggt tggctggcgg cccagccggc gatggcg 57

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Met Lys Lys Ile Thr Ala Ala Ala Gly Leu Leu Leu Leu Ala Ala Gln
1 5 10 15

Pro Ala Met Ala
20

<210> SEQ ID NO 254
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254
atgaaaaaga ttaccgctgc tgctggtctg ctgctcctcg ctgcccagcc ggcgatggcg 60

<210> SEQ ID NO 255
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Met Lys Lys Ile Leu Leu Leu Leu Gly Thr Ala Ala Ala Ala Ala Gln
1 5 10 15

Pro Ala Met Ala
20

<210> SEQ ID NO 256
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
atgaaaaaga ttctgctgct cctcggtacc gctgctgctg ctgcccagcc ggcgatggcg 60

<210> SEQ ID NO 257
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Met Lys Lys Ile Leu Leu Leu Leu Leu Leu Leu Leu Leu Leu Ala Gln
1 5 10 15

Pro Ala Met Ala
20

<210> SEQ ID NO 258
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 258
atgaaaaaga ttctgctgct cctcctgctg ctcctcctgc tcgcccagcc ggcgatggcg 60

<210> SEQ ID NO 259
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Met Lys Lys Ile Ala Ala Ala Ala Ala Ala Ala Ala Ala Ala Ala Gln
1 5 10 15

Pro Ala Met Ala
20

<210> SEQ ID NO 260
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 260
atgaaaaaga ttgctgctgc tgctgcggcg gcggcggctg cggcccagcc ggcgatggcg 60

<210> SEQ ID NO 261
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Met Lys Tyr Leu Leu Pro Trp Leu Ala Leu Ala Gly Leu Val Leu Ala
1 5 10 15

Gln Pro Ala Met Ala
20

<210> SEQ ID NO 262
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
atgaaatacc tgctgccgtg gctggcgctg gctggtttag ttttagccca gccggcgatg 60
gcg 63

<210> SEQ ID NO 263
<211> LENGTH: 22
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 263

Met Lys Tyr Leu Leu Pro Thr Ala Ala Ala Gly Leu Leu Leu Leu Ala
1               5                   10                  15

Ala Phe Ser Ala Ser Ala
            20


<210> SEQ ID NO 264
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264

atgaaatacc tgctgccgac cgctgctgct ggtctgctgc tcctcgctgc gtttagcgca     60

tcggcg                                                                66
```